US011638827B2

(12) United States Patent
Price et al.

(10) Patent No.: US 11,638,827 B2
(45) Date of Patent: May 2, 2023

(54) CURRENT SOURCE DRIVE-SENSE CIRCUIT (DSC) SERVICED PACEMAKER

(71) Applicant: SIGMASENSE, LLC., Wilmington, DE (US)

(72) Inventors: John Christopher Price, Austin, TX (US); Shayne X. Short, Conroe, TX (US); Timothy W. Markison, Mesa, AZ (US)

(73) Assignee: SIGMASENSE, LLC., Wilmington, DE (US)

( * ) Notice: Subject to any disclaimer, the term of this patent is extended or adjusted under 35 U.S.C. 154(b) by 177 days.

(21) Appl. No.: 17/331,949

(22) Filed: May 27, 2021

(65) Prior Publication Data

US 2021/0379377 A1 Dec. 9, 2021

Related U.S. Application Data

(63) Continuation of application No. 16/891,543, filed on Jun. 3, 2020, now Pat. No. 11,504,535.

(51) Int. Cl.
*A61N 1/362* (2006.01)
*A61N 1/375* (2006.01)
*A61N 1/37* (2006.01)

(52) U.S. Cl.
CPC ......... *A61N 1/3624* (2013.01); *A61N 1/3702* (2013.01); *A61N 1/3752* (2013.01)

(58) Field of Classification Search
None
See application file for complete search history.

(56) References Cited

U.S. PATENT DOCUMENTS

| 6,218,972 B1 | 4/2001 | Groshong |
| 6,665,013 B1 | 12/2003 | Fossum et al. |
| 7,528,755 B2 | 5/2009 | Hammerschmidt |
| 8,031,094 B2 | 10/2011 | Hotelling |
| 8,089,289 B1 | 1/2012 | Kremin et al. |
| 8,279,180 B2 | 10/2012 | Hotelling et al. |
| 8,547,114 B2 | 10/2013 | Kremin |

(Continued)

OTHER PUBLICATIONS

Baker; How delta-sigma ADCs work. Part 1; Analog Applications Journal; Oct. 1, 2011; 6 pgs.

(Continued)

*Primary Examiner* — Paula J Stice
(74) *Attorney, Agent, or Firm* — Garlick & Markison; Timothy W. Markison; Shayne X. Short

(57) ABSTRACT

A pacemaker system includes a drive-sense circuit (DSC) operably coupled to a pacemaker lead. The DSC generates a pace signal including electrical impulses based on a reference signal. The DSC provides the pace signal via the pacemaker lead to an electrically responsive portion of a cardiac conductive system of a subject to facilitate cardiac operation of a cardiovascular system of the subject. The DSC senses, via the pacemaker lead, cardiac electrical activity of the cardiovascular system of the subject that is generated in response to the pace signal and electrically coupled into the pacemaker lead and generates a digital signal that is representative of the cardiac electrical activity of the cardiovascular system of the subject that is sensed via the pacemaker lead. The DSC provides digital information to one or more processing modules that includes and/or is coupled to memory and that provide the reference signal to the DSC.

20 Claims, 49 Drawing Sheets

(56) References Cited

U.S. PATENT DOCUMENTS

| | | |
|---|---|---|
| 8,625,726 B2 | 1/2014 | Kuan |
| 9,174,057 B1 | 11/2015 | Fischell et al. |
| 9,201,547 B2 | 12/2015 | Elias |
| 2006/0235289 A1 | 10/2006 | Wesselink et al. |
| 2013/0278447 A1 | 10/2013 | Kremin |
| 2016/0015286 A1 | 1/2016 | Gitlin et al. |
| 2016/0188049 A1 | 6/2016 | Yang et al. |
| 2018/0126174 A1 | 5/2018 | Juffer et al. |
| 2018/0140848 A1 | 5/2018 | Stahmann |

OTHER PUBLICATIONS

Brian Pisani, "Digital Filter Types in Delta-Sigma ADCs", Application Report SBAA230, May 2017, pp. 1-8, Texas Instruments Incorporated, Dallas, Texas.

International Searching Authority; International Search Report and Written Opinion; International Application No. PCT/US2021/035420; dated Sep. 16, 2021; 7 pgs.

computing device 14 computing device 18

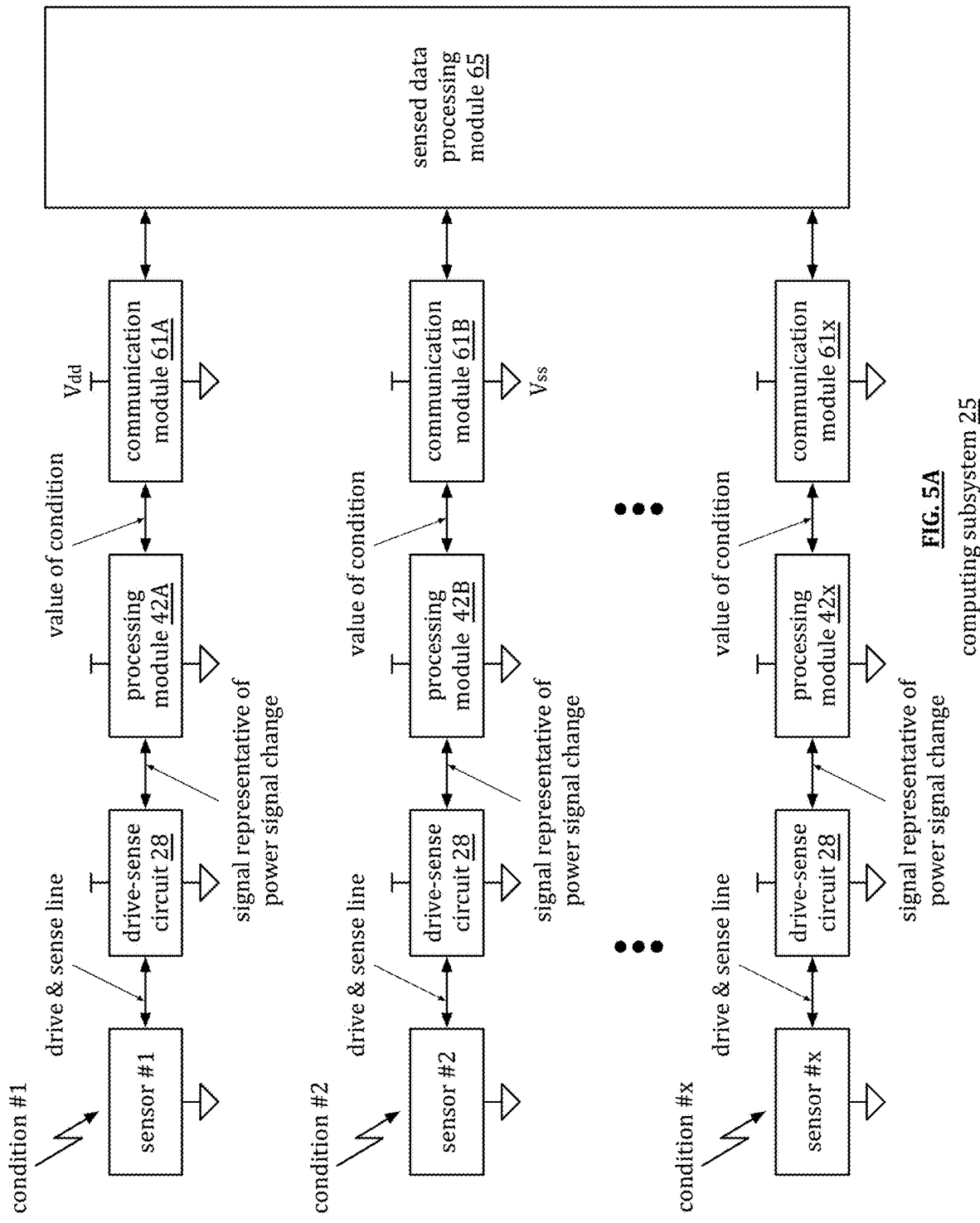

computing subsystem 25 computing subsystem 25

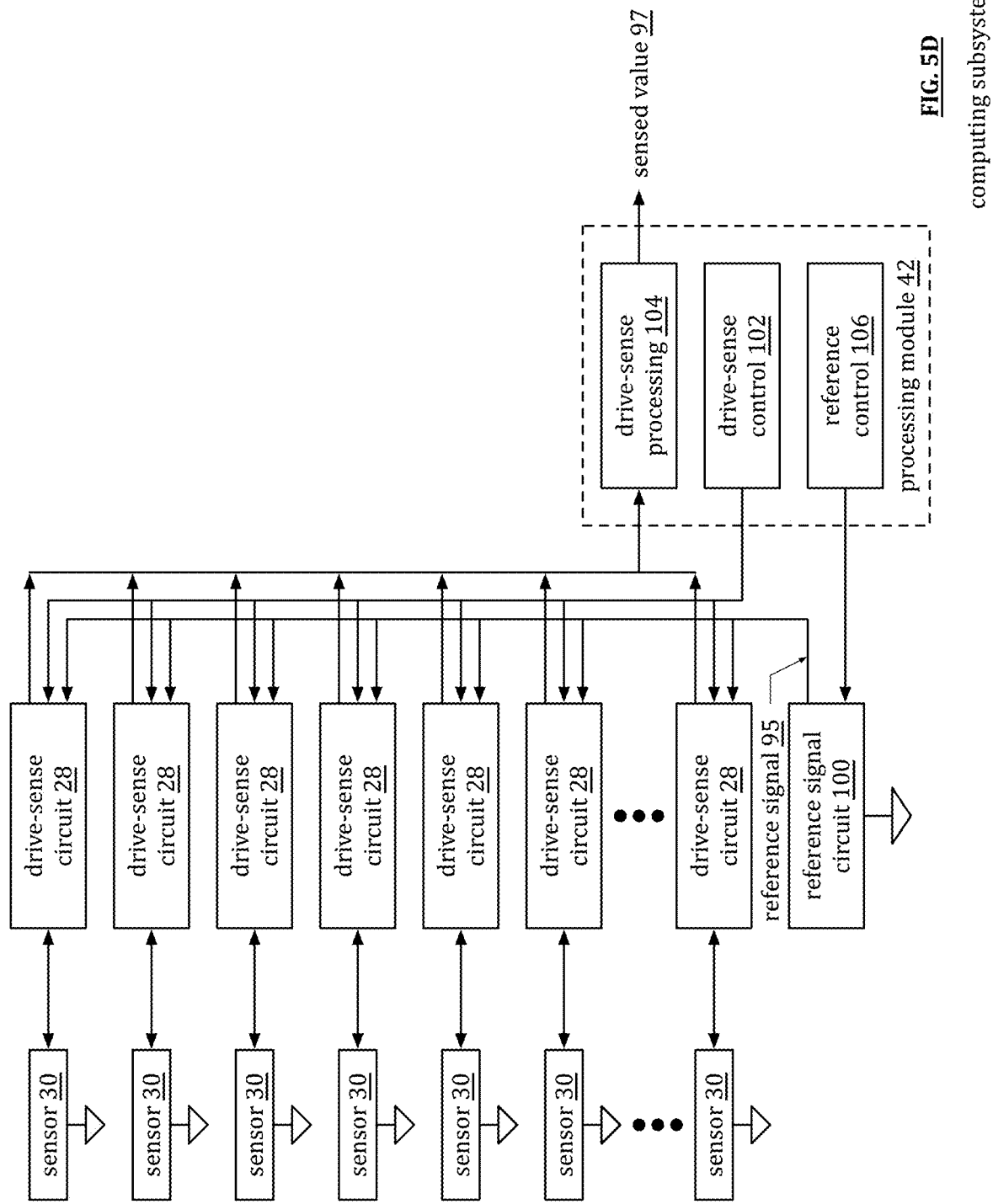

computing subsystem 25

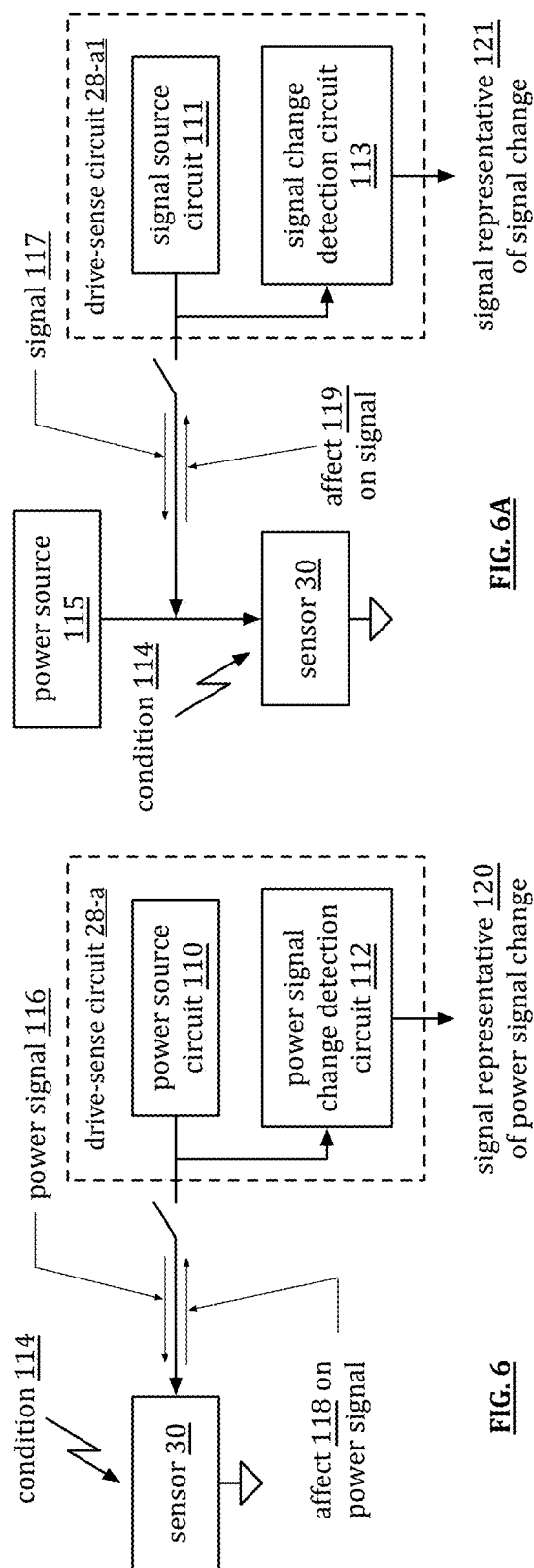
FIG. 6A
FIG. 6
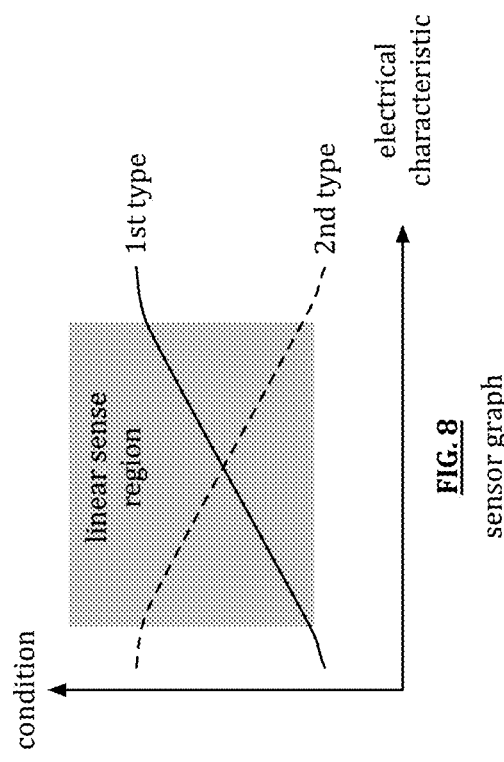
FIG. 8
sensor graph
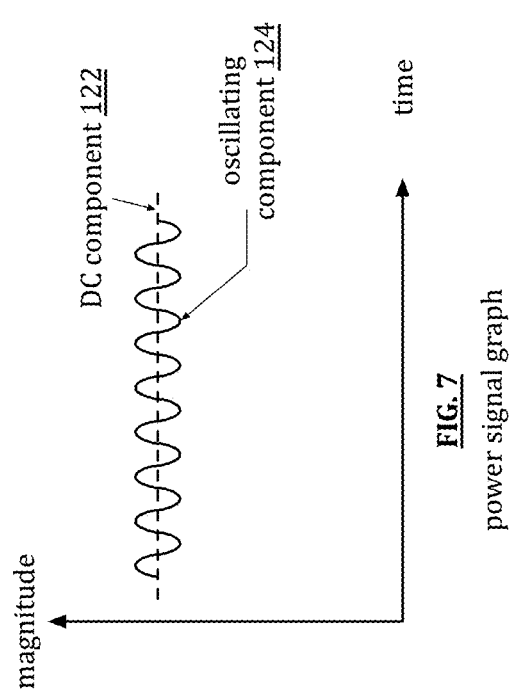
FIG. 7
power signal graph power signal graph power signal graph power signal graph power signal graph

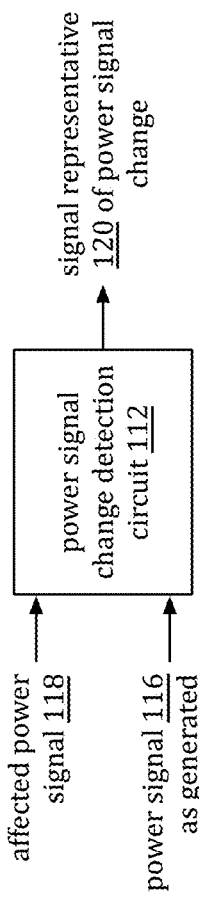
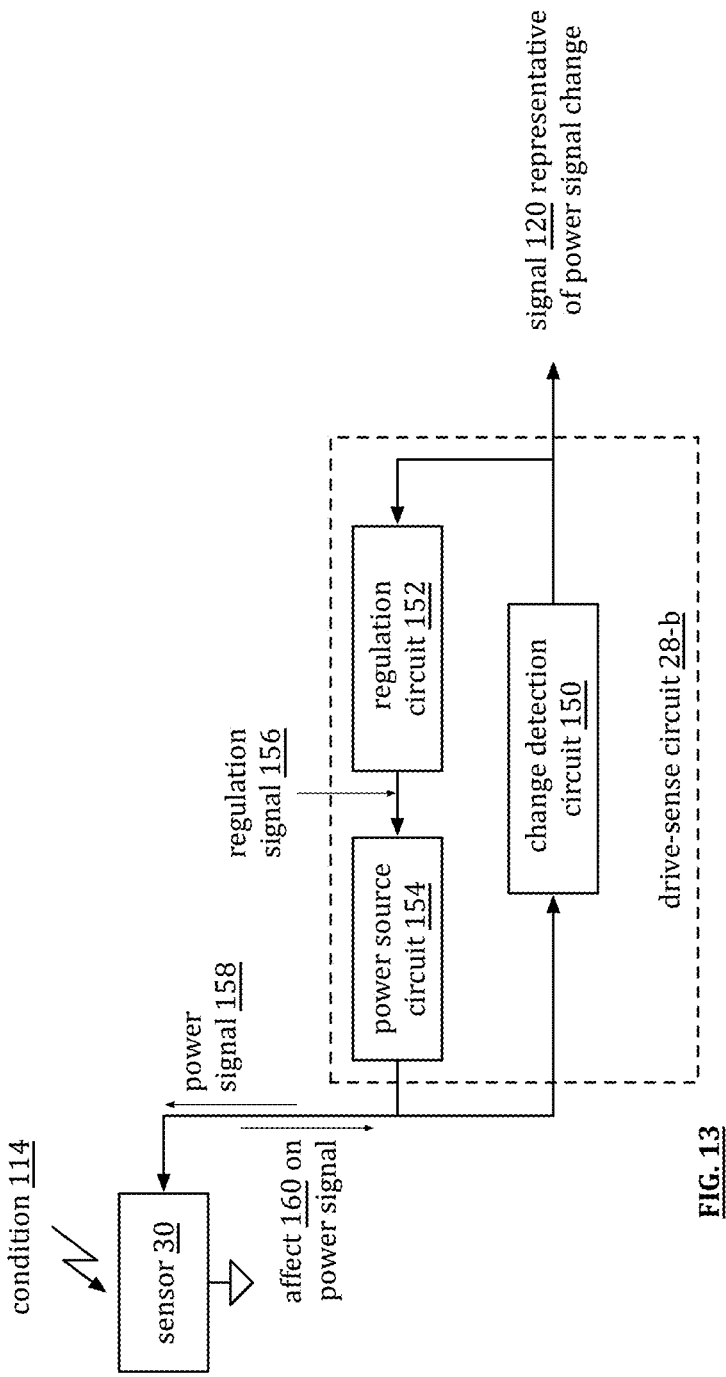

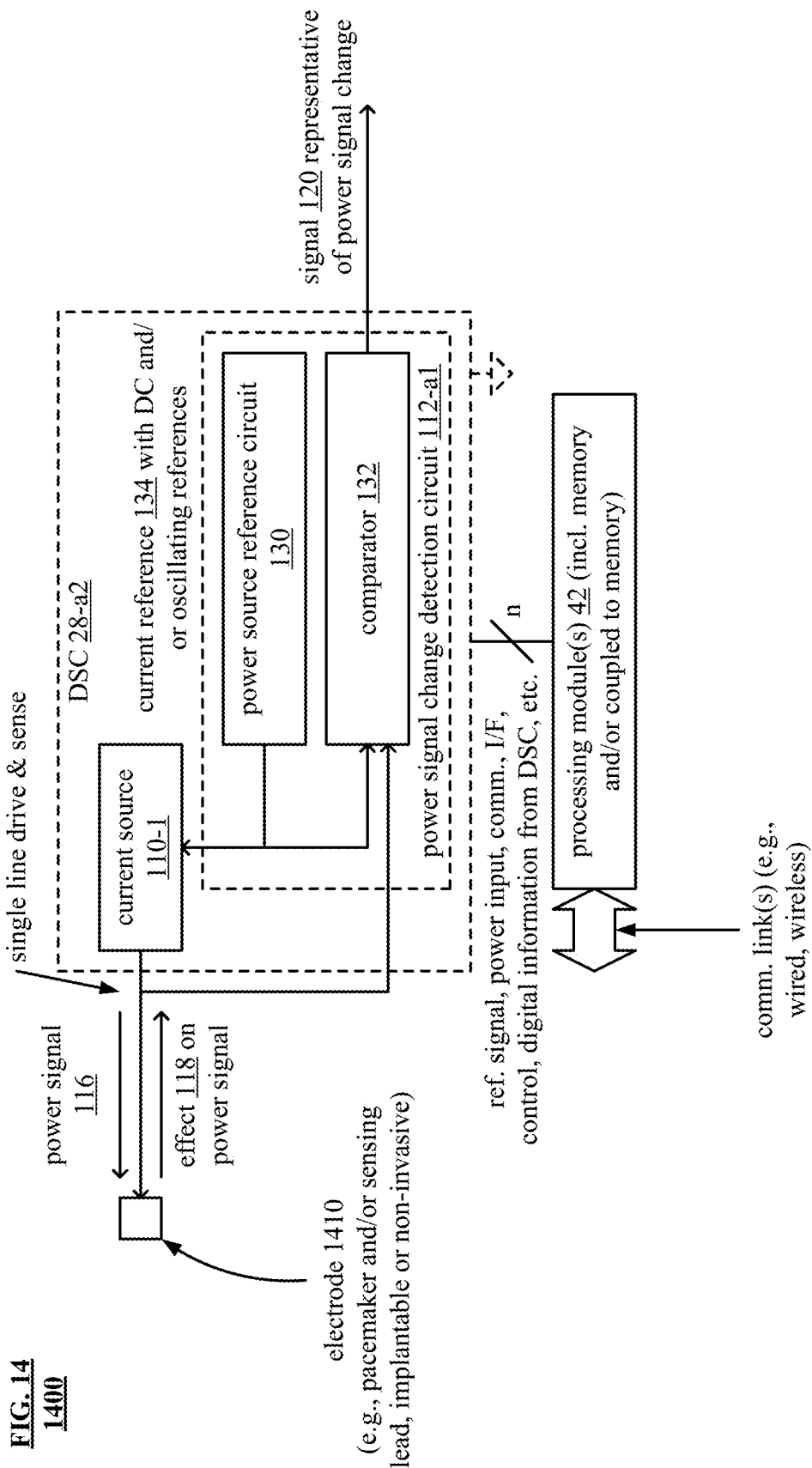

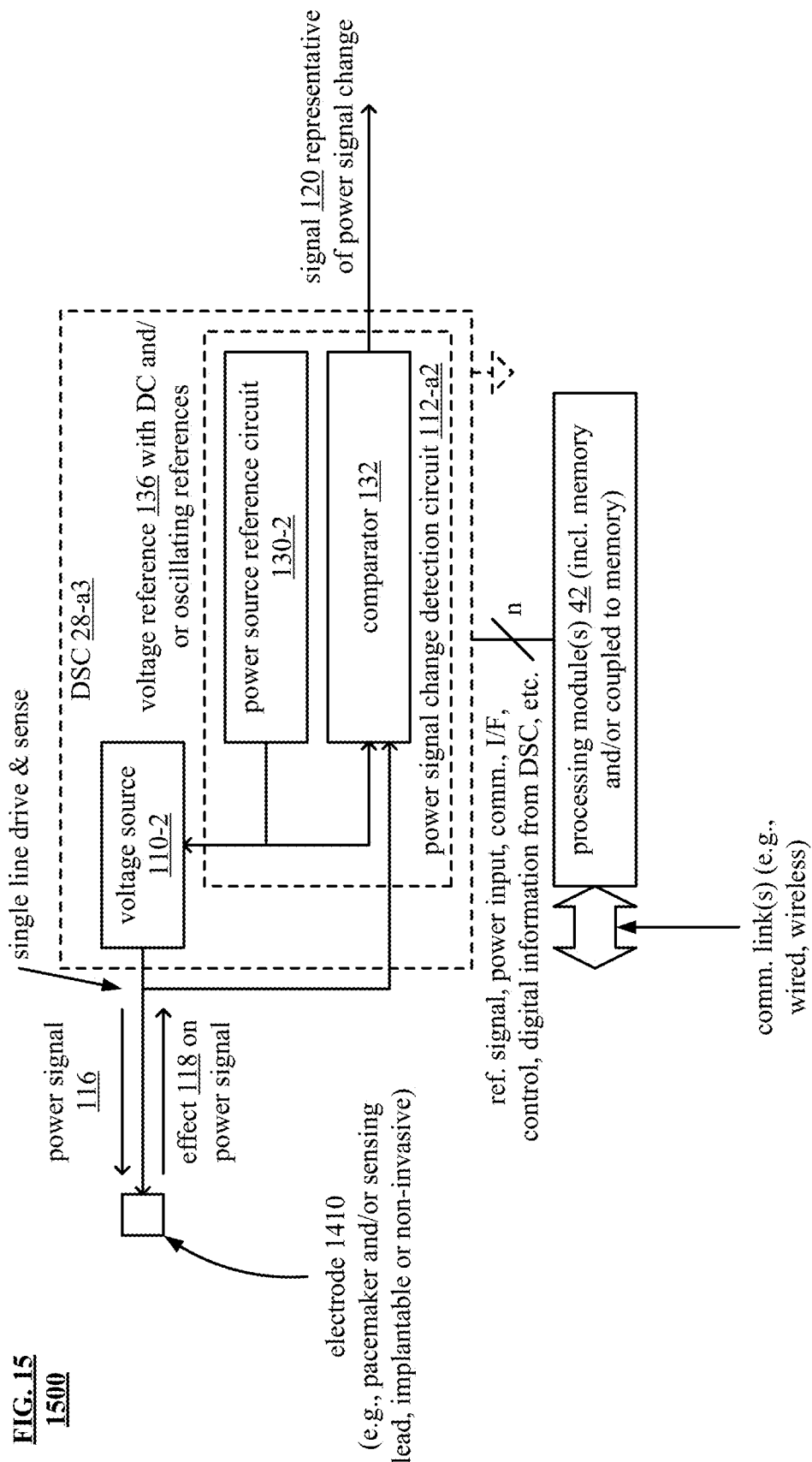

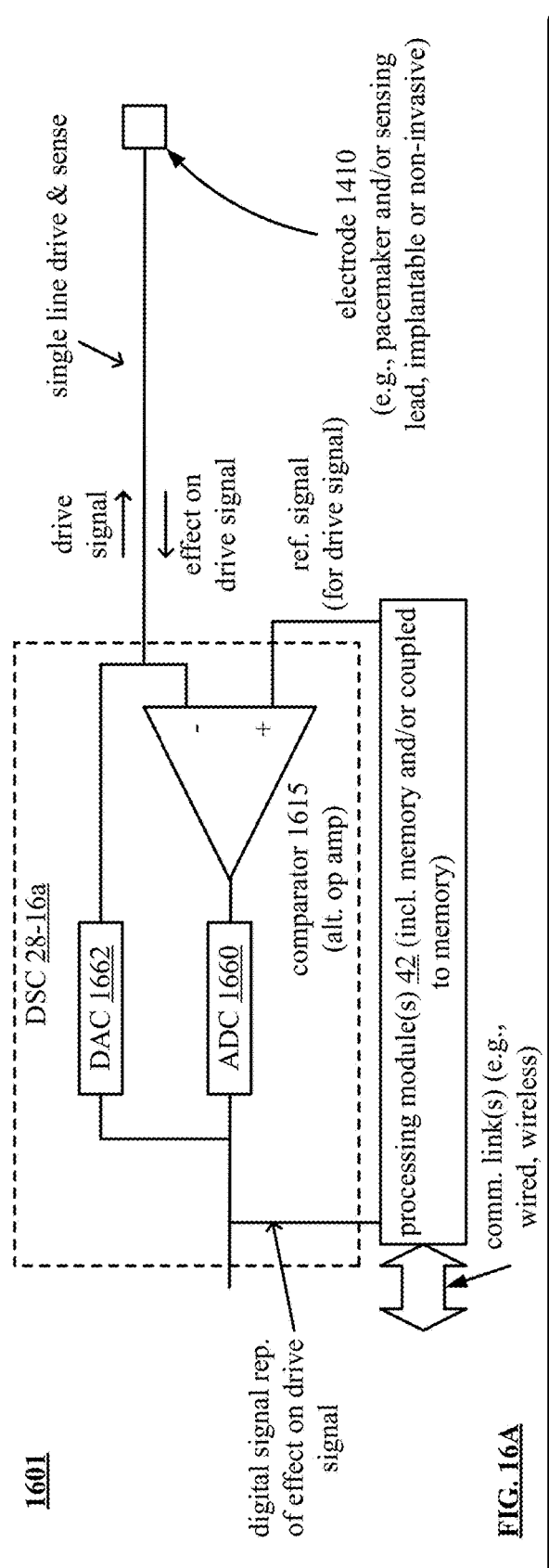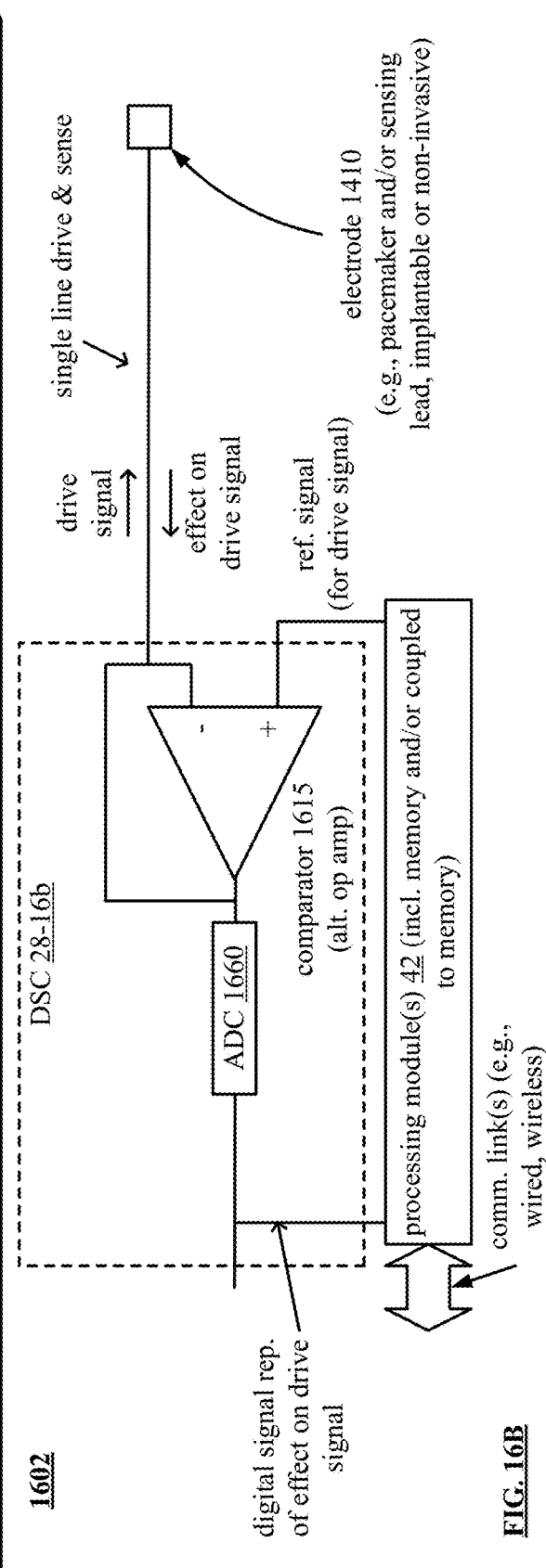
FIG. 16A
FIG. 16B

1900

2000

2101

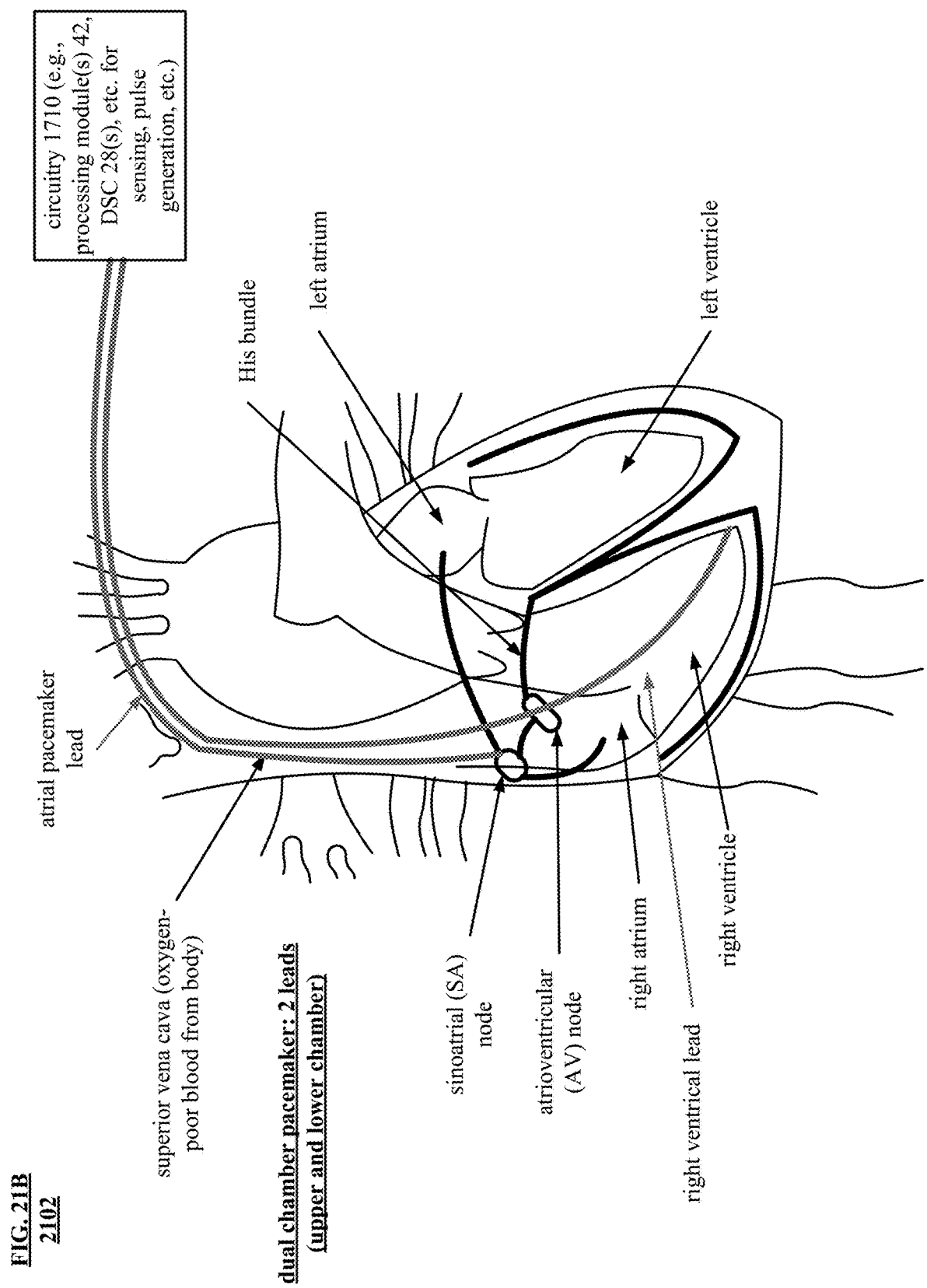

(start/continue)

operating a drive-sense circuit (DSC), operably coupled to a pacemaker lead, to receive a reference signal and to generate a pace signal including electrical impulses based on the reference signal 2110

> the pacemaker lead is implanted in of proximity to a sinoatrial (SA) node or a ventricle of a cardiovascular system of a subject 2112

> the pacemaker lead is implanted in of proximity to a ventricle of a cardiovascular system of a subject 2114 operating the DSC to provide the pace signal from the DSC via the pacemaker lead to an electrically responsive portion of a cardiac conductive system of the subject to facilitate cardiac operation of the cardiovascular system of the subject, wherein muscles of a heart of the subject produce a mechanical response to the electrical impulses of the pace signal to move blood through the cardiovascular system of the subject 2120 operating the DSC to sense, via the pacemaker lead, cardiac electrical activity of the cardiovascular system of the subject that is generated in response to the pace signal 2130 generating a digital signal that is representative of the cardiac electrical activity of the cardiovascular system of the subject that is sensed via the pacemaker lead 2140 processing the digital signal generated by the DSC to determine the cardiac electrical activity of the cardiovascular system of the subject that is sensed via the pacemaker lead 2150

(end/continue)

FIG. 23A
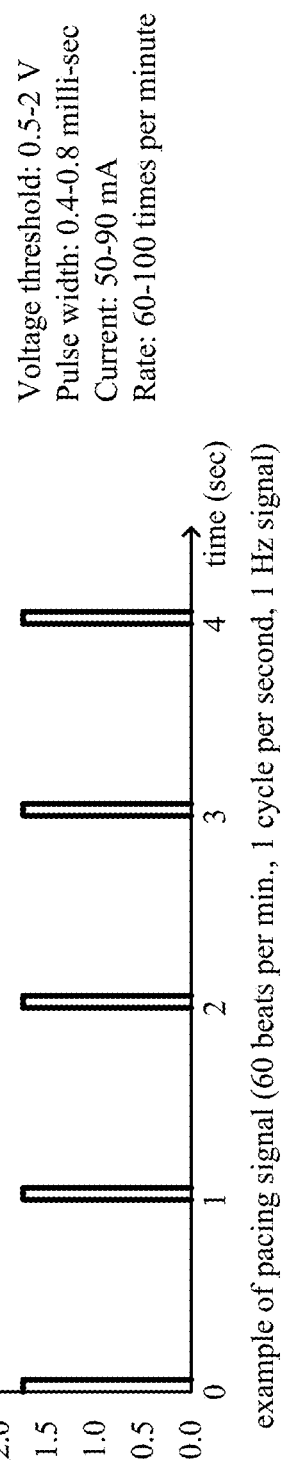
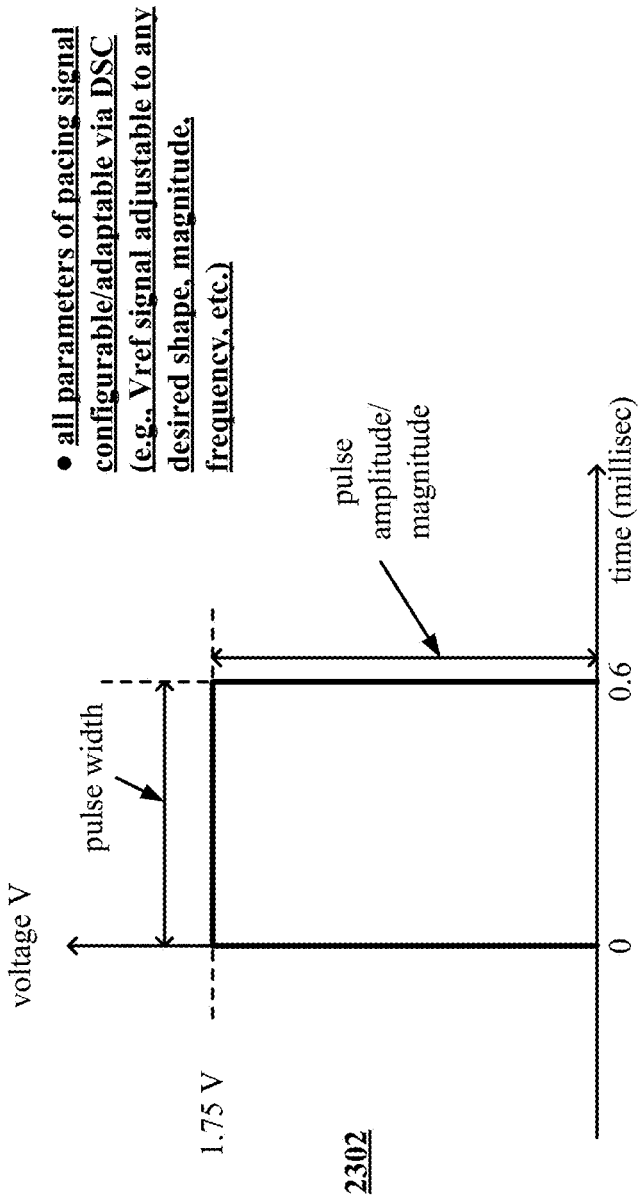

FIG. 23B
common ranges of pacing impulse signals for electrical capture:
Voltage threshold: 0.5-2 V
Pulse width: 0.4-0.8 milli-sec
Current: 50-90 mA
Rate: 60-100 times per minute
- all parameters of pacing signal configurable/adaptable via DSC (e.g., Vref signal adjustable to any desired shape, magnitude, frequency, etc.)
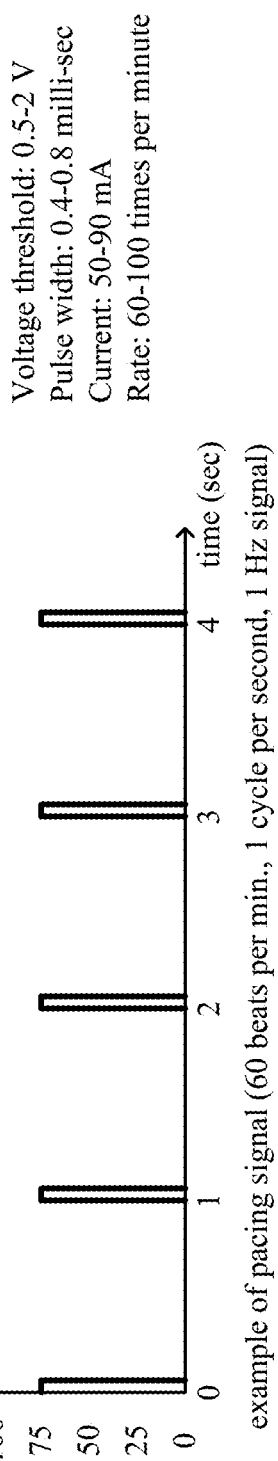
2303
example of pacing signal (60 beats per min., 1 cycle per second, 1 Hz signal)
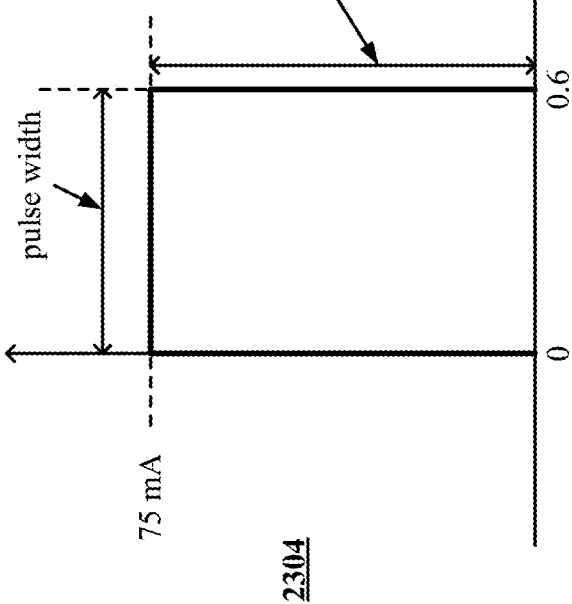
2304

2401

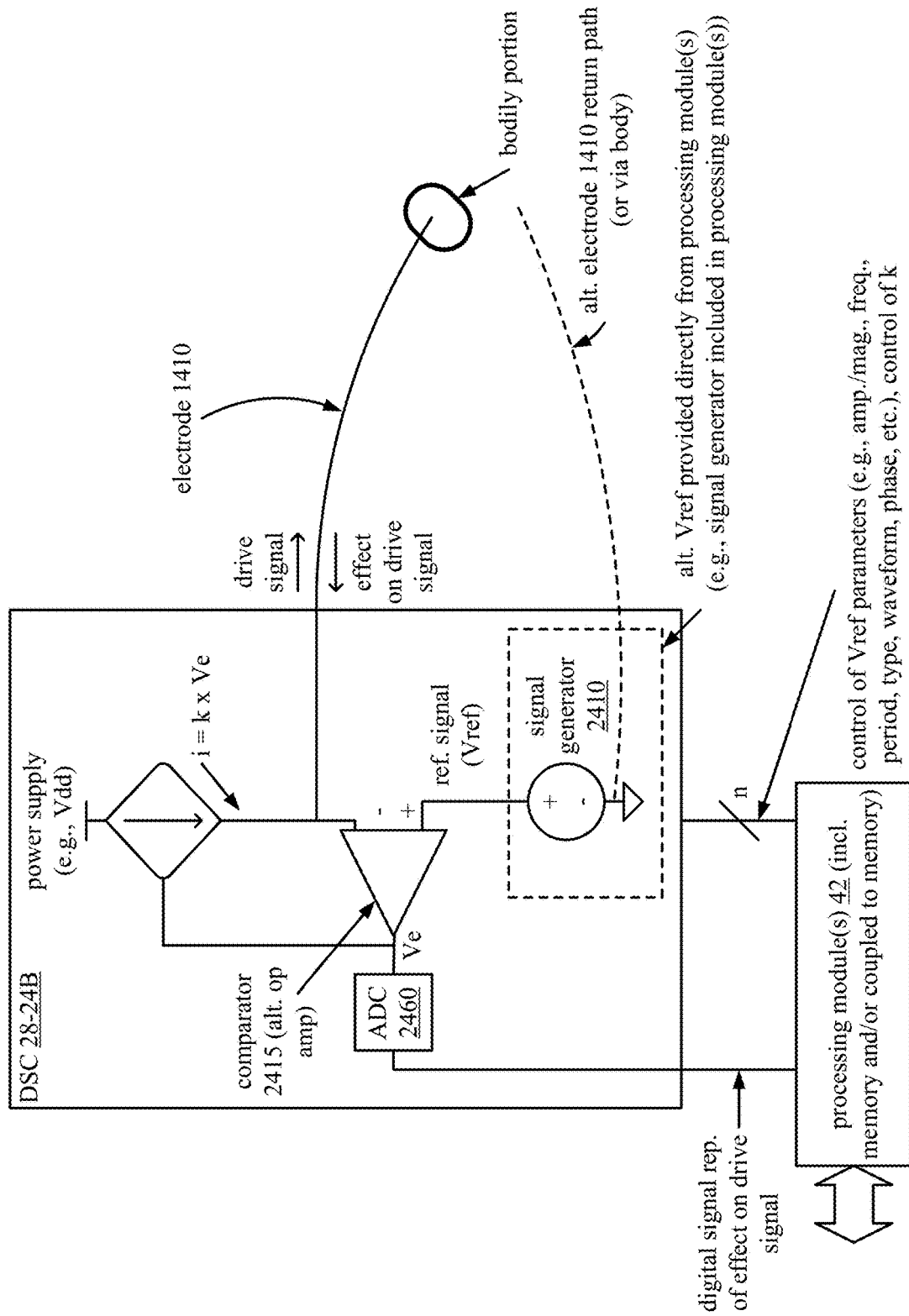

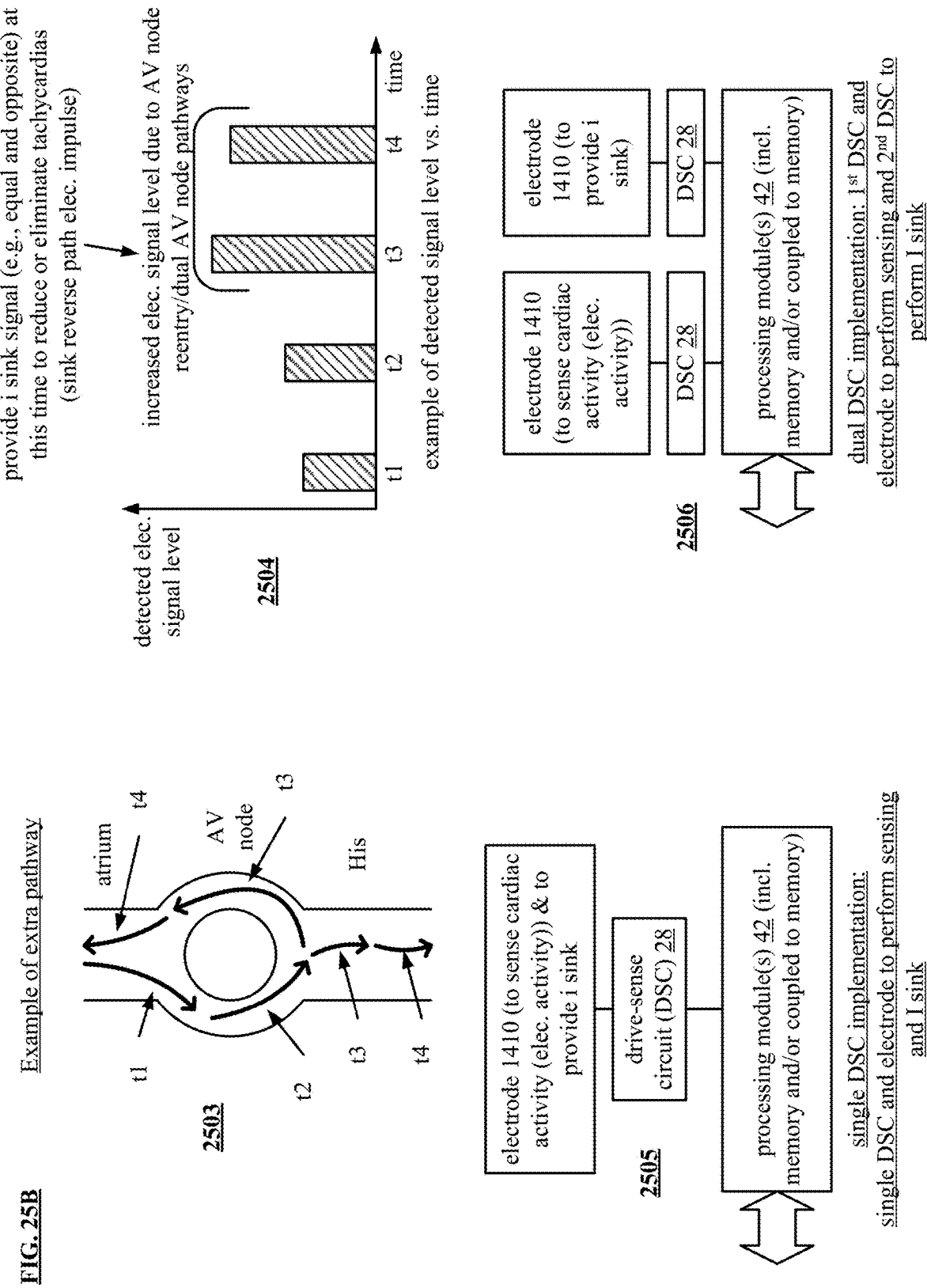

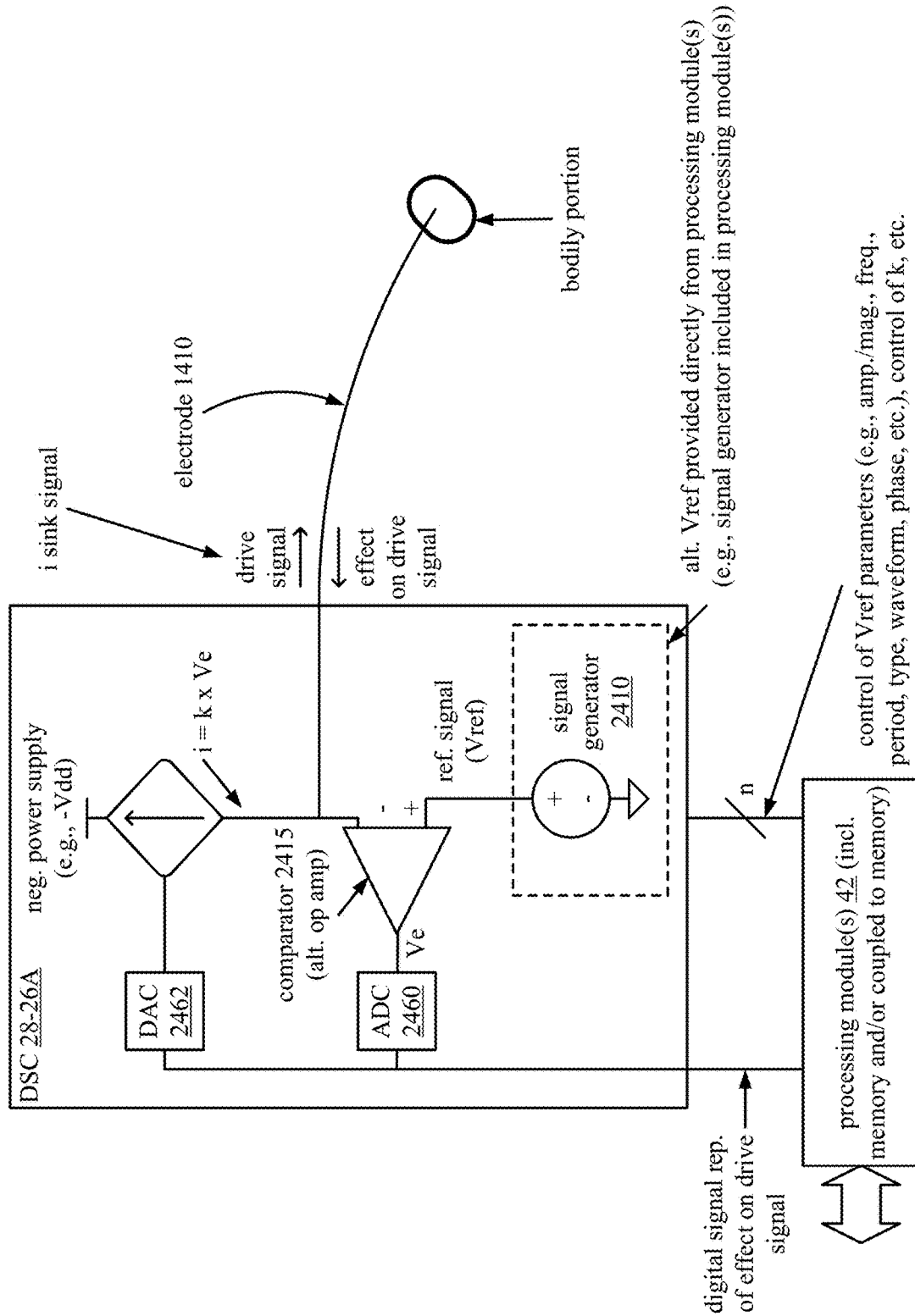

2602

2701

2702

2801

2802

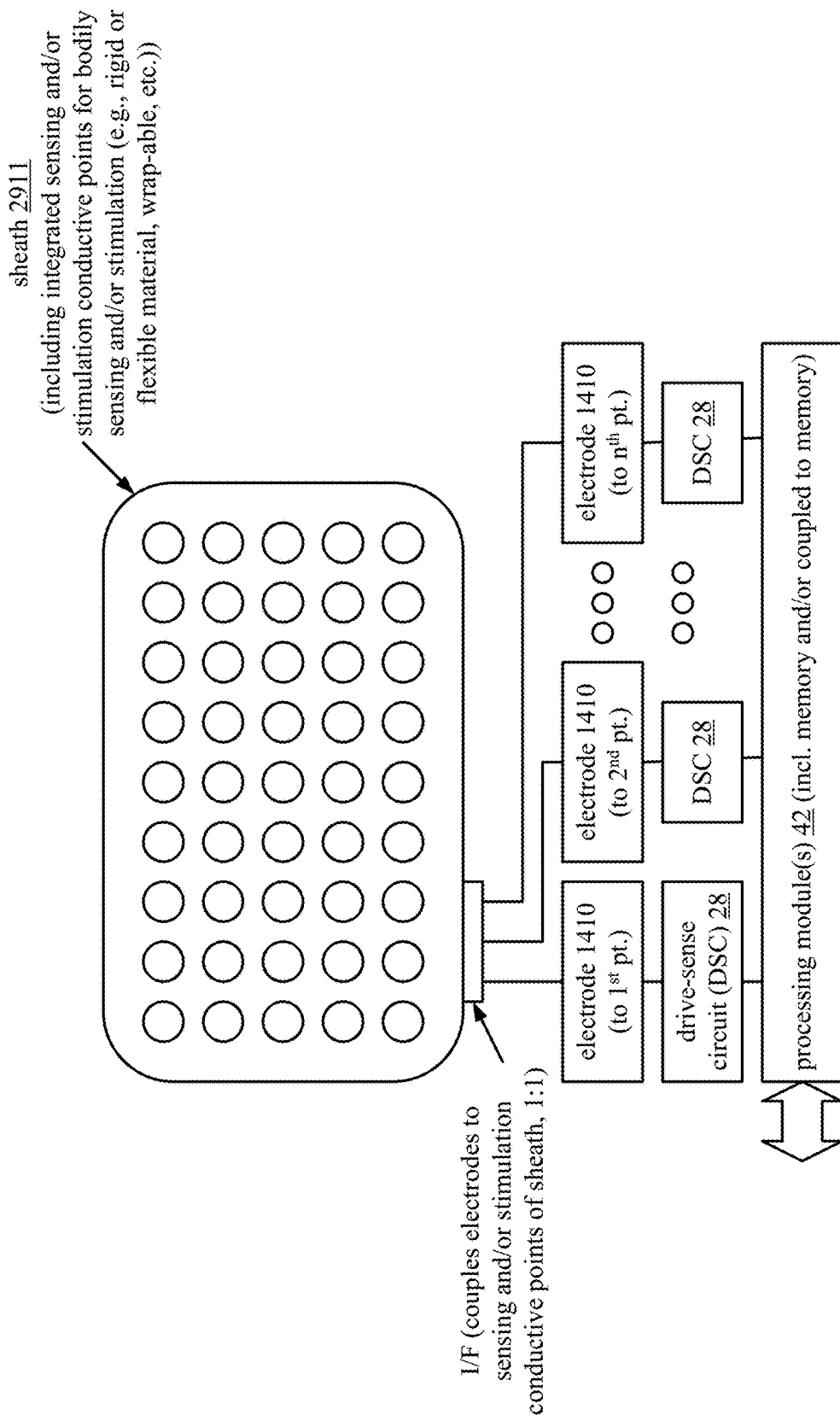

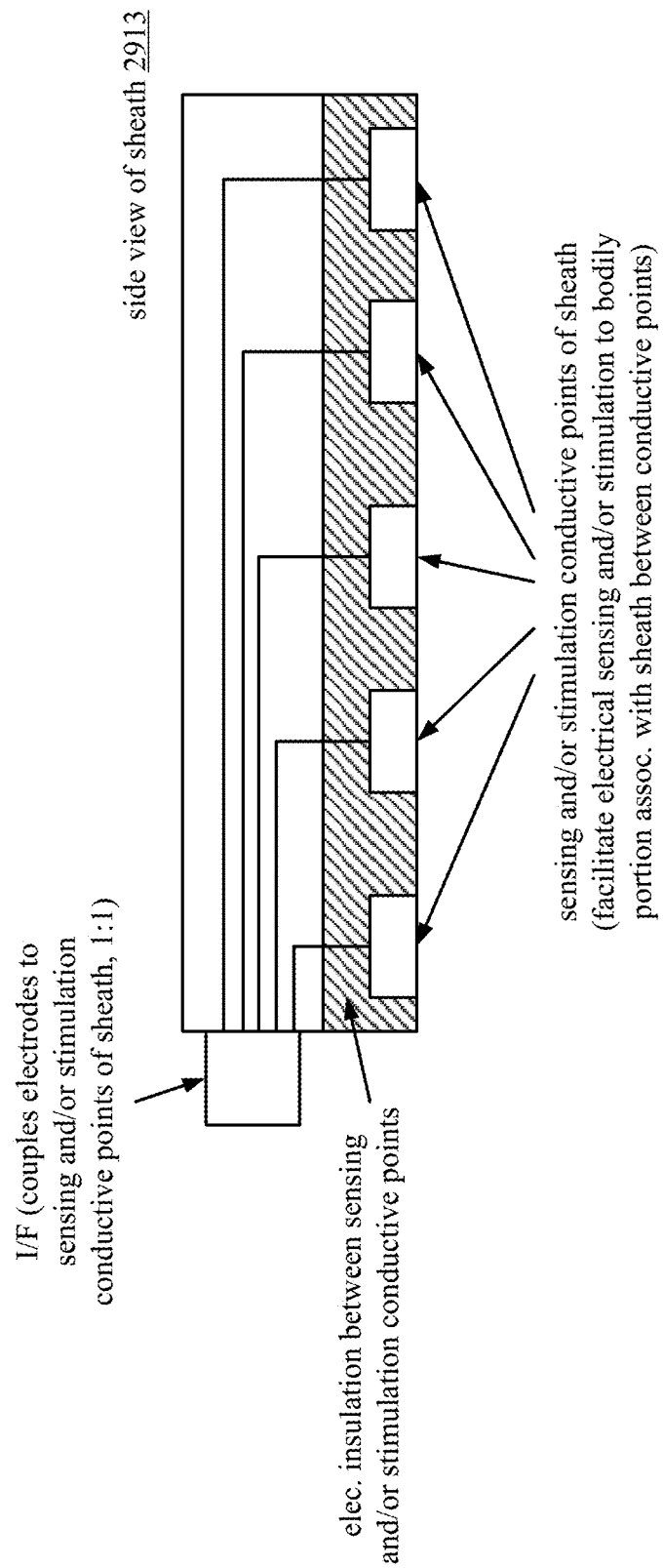

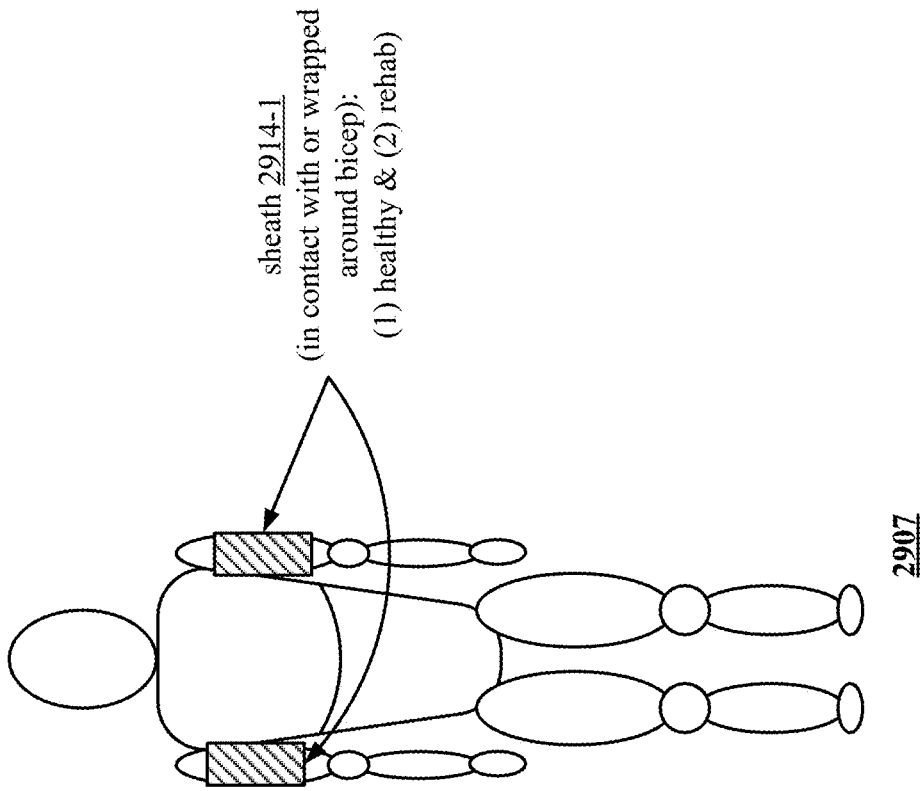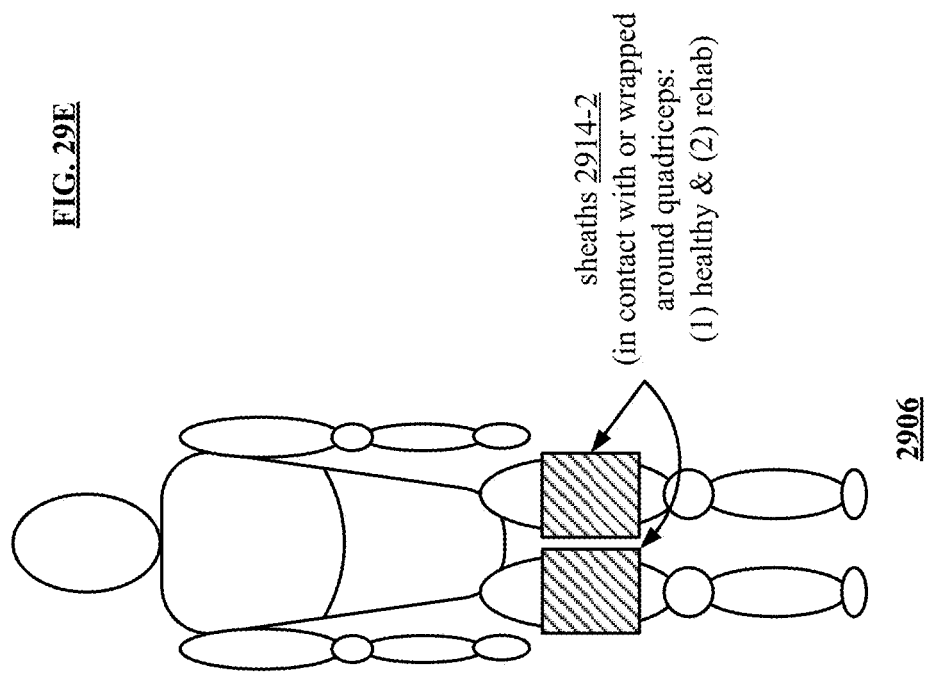
FIG. 29E

2908

2909

3000

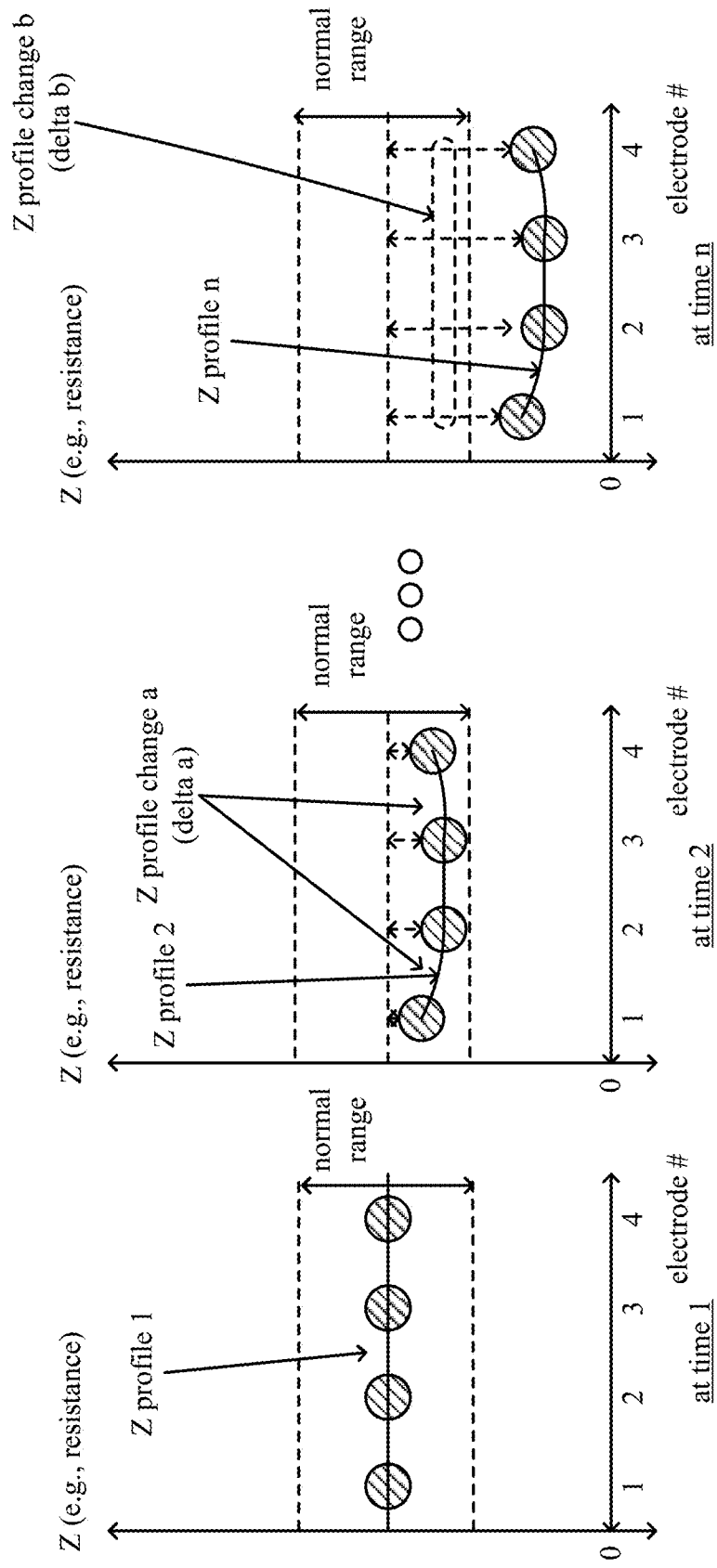

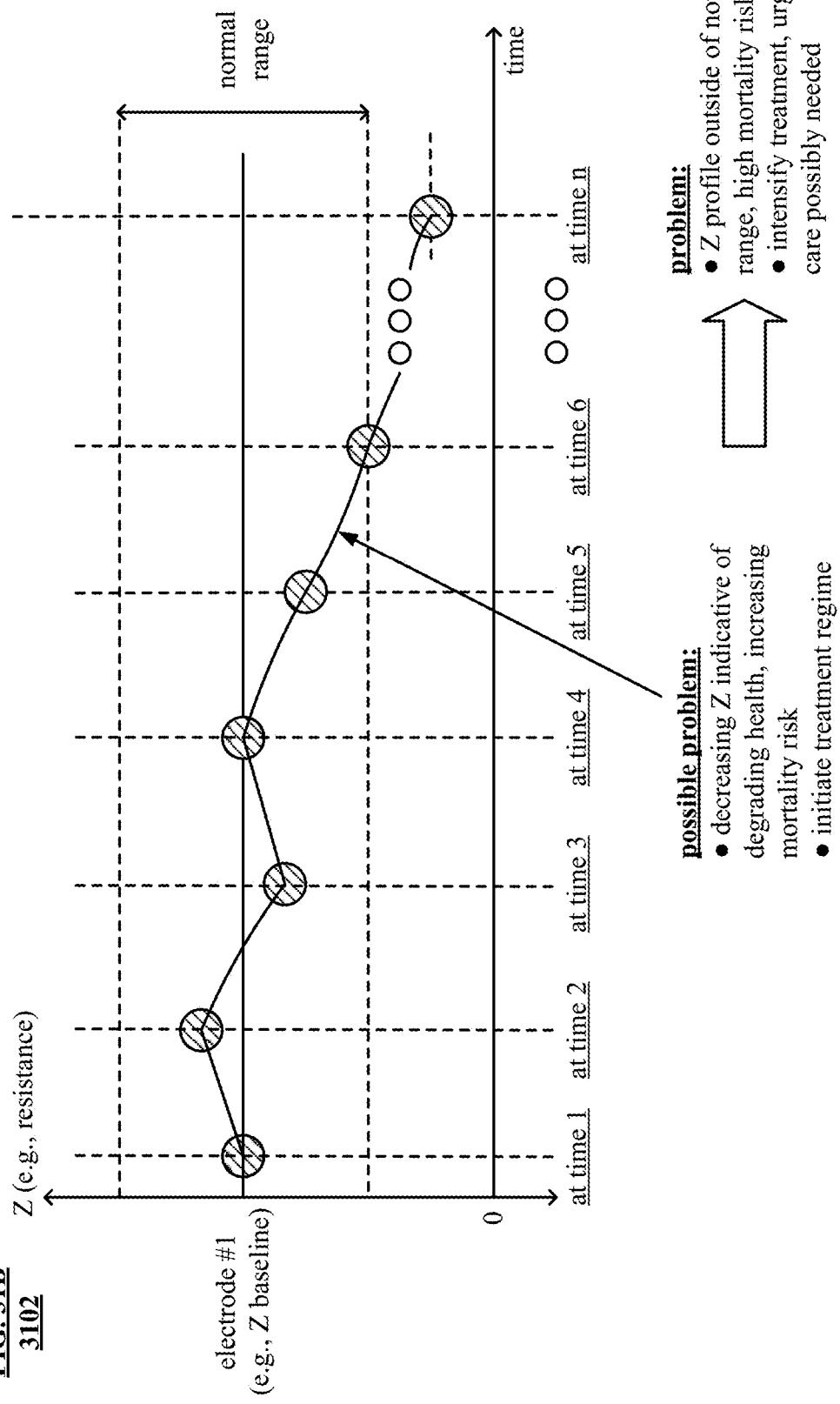

3200

3300

CURRENT SOURCE DRIVE-SENSE CIRCUIT (DSC) SERVICED PACEMAKER

CROSS REFERENCE TO RELATED PATENTS/PATENT APPLICATIONS

The present U.S. Utility Patent Application claims priority pursuant to 35 U.S.C. § 120 as a continuation of U.S. Utility application Ser. No. 16/891,543 entitled "Pacemaker operative to deliver impulses of pace signal and sense cardiac response via single conductor of pacemaker lead," filed Jun. 3, 2020, pending, which is hereby incorporated herein by reference in its entirety and made part of the present U.S. Utility Patent Application for all purposes.

INCORPORATION BY REFERENCE

The U.S. Utility application Ser. No. 16/891,591, entitled "Array operative to perform distributed/patterned sensing and/or stimulation across patient bodily section," filed Jun. 3, 2020, pending, is hereby incorporated herein by reference in its entirety and made part of the present U.S. Utility Patent Application for all purposes.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

Technical Field of the Invention

This invention relates generally to data communication systems and more particularly to sensed data collection and/or communication including within medical and/or therapeutic related applications.

Description of Related Art

Sensors are used in a wide variety of applications ranging from in-home automation, to industrial systems, to health care, to transportation, and so on. For example, sensors are placed in bodies, automobiles, airplanes, boats, ships, trucks, motorcycles, cell phones, televisions, touch-screens, industrial plants, appliances, motors, checkout counters, etc. for the variety of applications.

In general, a sensor converts a physical quantity into an electrical or optical signal. For example, a sensor converts a physical phenomenon, such as a biological condition, a chemical condition, an electric condition, an electromagnetic condition, a temperature, a magnetic condition, mechanical motion (position, velocity, acceleration, force, pressure), an optical condition, and/or a radioactivity condition, into an electrical signal.

A sensor includes a transducer, which functions to convert one form of energy (e.g., force) into another form of energy (e.g., electrical signal). There are a variety of transducers to support the various applications of sensors. For example, a transducer is capacitor, a piezoelectric transducer, a piezoresistive transducer, a thermal transducer, a thermal-couple, a photoconductive transducer such as a photoresistor, a photodiode, and/or phototransistor.

A sensor circuit is coupled to a sensor to provide the sensor with power and to receive the signal representing the physical phenomenon from the sensor. The sensor circuit includes at least three electrical connections to the sensor: one for a power supply; another for a common voltage reference (e.g., ground); and a third for receiving the signal representing the physical phenomenon. The signal representing the physical phenomenon will vary from the power supply voltage to ground as the physical phenomenon changes from one extreme to another (for the range of sensing the physical phenomenon).

The sensor circuits provide the received sensor signals to one or more computing devices for processing. A computing device is known to communicate data, process data, and/or store data. The computing device may be a cellular phone, a laptop, a tablet, a personal computer (PC), a work station, a video game device, a server, and/or a data center that support millions of web searches, stock trades, or on-line purchases every hour.

The computing device processes the sensor signals for a variety of applications. For example, the computing device processes sensor signals to determine temperatures of a variety of items in a refrigerated truck during transit. As another example, the computing device processes the sensor signals to determine a touch on a touchscreen. As yet another example, the computing device processes the sensor signals to determine various data points in a production line of a product.

BRIEF DESCRIPTION OF THE SEVERAL VIEWS OF THE DRAWING(S)

FIG. 5A is a schematic plot diagram of a computing subsystem in accordance with the present invention;

FIG. 5D is a schematic block diagram of another embodiment of a computing subsystem in accordance with the present invention;

FIG. 6 is a schematic block diagram of a drive center circuit in accordance with the present invention;

FIG. 6A is a schematic block diagram of another embodiment of a drive sense circuit in accordance with the present invention;

FIG. 7 is an example of a power signal graph in accordance with the present invention;

FIG. 8 is an example of a sensor graph in accordance with the present invention;

FIG. 12 is a schematic block diagram of an embodiment of a power signal change detection circuit in accordance with the present invention;

FIG. 13 is a schematic block diagram of another embodiment of a drive-sense circuit in accordance with the present invention;

FIG. 14 is a schematic block diagram of an embodiment of a DSC that is interactive with an electrode in accordance with the present invention;

FIG. 15 is a schematic block diagram of another embodiment of a DSC that is interactive with an electrode in accordance with the present invention;

FIG. 16A is a schematic block diagram of another embodiment of a DSC configured simultaneously to drive and sense a drive signal to an electrode in accordance with the present invention;

FIG. 16B is a schematic block diagram of another embodiment of a DSC configured simultaneously to drive and sense a drive signal to an electrode in accordance with the present invention;

Figure 21A:
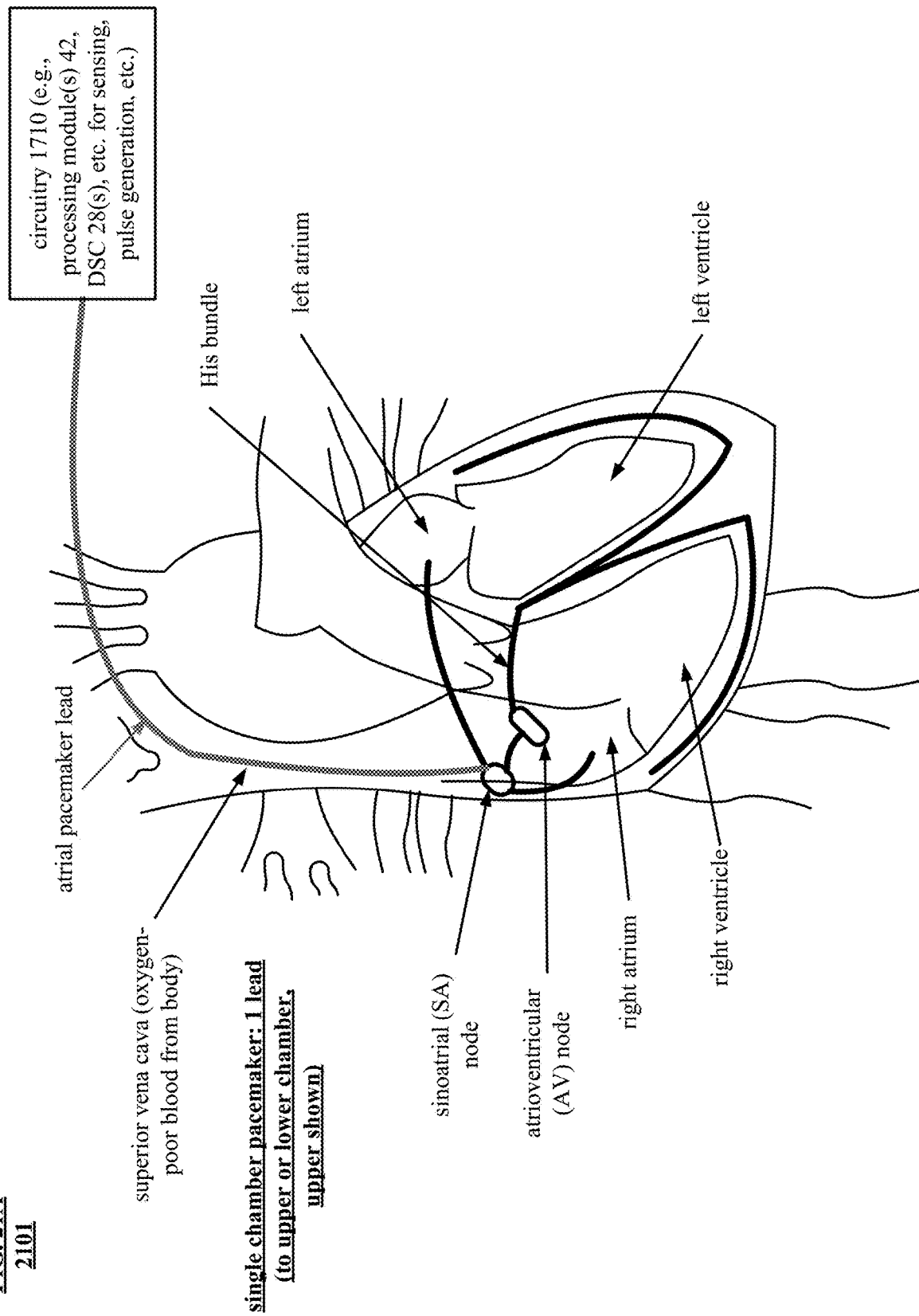
Figure 21C:
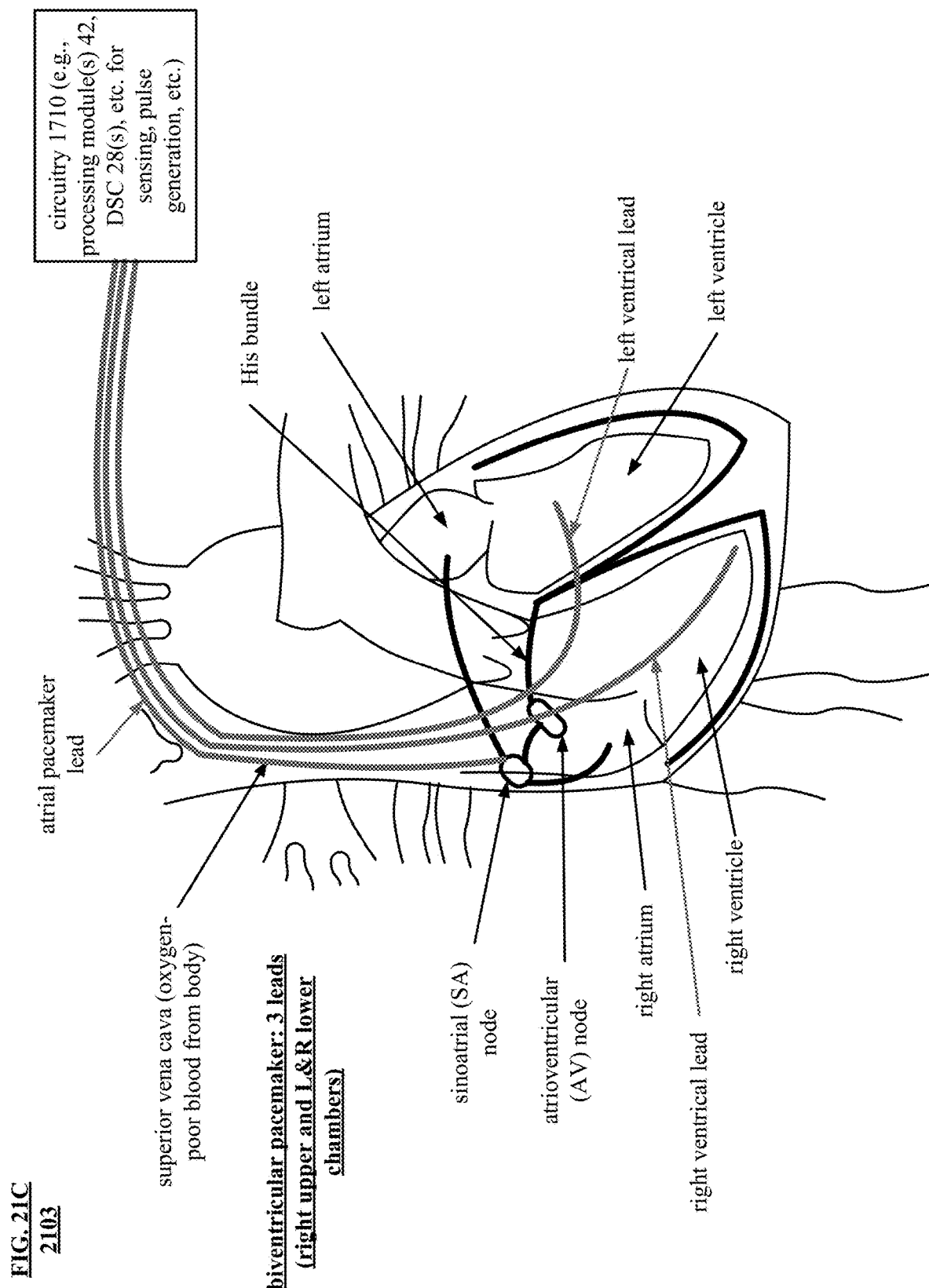
Figure 22:
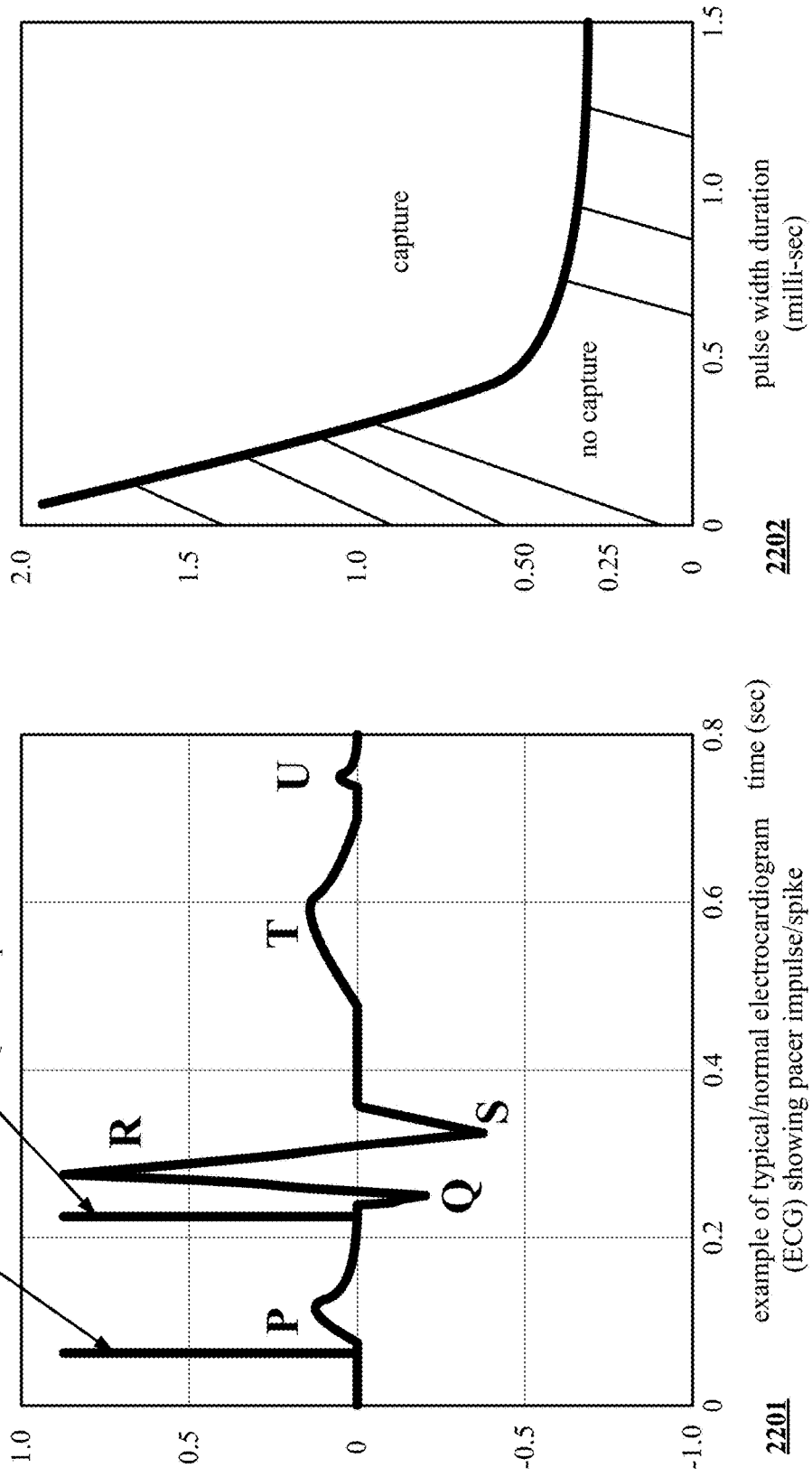
Figure 24A:
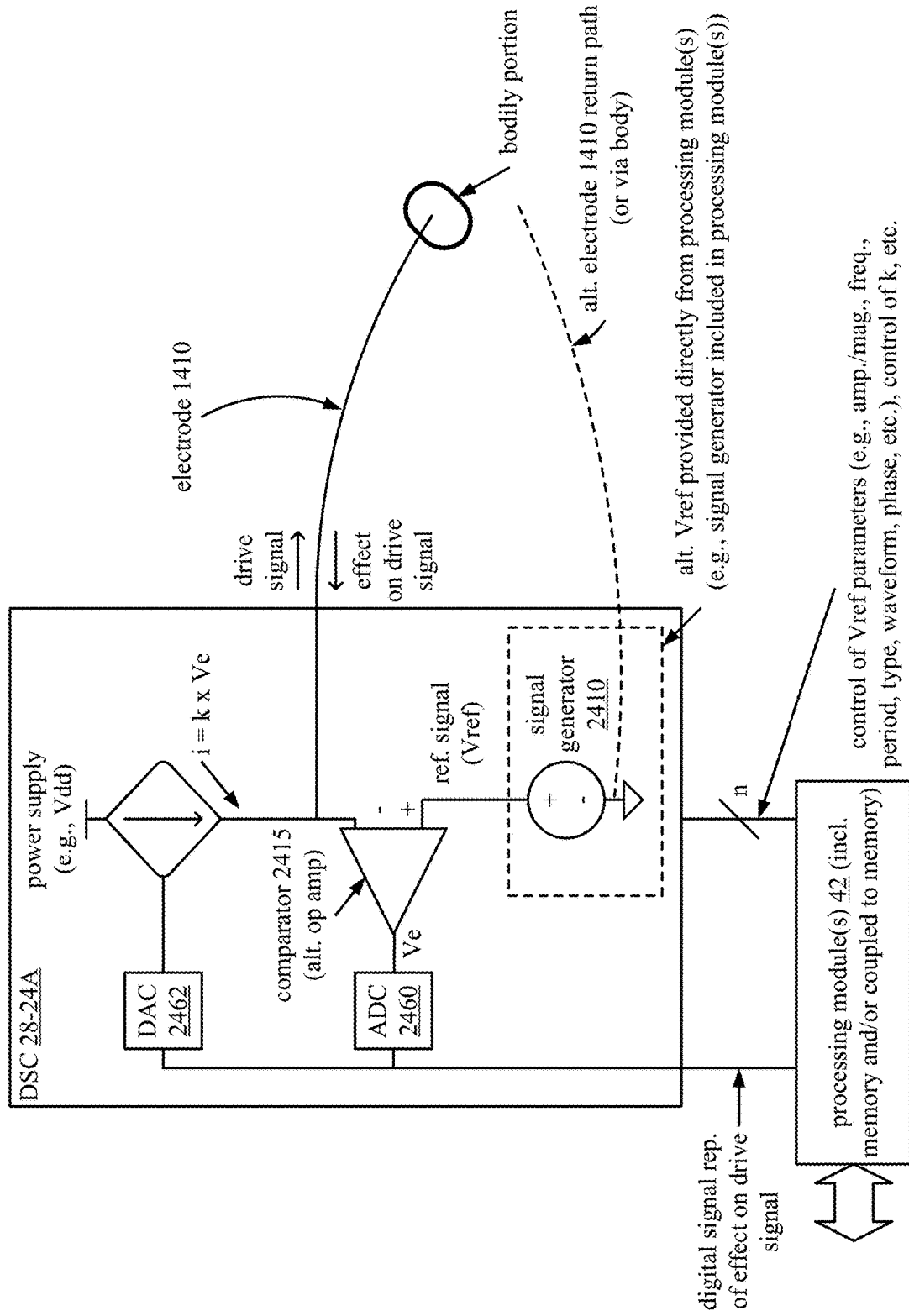
Figure 25A:
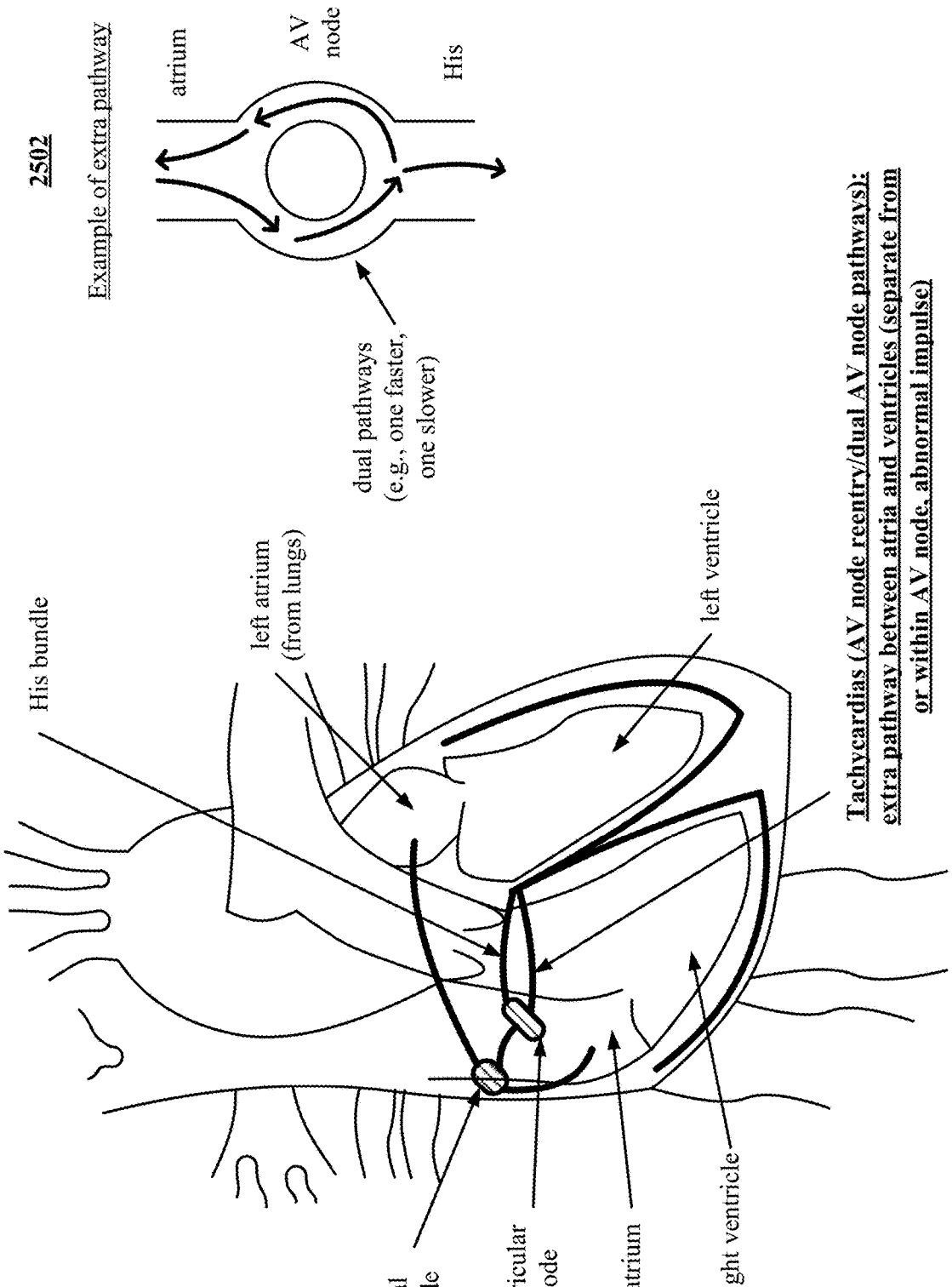
Figure 26B:
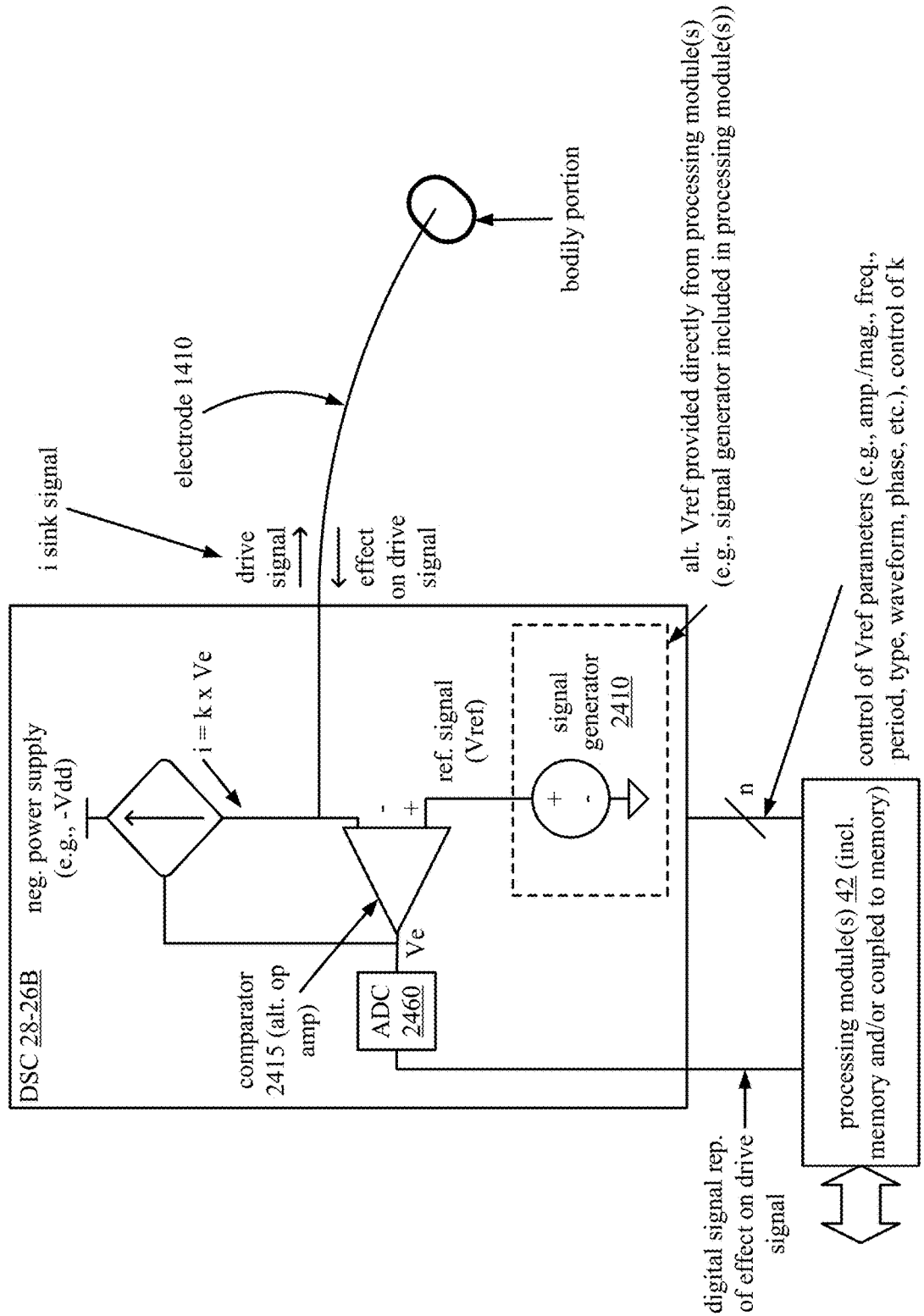
Figure 27A:
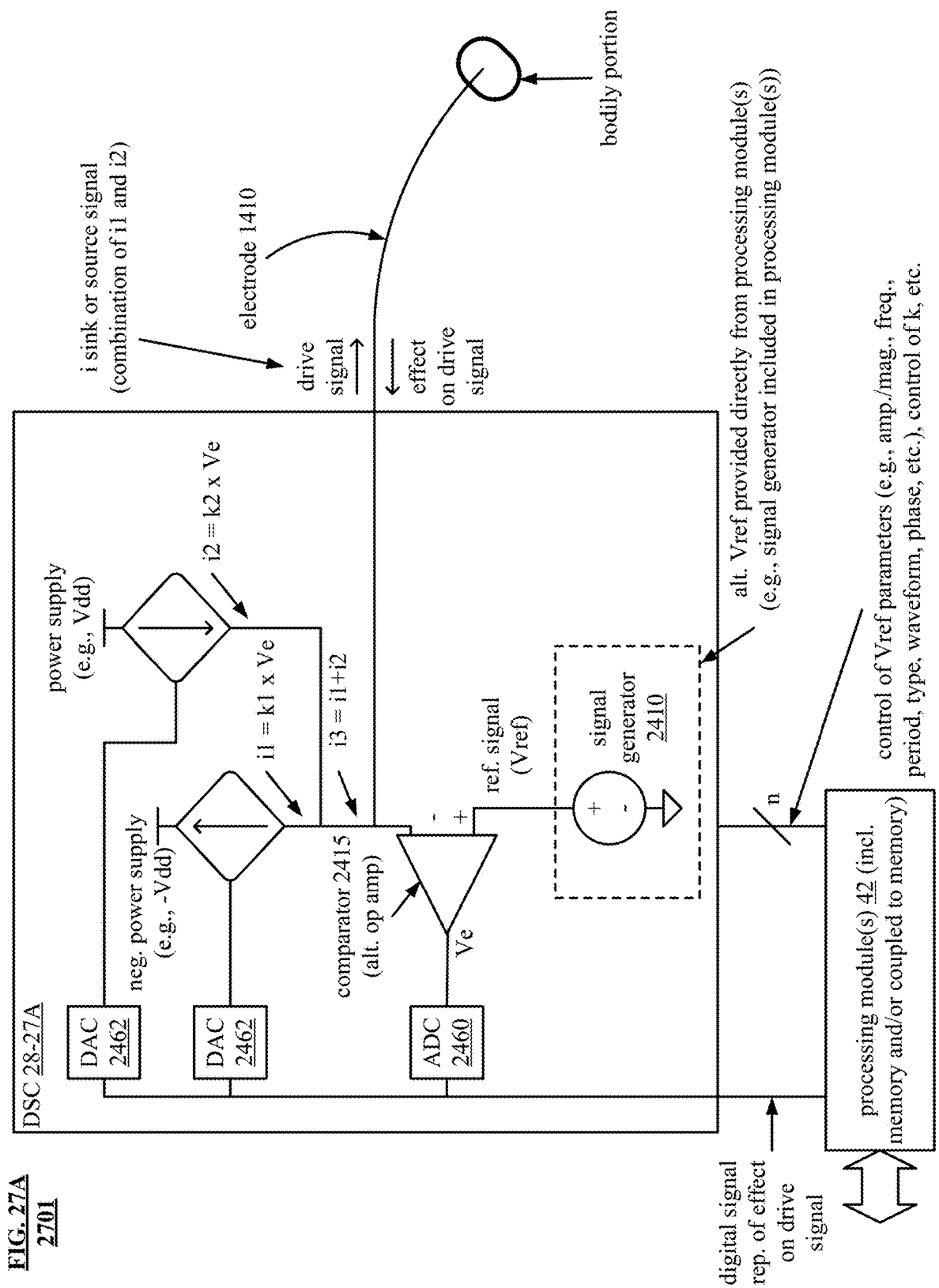
Figure 27B:
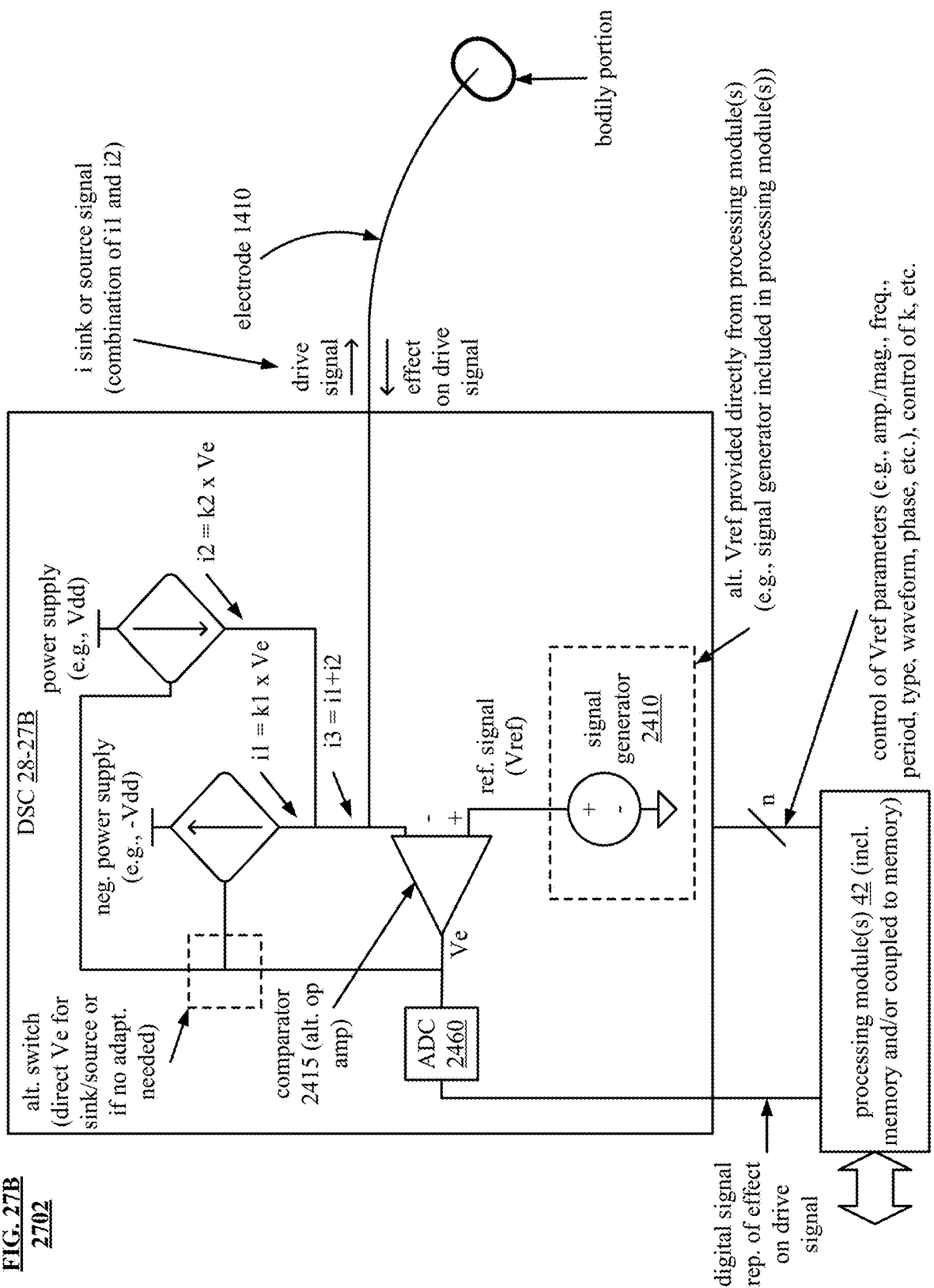
Figure 28A:
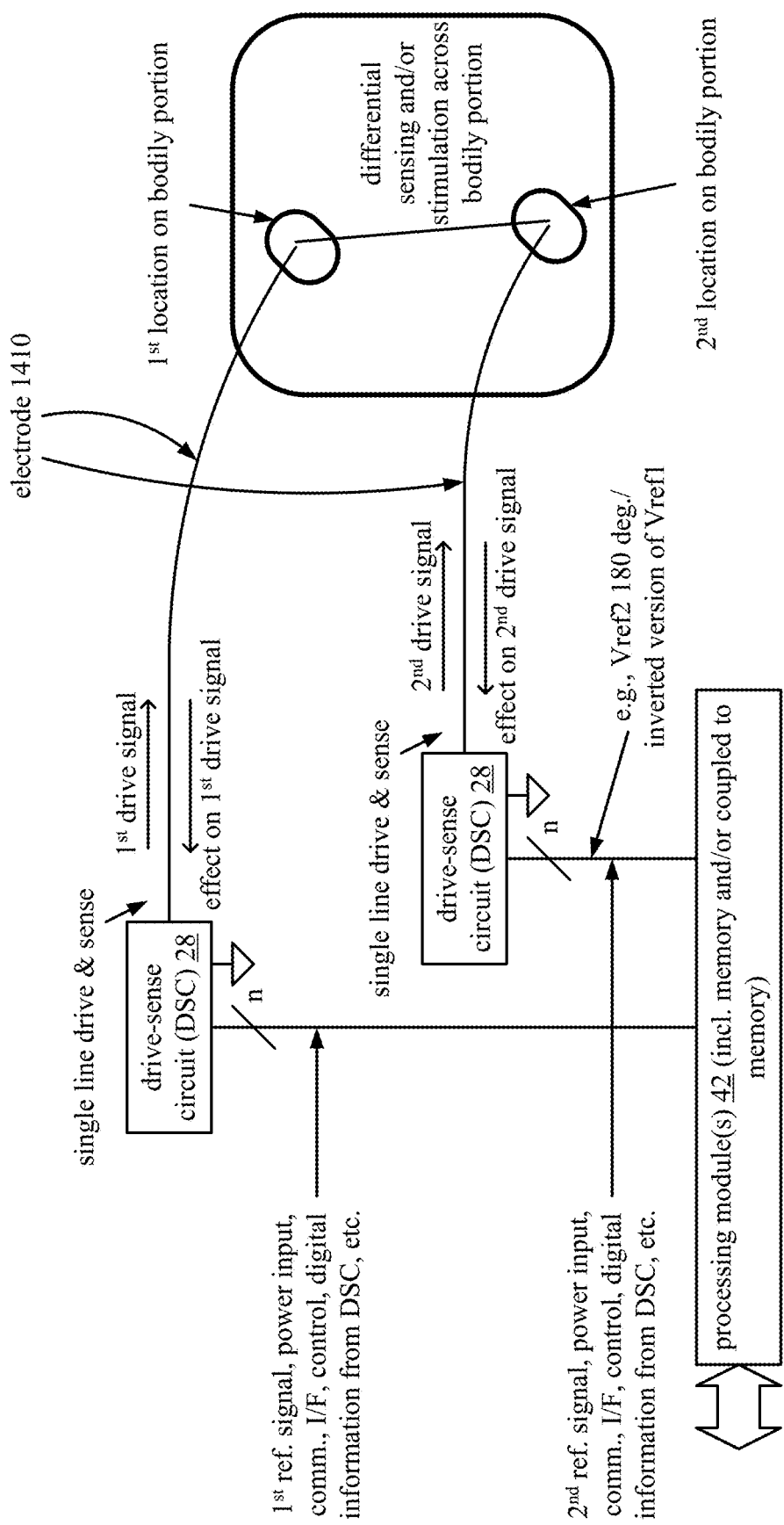
Figure 28B:
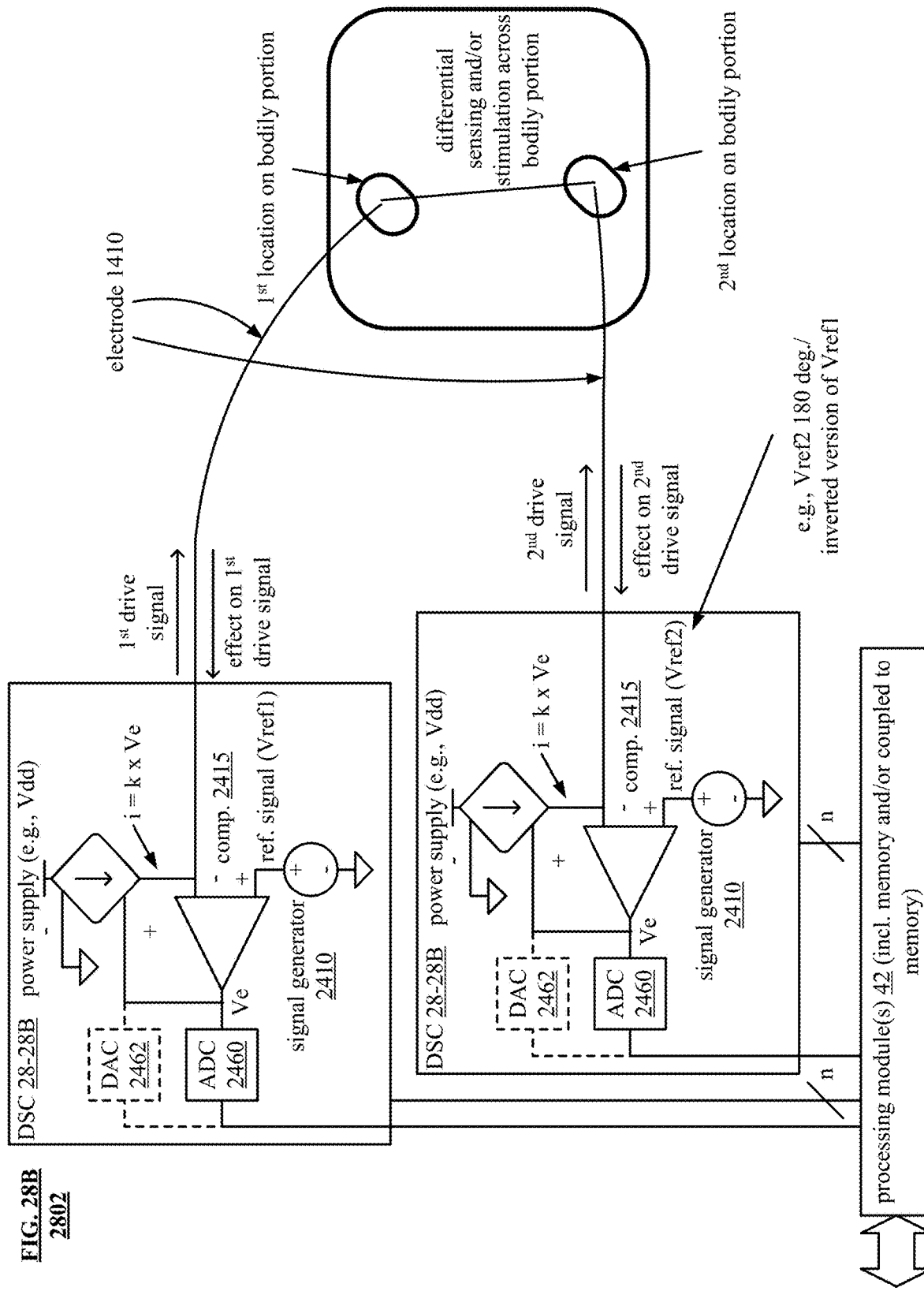
Figure 28C:
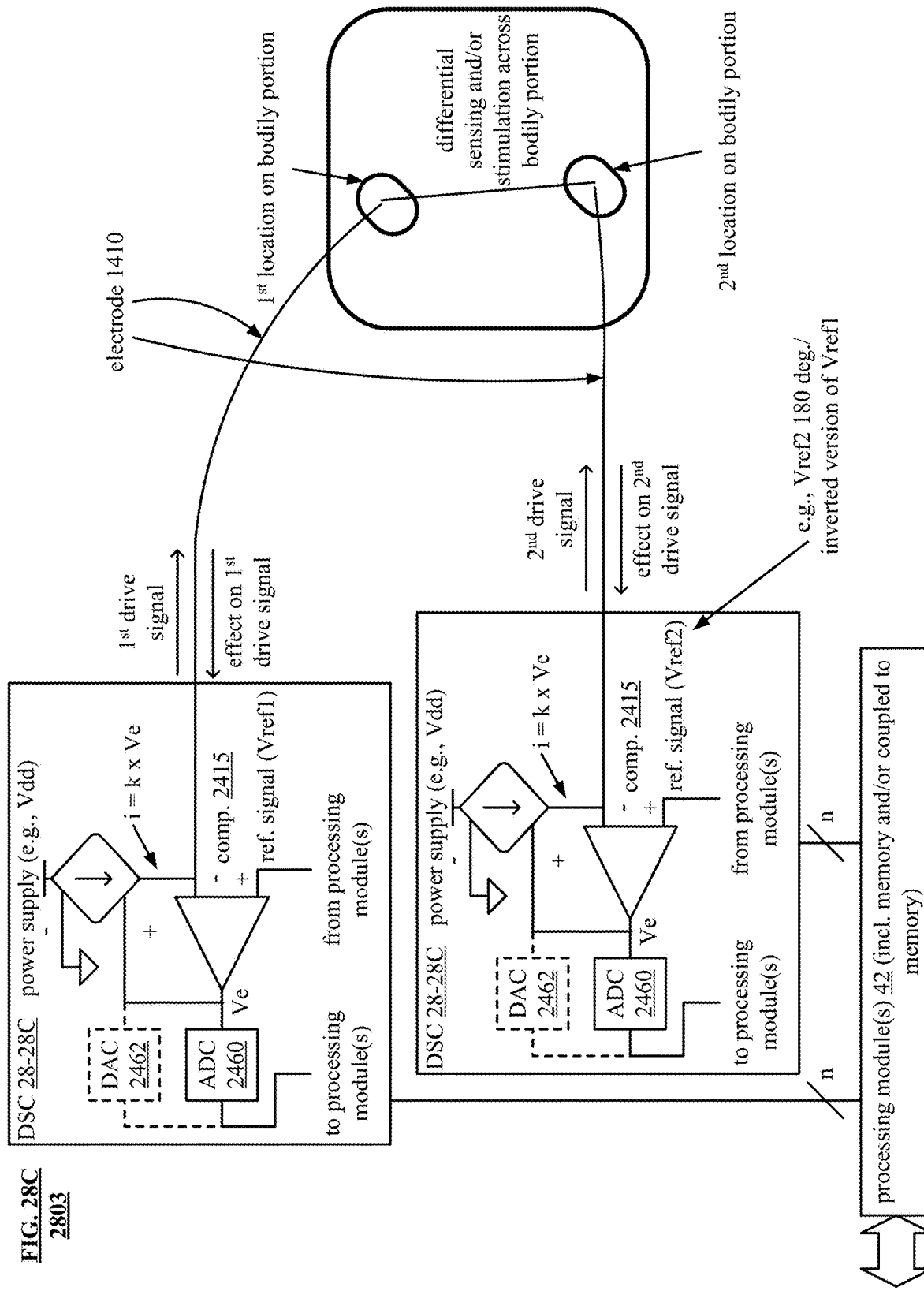
Figure 29B:
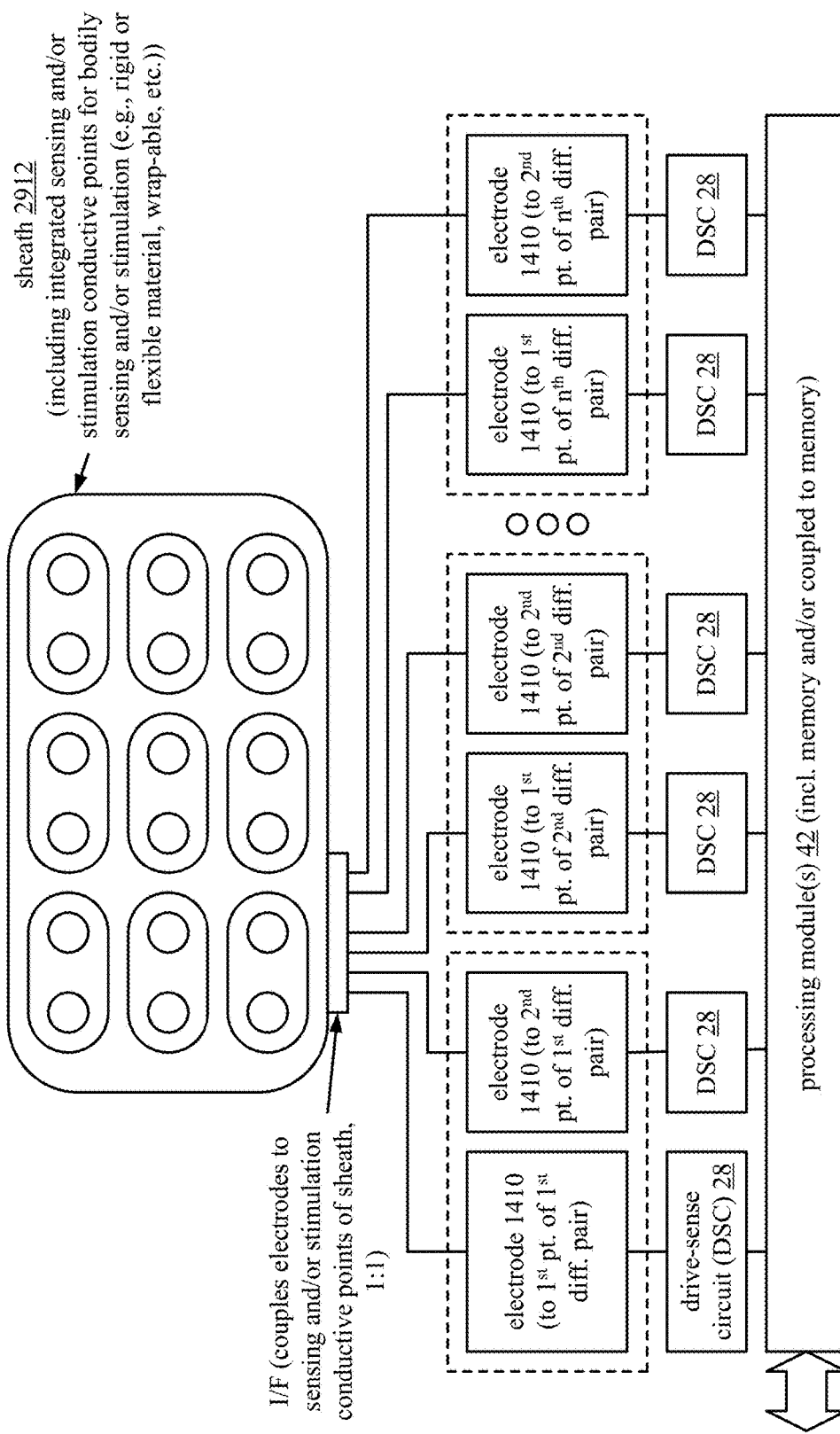
Figure 29D:
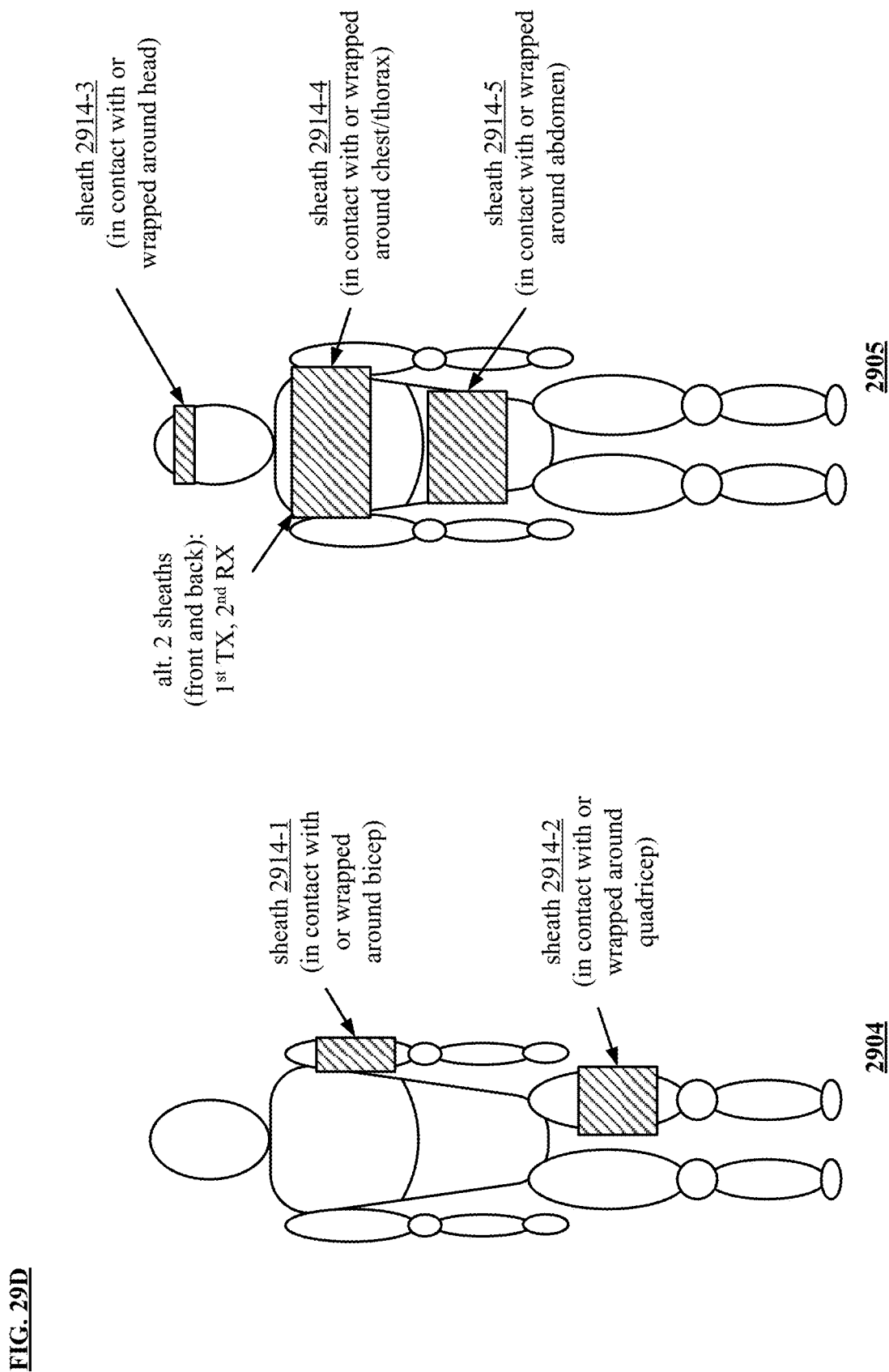
Figure 29F:
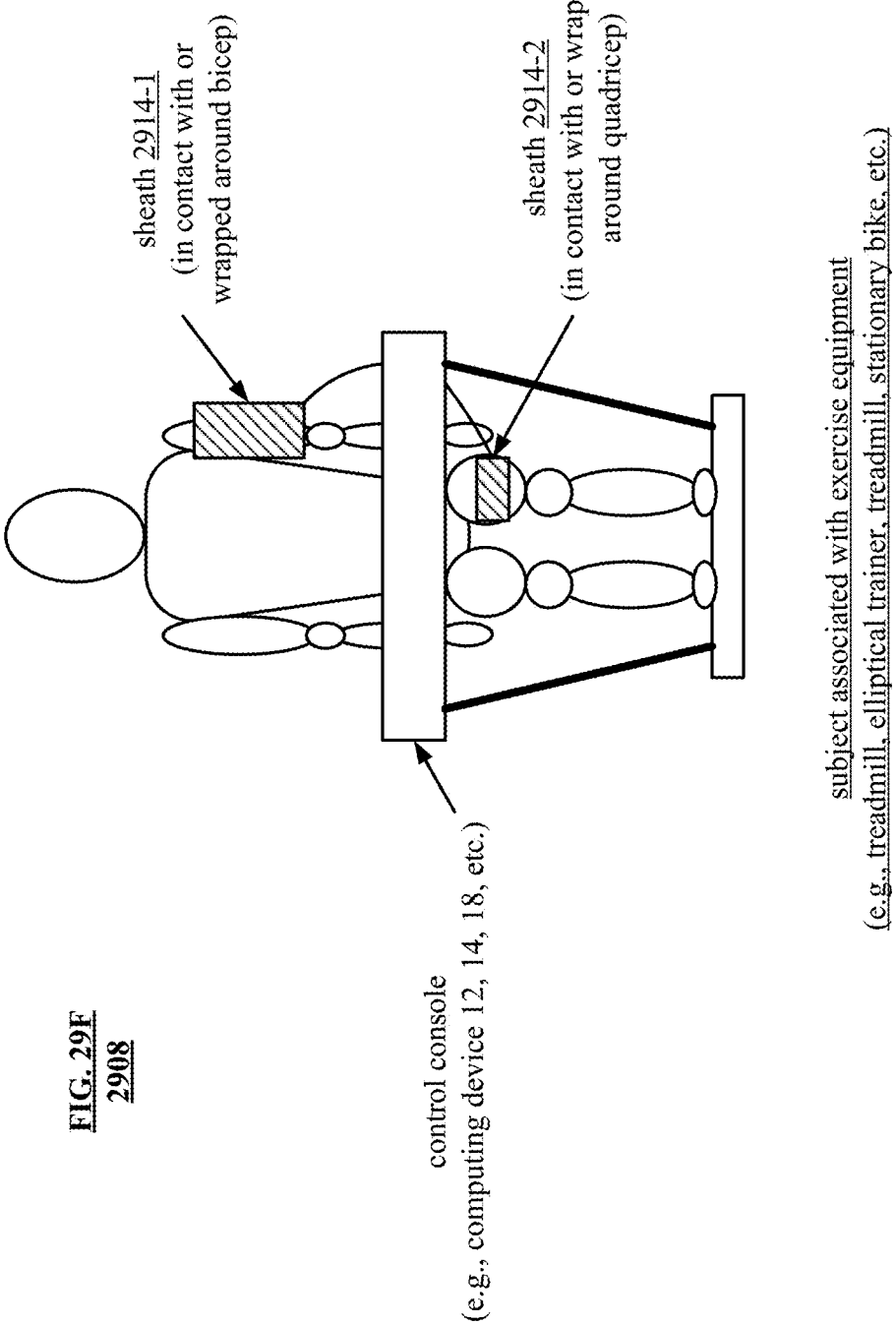
Figure 29G:
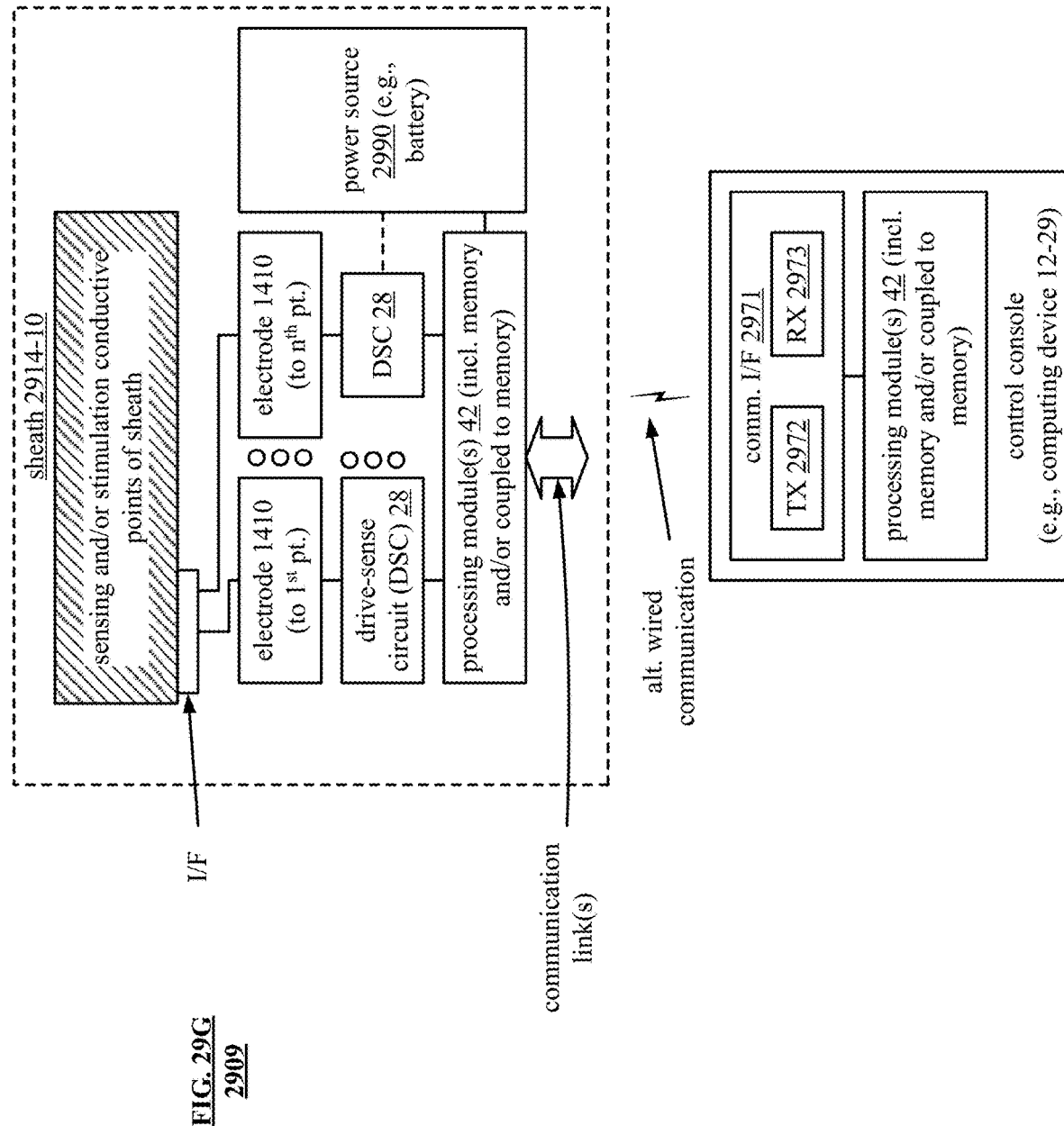
Figure 30:
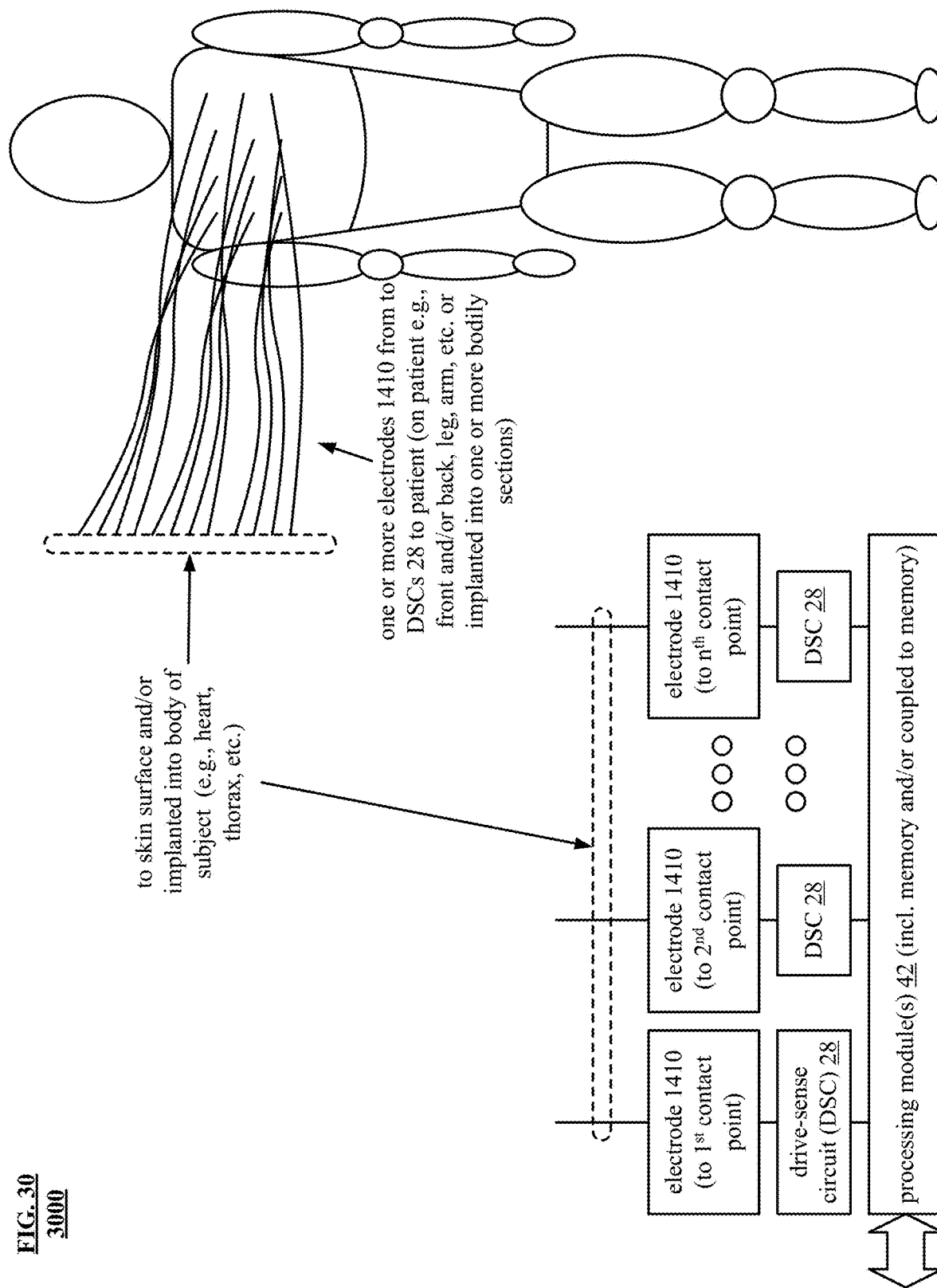
Figure 32:
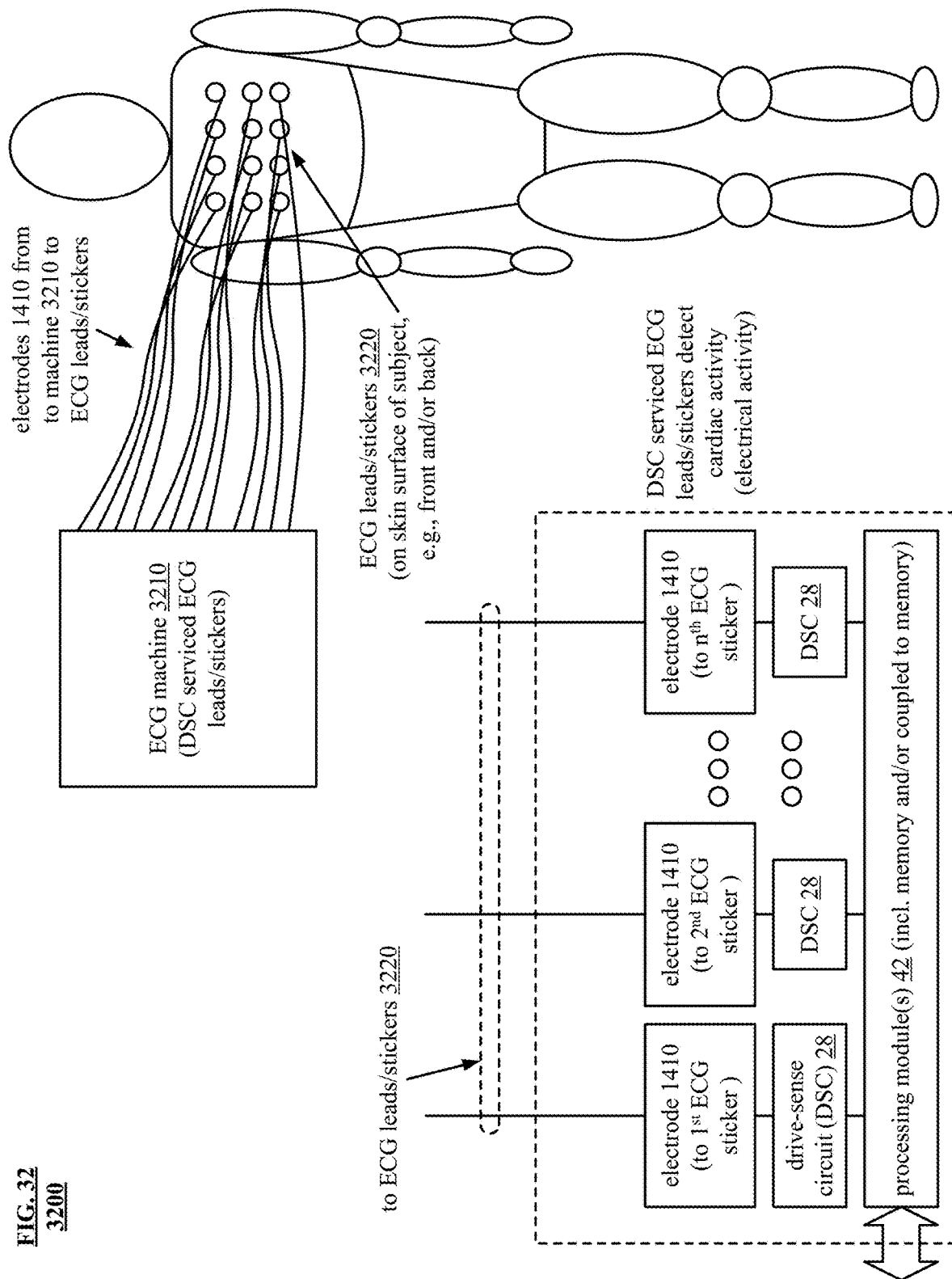
Figure 33:
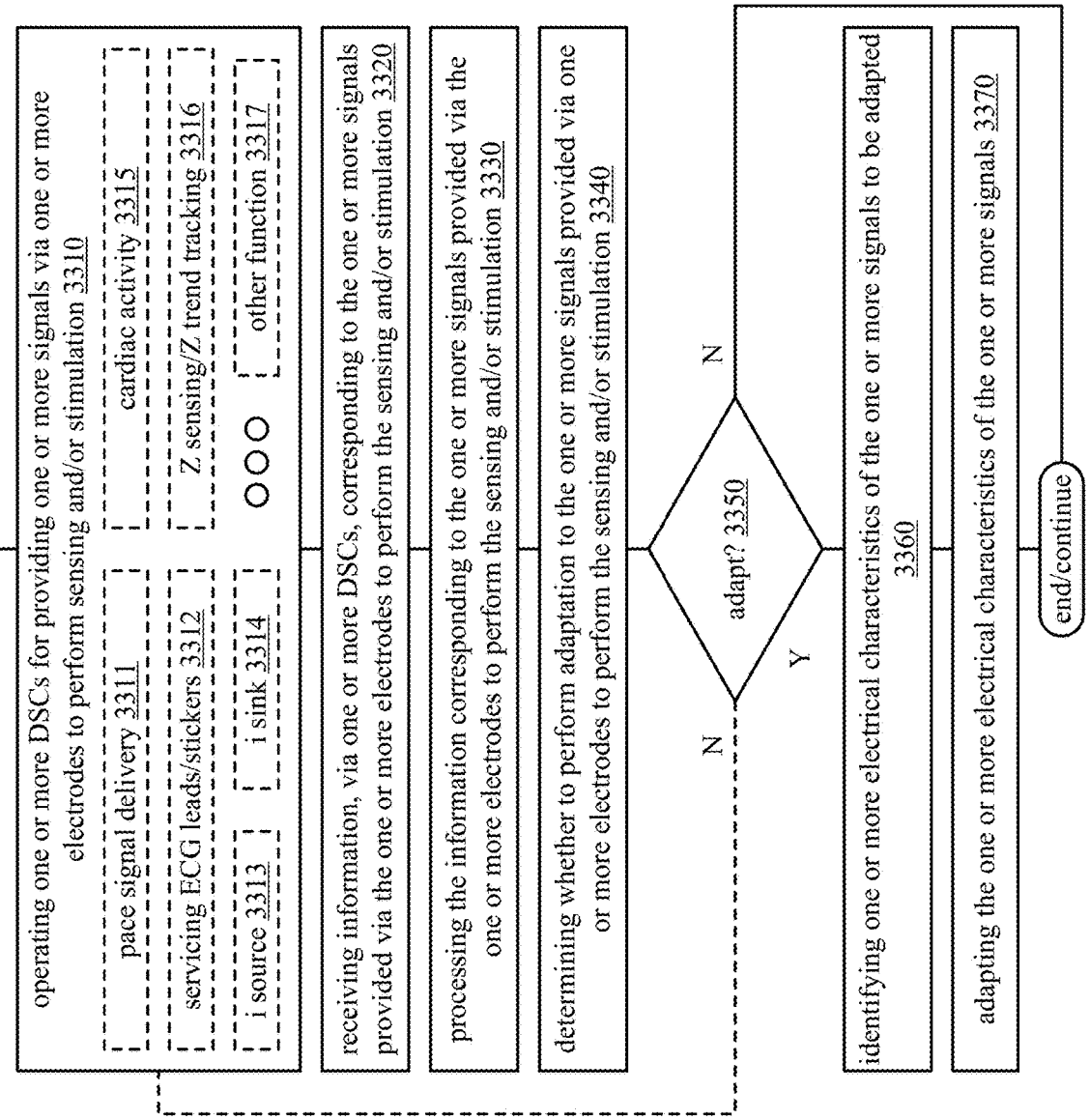

FIGS. 21A, 21B, and 21C are schematic block diagrams of embodiments of different types of pacemakers operable to be serviced by one or more DSCs in accordance with the present invention;

FIG. 21D is a schematic block diagram of an embodiment of a method for execution by one or more devices in accordance with the present invention;

FIG. 22 is schematic block diagram showing an example of a typical/normal electrocardiogram (ECG) (alternatively referred to as an EKG) showing typical locations of pacing signals and also includes a pictorial representation of the relationship between pulse signal impulse amplitude and pulse width duration that facilitate capture and that fail to schematic block in accordance with the present invention;

FIGS. 23A and 23B are schematic block diagrams of examples of pacing signals that may be used in accordance with the present invention;

FIGS. 24A and 24B are schematic block diagrams of other embodiments of DSCs configured simultaneously to drive and sense drive signals to electrodes, respectively, in accordance with the present invention;

FIGS. 25A and 25B are schematic block diagrams of embodiments of extra pathways within the heart of a subject that can cause tachycardias and one or more DSCs configured simultaneously to drive and sense drive signals to electrodes, respectively, capability to provide capability to reduce or eliminate tachycardias within the subject in accordance with the present invention;

FIGS. 26A and 26B are schematic block diagrams of other embodiments of DSCs configured simultaneously to drive and sense drive signals to electrodes, respectively, and that include capability to provide current sink signals in accordance with the present invention;

FIGS. 27A and 27B are schematic block diagrams of other embodiments of DSCs configured simultaneously to drive and sense drive signals to electrodes, respectively, and that include capability to provide current source or current sink signals in accordance with the present invention;

FIGS. 28A, 28B, and 28C are schematic block diagrams of other embodiments of DSCs configured simultaneously to drive and sense drive signals to electrodes, respectively, and that include capability to provide differential sensing and/or stimulation across one or more bodily portions of a subject in accordance with the present invention;

FIGS. 29A and 29B are schematic block diagrams of embodiments of sheaths that are serviced by DSCs that are operative simultaneously to drive and sense drive signals to electrodes, respectively, and that also includes capability to provide single-ended or differential sensing and/or stimulation across one or more bodily portions of a subject in accordance with the present invention;

FIG. 29C is a schematic block diagram of an embodiment of a sheath showing connectivity of electrodes to the sensing and/or stimulation points of the sheath in accordance with the present invention;

FIG. 29D includes schematic block diagrams of embodiments of sheaths that are operative to facilitate sensing and/or stimulation across one or more bodily portions of a subject in accordance with the present invention;

FIG. 29E includes schematic block diagrams of embodiments of sheaths that are operative to facilitate sensing and/or stimulation across one or more bodily portions of a subject to perform trend tracking based on bilateral symmetry comparative analysis in accordance with the present invention;

FIG. 29F includes schematic block diagrams of an embodiment of one or more sheaths that are operative to facilitate sensing and/or stimulation across one or more bodily portions of a subject during physical activity including adaptation thereof in accordance with the present invention;

FIG. 29G includes schematic block diagrams of an embodiment of a sheath that is in communication with a control console in accordance with the present invention;

FIG. 30 is a schematic block diagram of an embodiment of one or more electrodes that are serviced by one or more DSCs that includes capability to provide single-ended or differential sensing and/or stimulation across one or more bodily portions of a subject in accordance with the present invention;

FIGS. 31A and 31B are schematic block diagrams of embodiments of trend tracking and impedance (Z) monitoring of one or more electrodes to assist in diagnosis of health condition of a subject in accordance with the present invention;

FIG. 32 is a schematic block diagram of an embodiment of a novel electrocardiogram (ECG) (alternatively referred to as an EKG) machine that is serviced by DSCs coupled to ECG stickers via electrodes in accordance with the present invention; and FIG. 33 is a schematic block diagram of an embodiment of another method for execution by one or more devices in accordance with the present invention.

DETAILED DESCRIPTION OF THE INVENTION

Figure 1:
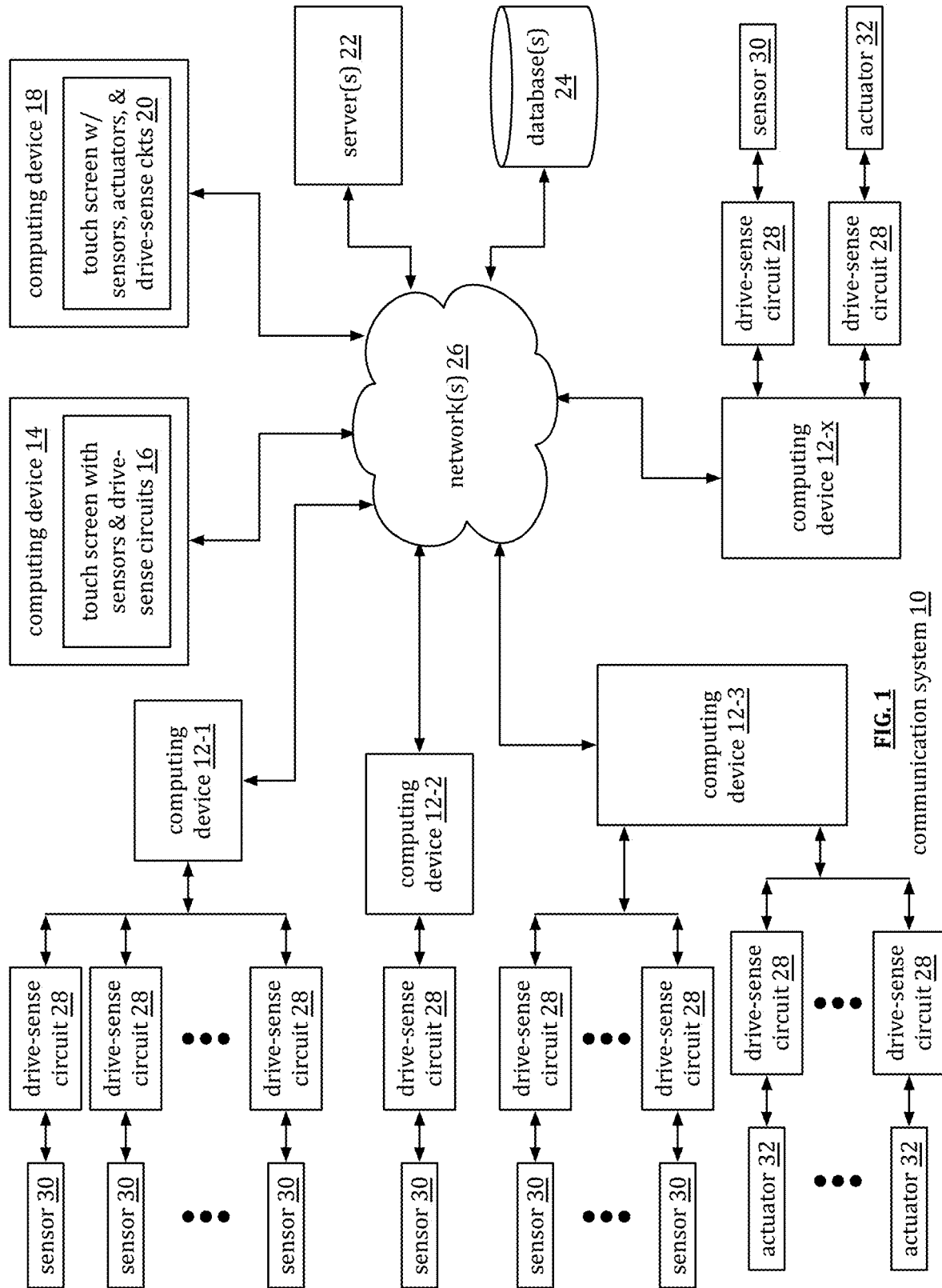
FIG. 1 is a schematic block diagram of an embodiment of a communication system in accordance with the present invention.

FIG. 1 is a schematic block diagram of an embodiment of a communication system 10 that includes a plurality of computing devices 12-10, one or more servers 22, one or more databases 24, one or more networks 26, a plurality of drive-sense circuits 28, a plurality of sensors 30, and a plurality of actuators 32. Computing devices 14 include a touchscreen 16 with sensors and drive-sensor circuits and computing devices 18 include a touch & tactic screen 20 that includes sensors, actuators, and drive-sense circuits.

A sensor 30 functions to convert a physical input into an electrical output and/or an optical output. The physical input of a sensor may be one of a variety of physical input conditions. For example, the physical condition includes one or more of, but is not limited to, acoustic waves (e.g., amplitude, phase, polarization, spectrum, and/or wave velocity); a biological and/or chemical condition (e.g., fluid concentration, level, composition, etc.); an electric condition (e.g., charge, voltage, current, conductivity, permittivity, electric field, which includes amplitude, phase, and/or polarization); a magnetic condition (e.g., flux, permeability, magnetic field, which amplitude, phase, and/or polarization); an optical condition (e.g., refractive index, reflectivity, absorption, etc.); a thermal condition (e.g., temperature, flux, specific heat, thermal conductivity, etc.); and a mechanical condition (e.g., position, velocity, acceleration, force, strain, stress, pressure, torque, etc.). For example, piezoelectric sensor converts force or pressure into an electric signal. As another example, a microphone converts audible acoustic waves into electrical signals.

There are a variety of types of sensors to sense the various types of physical conditions. Sensor types include, but are not limited to, capacitor sensors, inductive sensors, accelerometers, piezoelectric sensors, light sensors, magnetic field sensors, ultrasonic sensors, temperature sensors, infrared (IR) sensors, touch sensors, proximity sensors, pressure sensors, level sensors, smoke sensors, and gas sensors. In many ways, sensors function as the interface between the physical world and the digital world by converting real world conditions into digital signals that are then processed by computing devices for a vast number of applications including, but not limited to, medical applications, production automation applications, home environment control, public safety, and so on.

The various types of sensors have a variety of sensor characteristics that are factors in providing power to the sensors, receiving signals from the sensors, and/or interpreting the signals from the sensors. The sensor characteristics include resistance, reactance, power requirements, sensitivity, range, stability, repeatability, linearity, error, response time, and/or frequency response. For example, the resistance, reactance, and/or power requirements are factors in determining drive circuit requirements. As another example, sensitivity, stability, and/or linear are factors for interpreting the measure of the physical condition based on the received electrical and/or optical signal (e.g., measure of temperature, pressure, etc.).

An actuator 32 converts an electrical input into a physical output. The physical output of an actuator may be one of a variety of physical output conditions. For example, the physical output condition includes one or more of, but is not limited to, acoustic waves (e.g., amplitude, phase, polarization, spectrum, and/or wave velocity); a magnetic condition (e.g., flux, permeability, magnetic field, which amplitude, phase, and/or polarization); a thermal condition (e.g., temperature, flux, specific heat, thermal conductivity, etc.); and a mechanical condition (e.g., position, velocity, acceleration, force, strain, stress, pressure, torque, etc.). As an example, a piezoelectric actuator converts voltage into force or pressure. As another example, a speaker converts electrical signals into audible acoustic waves.

An actuator 32 may be one of a variety of actuators. For example, an actuator 32 is one of a comb drive, a digital micro-mirror device, an electric motor, an electroactive polymer, a hydraulic cylinder, a piezoelectric actuator, a pneumatic actuator, a screw jack, a servomechanism, a solenoid, a stepper motor, a shape-memory allow, a thermal bimorph, and a hydraulic actuator.

The various types of actuators have a variety of actuators characteristics that are factors in providing power to the actuator and sending signals to the actuators for desired performance. The actuator characteristics include resistance, reactance, power requirements, sensitivity, range, stability, repeatability, linearity, error, response time, and/or frequency response. For example, the resistance, reactance, and power requirements are factors in determining drive circuit requirements. As another example, sensitivity, stability, and/or linear are factors for generating the signaling to send to the actuator to obtain the desired physical output condition.

The computing devices 12, 14, and 18 may each be a portable computing device and/or a fixed computing device. A portable computing device may be a social networking device, a gaming device, a cell phone, a smart phone, a digital assistant, a digital music player, a digital video player, a laptop computer, a handheld computer, a tablet, a video game controller, and/or any other portable device that includes a computing core. A fixed computing device may be a computer (PC), a computer server, a cable set-top box, a satellite receiver, a television set, a printer, a fax machine, home entertainment equipment, a video game console, and/or any type of home or office computing equipment. The computing devices 12, 14, and 18 will be discussed in greater detail with reference to one or more of FIGS. 2-4.

A server 22 is a special type of computing device that is optimized for processing large amounts of data requests in parallel. A server 22 includes similar components to that of the computing devices 12, 14, and/or 18 with more robust processing modules, more main memory, and/or more hard drive memory (e.g., solid state, hard drives, etc.). Further, a server 22 is typically accessed remotely; as such it does not generally include user input devices and/or user output devices. In addition, a server may be a standalone separate computing device and/or may be a cloud computing device.

A database 24 is a special type of computing device that is optimized for large scale data storage and retrieval. A database 24 includes similar components to that of the computing devices 12, 14, and/or 18 with more hard drive memory (e.g., solid state, hard drives, etc.) and potentially with more processing modules and/or main memory. Further, a database 24 is typically accessed remotely; as such it does not generally include user input devices and/or user output devices. In addition, a database 24 may be a stand-alone separate computing device and/or may be a cloud computing device.

The network 26 includes one more local area networks (LAN) and/or one or more wide area networks WAN), which may be a public network and/or a private network. A LAN may be a wireless-LAN (e.g., Wi-Fi access point, Bluetooth, ZigBee, etc.) and/or a wired network (e.g., Firewire, Ethernet, etc.). A WAN may be a wired and/or wireless WAN. For example, a LAN may be a personal home or business's wireless network and a WAN is the Internet, cellular telephone infrastructure, and/or satellite communication infrastructure.

In an example of operation, computing device 12-1 communicates with a plurality of drive-sense circuits 28, which, in turn, communicate with a plurality of sensors 30. The sensors 30 and/or the drive-sense circuits 28 are within the computing device 12-1 and/or external to it. For example, the sensors 30 may be external to the computing device 12-1 and the drive-sense circuits are within the computing device 12-1. As another example, both the sensors 30 and the drive-sense circuits 28 are external to the computing device 12-1. When the drive-sense circuits 28 are external to the computing device, they are coupled to the computing device 12-1 via wired and/or wireless communication links as will be discussed in greater detail with reference to one or more of FIGS. 5A-5C.

The computing device 12-1 communicates with the drive-sense circuits 28 to; (a) turn them on, (b) obtain data from the sensors (individually and/or collectively), (c) instruct the drive sense circuit on how to communicate the sensed data to the computing device 12-1, (d) provide signaling attributes (e.g., DC level, AC level, frequency, power level, regulated current signal, regulated voltage signal, regulation of an impedance, frequency patterns for various sensors, different frequencies for different sensing applications, etc.) to use with the sensors, and/or (e) provide other commands and/or instructions.

As a specific example, the sensors 30 are distributed along a pipeline to measure flow rate and/or pressure within a section of the pipeline. The drive-sense circuits 28 have their own power source (e.g., battery, power supply, etc.) and are proximally located to their respective sensors 30. At desired time intervals (milliseconds, seconds, minutes, hours, etc.), the drive-sense circuits 28 provide a regulated source signal or a power signal to the sensors 30. An electrical characteristic of the sensor 30 affects the regulated source signal or power signal, which is reflective of the condition (e.g., the flow rate and/or the pressure) that sensor is sensing.

The drive-sense circuits 28 detect the effects on the regulated source signal or power signals as a result of the electrical characteristics of the sensors. The drive-sense circuits 28 then generate signals representative of change to the regulated source signal or power signal based on the detected effects on the power signals. The changes to the regulated source signals or power signals are representative of the conditions being sensed by the sensors 30.

The drive-sense circuits 28 provide the representative signals of the conditions to the computing device 12-1. A representative signal may be an analog signal or a digital signal. In either case, the computing device 12-1 interprets the representative signals to determine the pressure and/or flow rate at each sensor location along the pipeline. The computing device may then provide this information to the server 22, the database 24, and/or to another computing device for storing and/or further processing.

As another example of operation, computing device 12-2 is coupled to a drive-sense circuit 28, which is, in turn, coupled to a senor 30. The sensor 30 and/or the drive-sense circuit 28 may be internal and/or external to the computing device 12-2. In this example, the sensor 30 is sensing a condition that is particular to the computing device 12-2. For example, the sensor 30 may be a temperature sensor, an ambient light sensor, an ambient noise sensor, etc. As described above, when instructed by the computing device 12-2 (which may be a default setting for continuous sensing or at regular intervals), the drive-sense circuit 28 provides the regulated source signal or power signal to the sensor 30 and detects an effect to the regulated source signal or power signal based on an electrical characteristic of the sensor. The drive-sense circuit generates a representative signal of the affect and sends it to the computing device 12-2.

In another example of operation, computing device 12-3 is coupled to a plurality of drive-sense circuits 28 that are coupled to a plurality of sensors 30 and is coupled to a plurality of drive-sense circuits 28 that are coupled to a plurality of actuators 32. The generally functionality of the drive-sense circuits 28 coupled to the sensors 30 in accordance with the above description.

Since an actuator 32 is essentially an inverse of a sensor in that an actuator converts an electrical signal into a physical condition, while a sensor converts a physical condition into an electrical signal, the drive-sense circuits 28 can be used to power actuators 32. Thus, in this example, the computing device 12-3 provides actuation signals to the drive-sense circuits 28 for the actuators 32. The drive-sense circuits modulate the actuation signals on to power signals or regulated control signals, which are provided to the actuators 32. The actuators 32 are powered from the power signals or regulated control signals and produce the desired physical condition from the modulated actuation signals.

As another example of operation, computing device 12-$x$ is coupled to a drive-sense circuit 28 that is coupled to a sensor 30 and is coupled to a drive-sense circuit 28 that is coupled to an actuator 32. In this example, the sensor 30 and the actuator 32 are for use by the computing device 12-$x$. For example, the sensor 30 may be a piezoelectric microphone and the actuator 32 may be a piezoelectric speaker.

Figure 2:
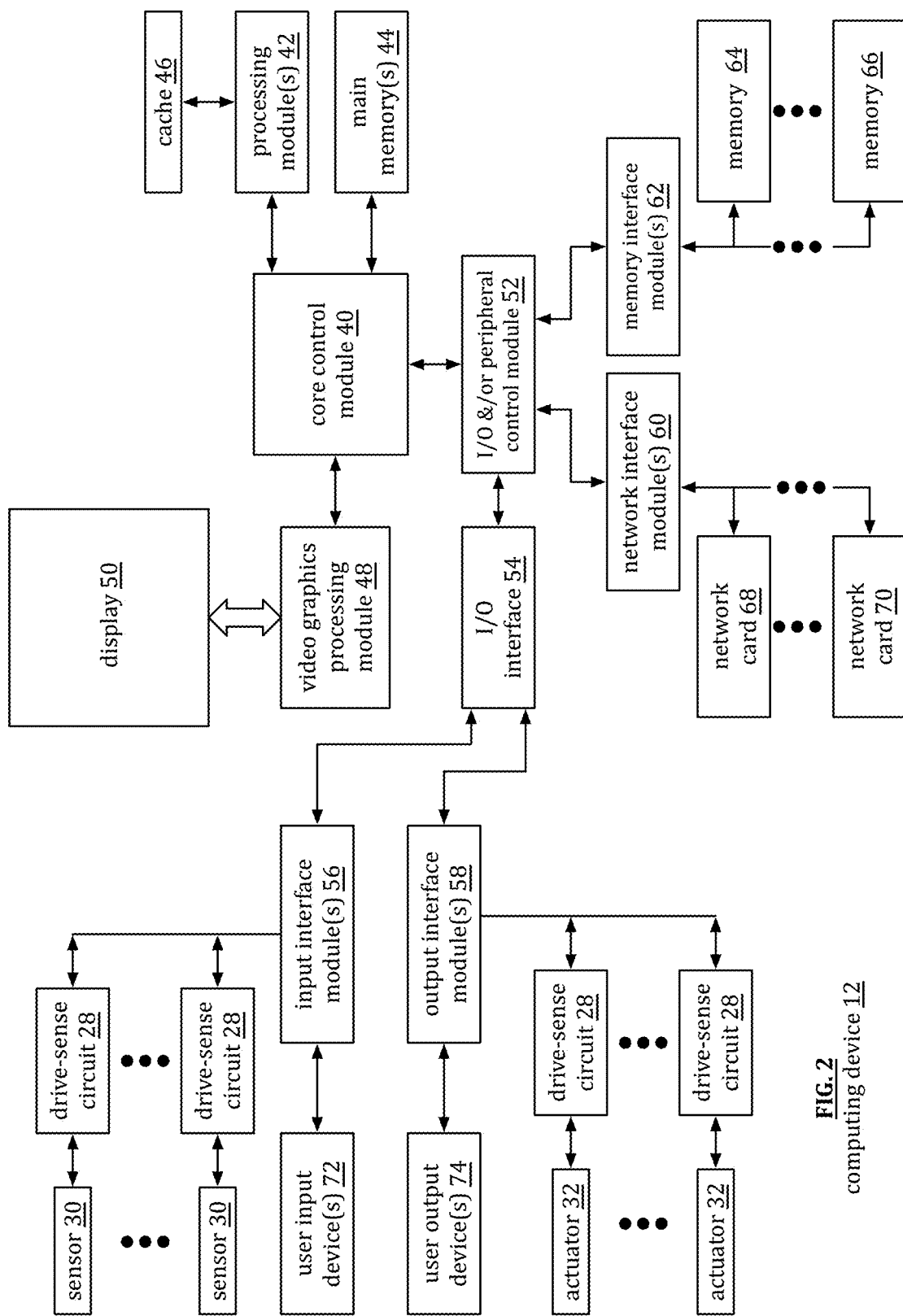
FIG. 2 is a schematic block diagram of an embodiment of a computing device in accordance with the present invention.

FIG. 2 is a schematic block diagram of an embodiment of a computing device 12 (e.g., any one of 12-1 through 12-$x$). The computing device 12 includes a core control module 40, one or more processing modules 42, one or more main memories 44, cache memory 46, a video graphics processing module 48, a display 50, an Input-Output (I/O) peripheral control module 52, one or more input interface modules 56, one or more output interface modules 58, one or more network interface modules 60, and one or more memory interface modules 62. A processing module 42 is described in greater detail at the end of the detailed description of the invention section and, in an alternative embodiment, has a direction connection to the main memory 44. In an alternate embodiment, the core control module 40 and the I/O and/or peripheral control module 52 are one module, such as a chipset, a quick path interconnect (QPI), and/or an ultra-path interconnect (UPI).

Each of the main memories 44 includes one or more Random Access Memory (RAM) integrated circuits, or chips. For example, a main memory 44 includes four DDR4 (4th generation of double data rate) RAM chips, each running at a rate of 2,400 MHz. In general, the main memory 44 stores data and operational instructions most relevant for the processing module 42. For example, the core control module 40 coordinates the transfer of data and/or operational instructions from the main memory 44 and the memory 64-66. The data and/or operational instructions retrieve from memory 64-66 are the data and/or operational instructions requested by the processing module or will most likely be needed by the processing module. When the processing module is done with the data and/or operational instructions in main memory, the core control module 40 coordinates sending updated data to the memory 64-66 for storage.

The memory 64-66 includes one or more hard drives, one or more solid state memory chips, and/or one or more other large capacity storage devices that, in comparison to cache memory and main memory devices, is/are relatively inexpensive with respect to cost per amount of data stored. The memory 64-66 is coupled to the core control module 40 via the I/O and/or peripheral control module 52 and via one or more memory interface modules 62. In an embodiment, the I/O and/or peripheral control module 52 includes one or more Peripheral Component Interface (PCI) buses to which peripheral components connect to the core control module 40. A memory interface module 62 includes a software driver and a hardware connector for coupling a memory device to the I/O and/or peripheral control module 52. For example, a memory interface 62 is in accordance with a Serial Advanced Technology Attachment (SATA) port.

The core control module 40 coordinates data communications between the processing module(s) 42 and the network(s) 26 via the I/O and/or peripheral control module 52, the network interface module(s) 60, and a network card 68 or 70. A network card 68 or 70 includes a wireless communication unit or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection. A network interface module 60 includes a software driver and a hardware connector for coupling the network card to the I/O and/or peripheral control module 52. For example, the network interface module 60 is in accordance with one or more versions of IEEE 802.11, cellular telephone protocols, 10/100/1000 Gigabit LAN protocols, etc.

The core control module 40 coordinates data communications between the processing module(s) 42 and input device(s) 72 via the input interface module(s) 56 and the I/O and/or peripheral control module 52. An input device 72 includes a keypad, a keyboard, control switches, a touchpad, a microphone, a camera, etc. An input interface module 56 includes a software driver and a hardware connector for coupling an input device to the I/O and/or peripheral control module 52. In an embodiment, an input interface module 56 is in accordance with one or more Universal Serial Bus (USB) protocols.

The core control module 40 coordinates data communications between the processing module(s) 42 and output device(s) 74 via the output interface module(s) 58 and the I/O and/or peripheral control module 52. An output device 74 includes a speaker, etc. An output interface module 58 includes a software driver and a hardware connector for coupling an output device to the I/O and/or peripheral control module 52. In an embodiment, an output interface module 56 is in accordance with one or more audio codec protocols.

The processing module 42 communicates directly with a video graphics processing module 48 to display data on the display 50. The display 50 includes an LED (light emitting diode) display, an LCD (liquid crystal display), and/or other type of display technology. The display has a resolution, an aspect ratio, and other features that affect the quality of the display. The video graphics processing module 48 receives data from the processing module 42, processes the data to produce rendered data in accordance with the characteristics of the display, and provides the rendered data to the display 50.

FIG. 2 further illustrates sensors 30 and actuators 32 coupled to drive-sense circuits 28, which are coupled to the input interface module 56 (e.g., USB port). Alternatively, one or more of the drive-sense circuits 28 is coupled to the computing device via a wireless network card (e.g., WLAN) or a wired network card (e.g., Gigabit LAN). While not shown, the computing device 12 further includes a BIOS (Basic Input Output System) memory coupled to the core control module 40.

Figure 3:
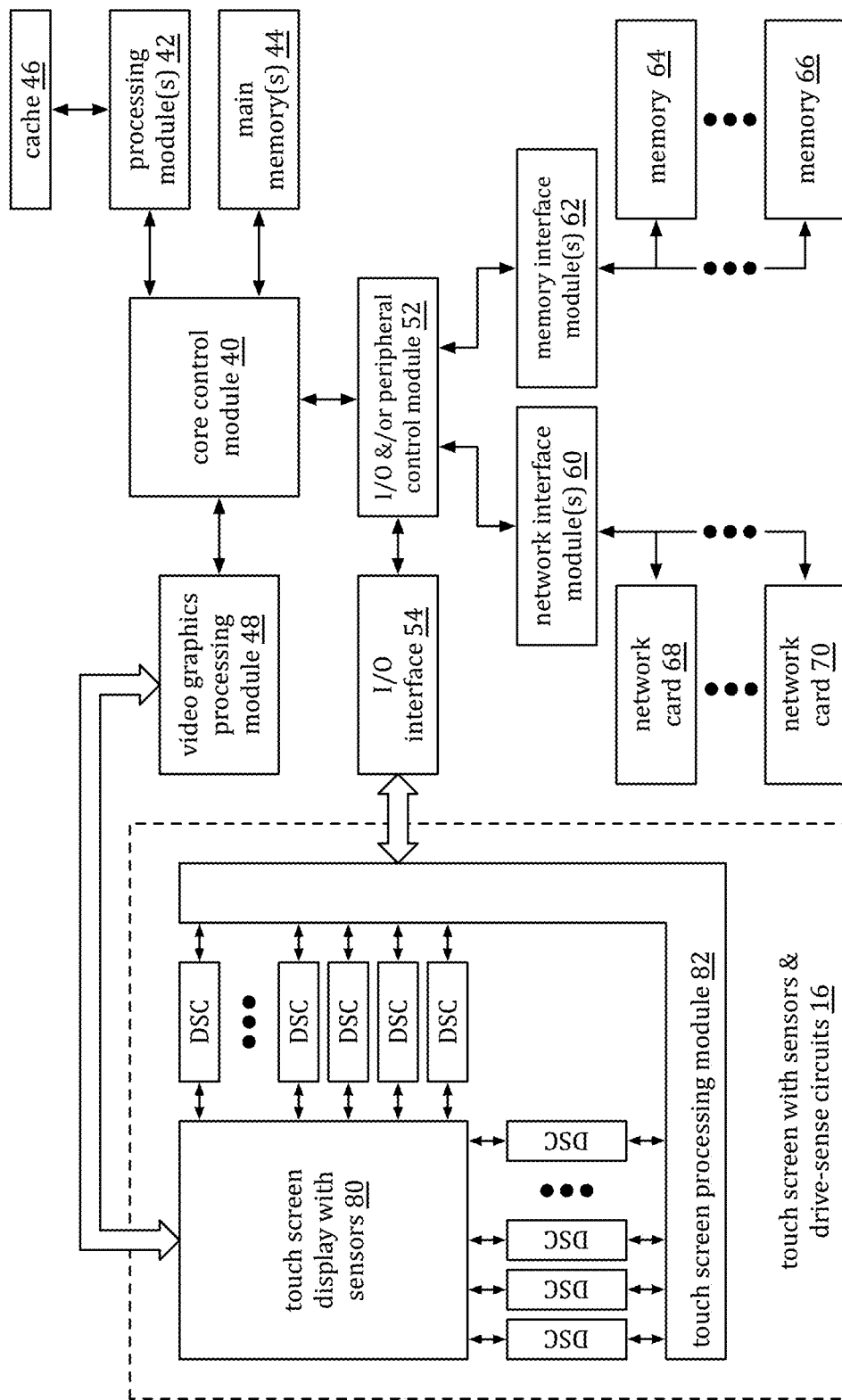
FIG. 3 is a schematic block diagram of another embodiment of a computing device in accordance with the present invention.

FIG. 3 is a schematic block diagram of another embodiment of a computing device 14 that includes a core control module 40, one or more processing modules 42, one or more main memories 44, cache memory 46, a video graphics processing module 48, a touchscreen 16, an Input-Output (I/O) peripheral control module 52, one or more input interface modules 56, one or more output interface modules 58, one or more network interface modules 60, and one or more memory interface modules 62. The touchscreen 16 includes a touchscreen display 80, a plurality of sensors 30, a plurality of drive-sense circuits (DSC), and a touchscreen processing module 82.

Computing device 14 operates similarly to computing device 12 of FIG. 2 with the addition of a touchscreen as an input device. The touchscreen includes a plurality of sensors (e.g., electrodes, capacitor sensing cells, capacitor sensors, inductive sensor, etc.) to detect a proximal touch of the screen. For example, when one or more fingers touches the screen, capacitance of sensors proximal to the touch(es) are affected (e.g., impedance changes). The drive-sense circuits (DSC) coupled to the affected sensors detect the change and provide a representation of the change to the touchscreen processing module 82, which may be a separate processing module or integrated into the processing module 42.

The touchscreen processing module 82 processes the representative signals from the drive-sense circuits (DSC) to determine the location of the touch(es). This information is inputted to the processing module 42 for processing as an input. For example, a touch represents a selection of a button on screen, a scroll function, a zoom in-out function, etc.

Figure 4:
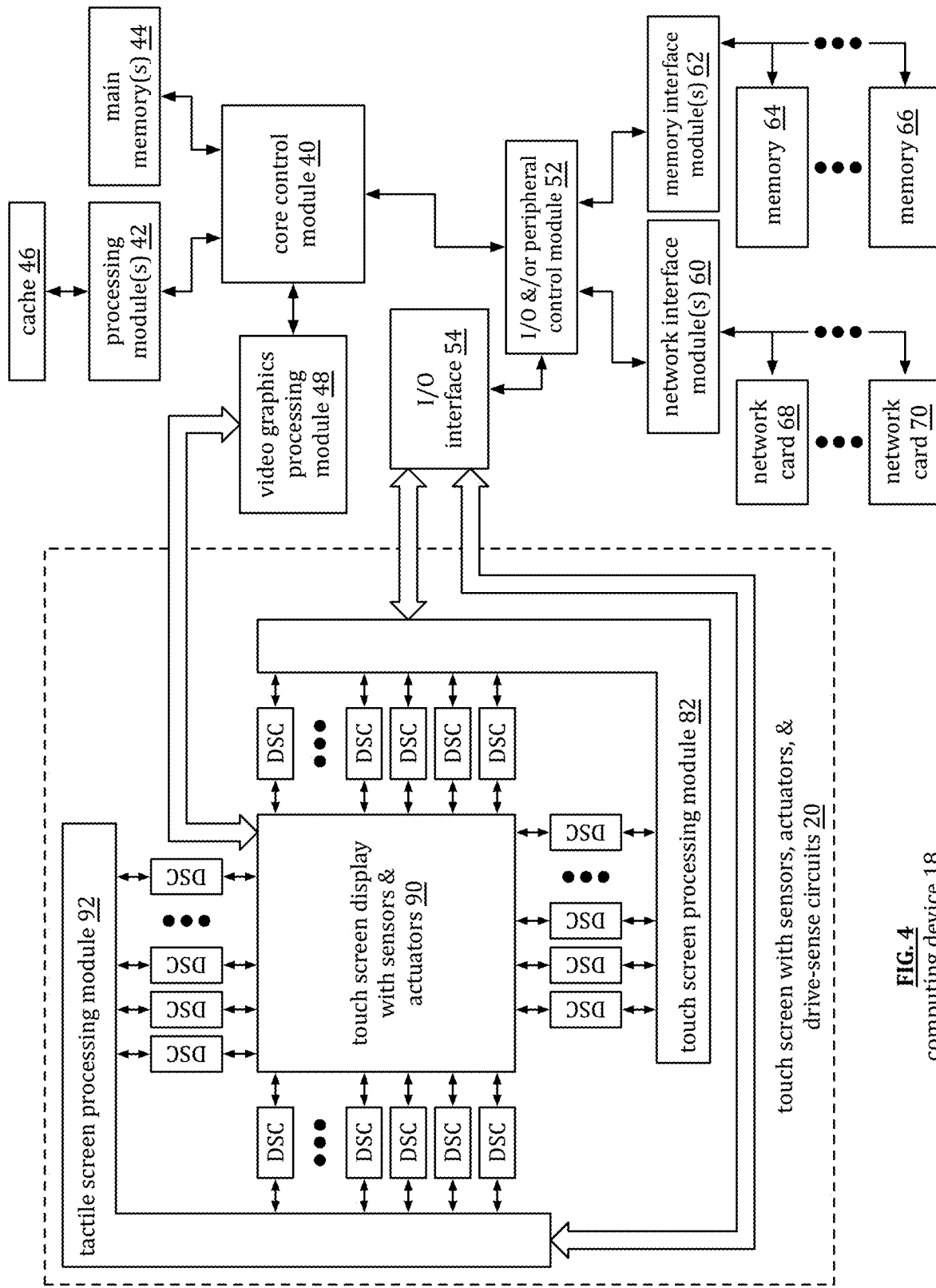
FIG. 4 is a schematic block diagram of another embodiment of a computing device in accordance with the present invention.

FIG. 4 is a schematic block diagram of another embodiment of a computing device 18 that includes a core control module 40, one or more processing modules 42, one or more main memories 44, cache memory 46, a video graphics processing module 48, a touch and tactile screen 20, an Input-Output (I/O) peripheral control module 52, one or more input interface modules 56, one or more output interface modules 58, one or more network interface modules 60, and one or more memory interface modules 62. The touch and tactile screen 20 includes a touch and tactile screen display 90, a plurality of sensors 30, a plurality of actuators 32, a plurality of drive-sense circuits (DSC), a touchscreen processing module 82, and a tactile screen processing module 92.

Computing device 18 operates similarly to computing device 14 of FIG. 3 with the addition of a tactile aspect to the screen 20 as an output device. The tactile portion of the screen 20 includes the plurality of actuators (e.g., piezoelectric transducers to create vibrations, solenoids to create movement, etc.) to provide a tactile feel to the screen 20. To do so, the processing module creates tactile data, which is provided to the appropriate drive-sense circuits (DSC) via the tactile screen processing module 92, which may be a stand-alone processing module or integrated into processing module 42. The drive-sense circuits (DSC) convert the tactile data into drive-actuate signals and provide them to the appropriate actuators to create the desired tactile feel on the screen 20.

FIG. 5A is a schematic plot diagram of a computing subsystem 25 that includes a sensed data processing module 65, a plurality of communication modules 61A-x, a plurality of processing modules 42A-x, a plurality of drive sense circuits 28, and a plurality of sensors 1-x, which may be sensors 30 of FIG. 1. The sensed data processing module 65 is one or more processing modules within one or more servers 22 and/or one or more processing modules in one or more computing devices that are different than the computing devices in which processing modules 42A-x reside.

A drive-sense circuit 28 (or multiple drive-sense circuits), a processing module (e.g., 41A), and a communication module (e.g., 61A) are within a common computing device. Each grouping of a drive-sense circuit(s), processing module, and communication module is in a separate computing device. A communication module 61A-x is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

In an example of operation, a processing module (e.g., 42A) provides a control signal to its corresponding drive-sense circuit 28. The processing module 42A may generate the control signal, receive it from the sensed data processing module 65, or receive an indication from the sensed data processing module 65 to generate the control signal. The control signal enables the drive-sense circuit 28 to provide a drive signal to its corresponding sensor. The control signal may further include a reference signal having one or more frequency components to facilitate creation of the drive signal and/or interpreting a sensed signal received from the sensor.

Based on the control signal, the drive-sense circuit 28 provides the drive signal to its corresponding sensor (e.g., 1) on a drive & sense line. While receiving the drive signal (e.g., a power signal, a regulated source signal, etc.), the sensor senses a physical condition 1-x (e.g., acoustic waves, a biological condition, a chemical condition, an electric condition, a magnetic condition, an optical condition, a thermal condition, and/or a mechanical condition). As a result of the physical condition, an electrical characteristic (e.g., impedance, voltage, current, capacitance, inductance, resistance, reactance, etc.) of the sensor changes, which affects the drive signal. Note that if the sensor is an optical sensor, it converts a sensed optical condition into an electrical characteristic.

The drive-sense circuit 28 detects the effect on the drive signal via the drive & sense line and processes the affect to produce a signal representative of power change, which may be an analog or digital signal. The processing module 42A receives the signal representative of power change, interprets it, and generates a value representing the sensed physical condition. For example, if the sensor is sensing pressure, the value representing the sensed physical condition is a measure of pressure (e.g., ×PSI (pounds per square inch)).

In accordance with a sensed data process function (e.g., algorithm, application, etc.), the sensed data processing module 65 gathers the values representing the sensed physical conditions from the processing modules. Since the sensors 1-x may be the same type of sensor (e.g., a pressure sensor), may each be different sensors, or a combination thereof; the sensed physical conditions may be the same, may each be different, or a combination thereof. The sensed data processing module 65 processes the gathered values to produce one or more desired results. For example, if the computing subsystem 25 is monitoring pressure along a pipeline, the processing of the gathered values indicates that the pressures are all within normal limits or that one or more of the sensed pressures is not within normal limits.

As another example, if the computing subsystem 25 is used in a manufacturing facility, the sensors are sensing a variety of physical conditions, such as acoustic waves (e.g., for sound proofing, sound generation, ultrasound monitoring, etc.), a biological condition (e.g., a bacterial contamination, etc.) a chemical condition (e.g., composition, gas concentration, etc.), an electric condition (e.g., current levels, voltage levels, electro-magnetic interference, etc.), a magnetic condition (e.g., induced current, magnetic field strength, magnetic field orientation, etc.), an optical condition (e.g., ambient light, infrared, etc.), a thermal condition (e.g., temperature, etc.), and/or a mechanical condition (e.g., physical position, force, pressure, acceleration, etc.).

The computing subsystem 25 may further include one or more actuators in place of one or more of the sensors and/or in addition to the sensors. When the computing subsystem 25 includes an actuator, the corresponding processing module provides an actuation control signal to the corresponding drive-sense circuit 28. The actuation control signal enables the drive-sense circuit 28 to provide a drive signal to the actuator via a drive & actuate line (e.g., similar to the drive & sense line, but for the actuator). The drive signal includes one or more frequency components and/or amplitude components to facilitate a desired actuation of the actuator.

In addition, the computing subsystem 25 may include an actuator and sensor working in concert. For example, the sensor is sensing the physical condition of the actuator. In this example, a drive-sense circuit provides a drive signal to the actuator and another drive sense signal provides the same drive signal, or a scaled version of it, to the sensor. This allows the sensor to provide near immediate and continuous sensing of the actuator's physical condition. This further allows for the sensor to operate at a first frequency and the actuator to operate at a second frequency.

In an embodiment, the computing subsystem is a stand-alone system for a wide variety of applications (e.g., manufacturing, pipelines, testing, monitoring, security, etc.). In another embodiment, the computing subsystem 25 is one subsystem of a plurality of subsystems forming a larger system. For example, different subsystems are employed based on geographic location. As a specific example, the computing subsystem 25 is deployed in one section of a factory and another computing subsystem is deployed in another part of the factory. As another example, different subsystems are employed based function of the subsystems. As a specific example, one subsystem monitors a city's traffic light operation and another subsystem monitors the city's sewage treatment plants.

Regardless of the use and/or deployment of the computing system, the physical conditions it is sensing, and/or the physical conditions it is actuating, each sensor and each actuator (if included) is driven and sensed by a single line as opposed to separate drive and sense lines. This provides many advantages including, but not limited to, lower power requirements, better ability to drive high impedance sensors, lower line to line interference, and/or concurrent sensing functions.

Figure 5B:
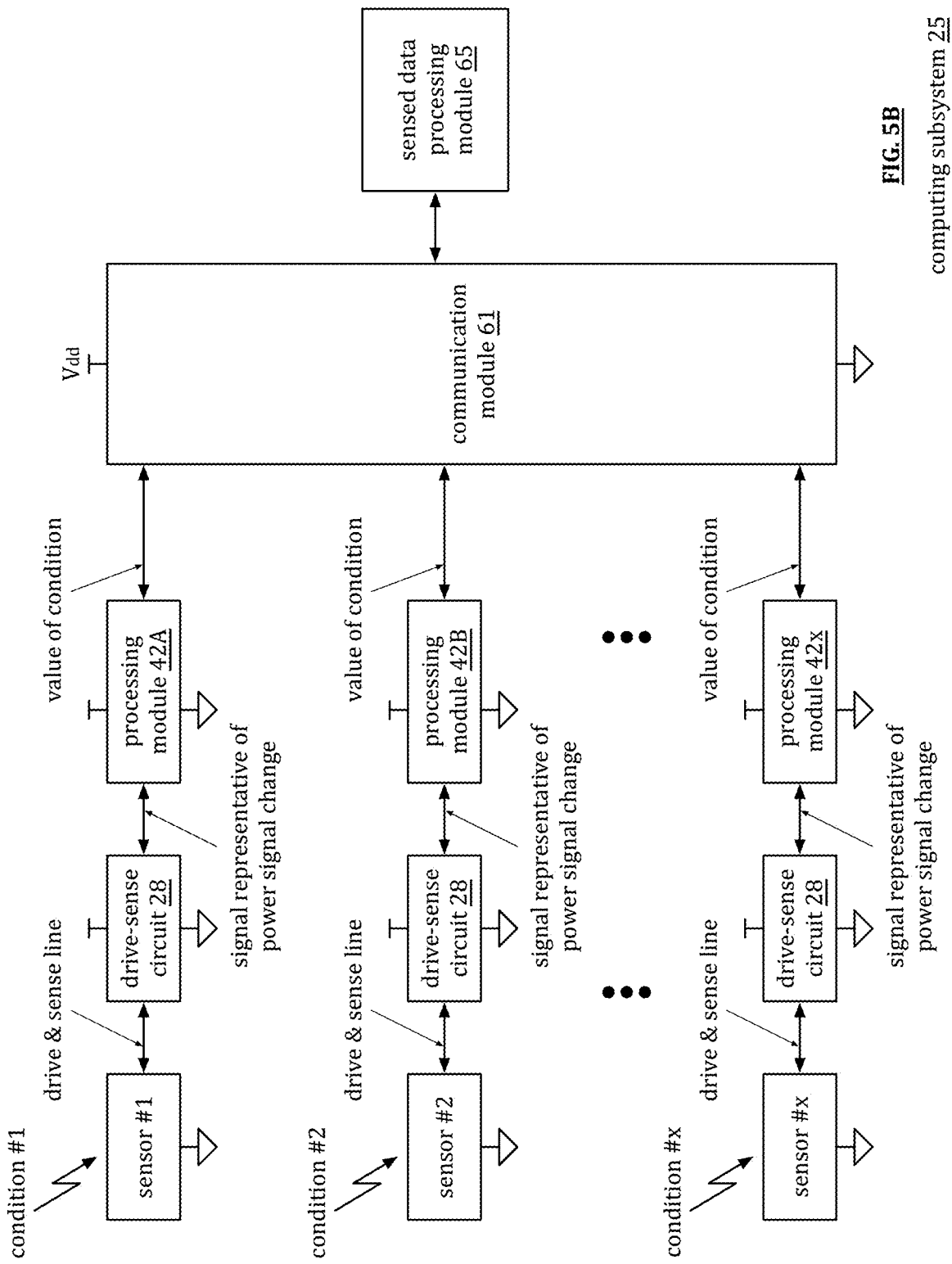
FIG. 5B is a schematic block diagram of another embodiment of a computing subsystem in accordance with the present invention.

FIG. 5B is a schematic block diagram of another embodiment of a computing subsystem 25 that includes a sensed data processing module 65, a communication module 61, a plurality of processing modules 42A-x, a plurality of drive sense circuits 28, and a plurality of sensors 1-x, which may be sensors 30 of FIG. 1. The sensed data processing module 65 is one or more processing modules within one or more servers 22 and/or one more processing modules in one or more computing devices that are different than the computing device, devices, in which processing modules 42A-x reside.

In an embodiment, the drive-sense circuits 28, the processing modules, and the communication module are within a common computing device. For example, the computing device includes a central processing unit that includes a plurality of processing modules. The functionality and operation of the sensed data processing module 65, the communication module 61, the processing modules 42A-x, the drive sense circuits 28, and the sensors 1-x are as discussed with reference to FIG. 5A.

Figure 5C:
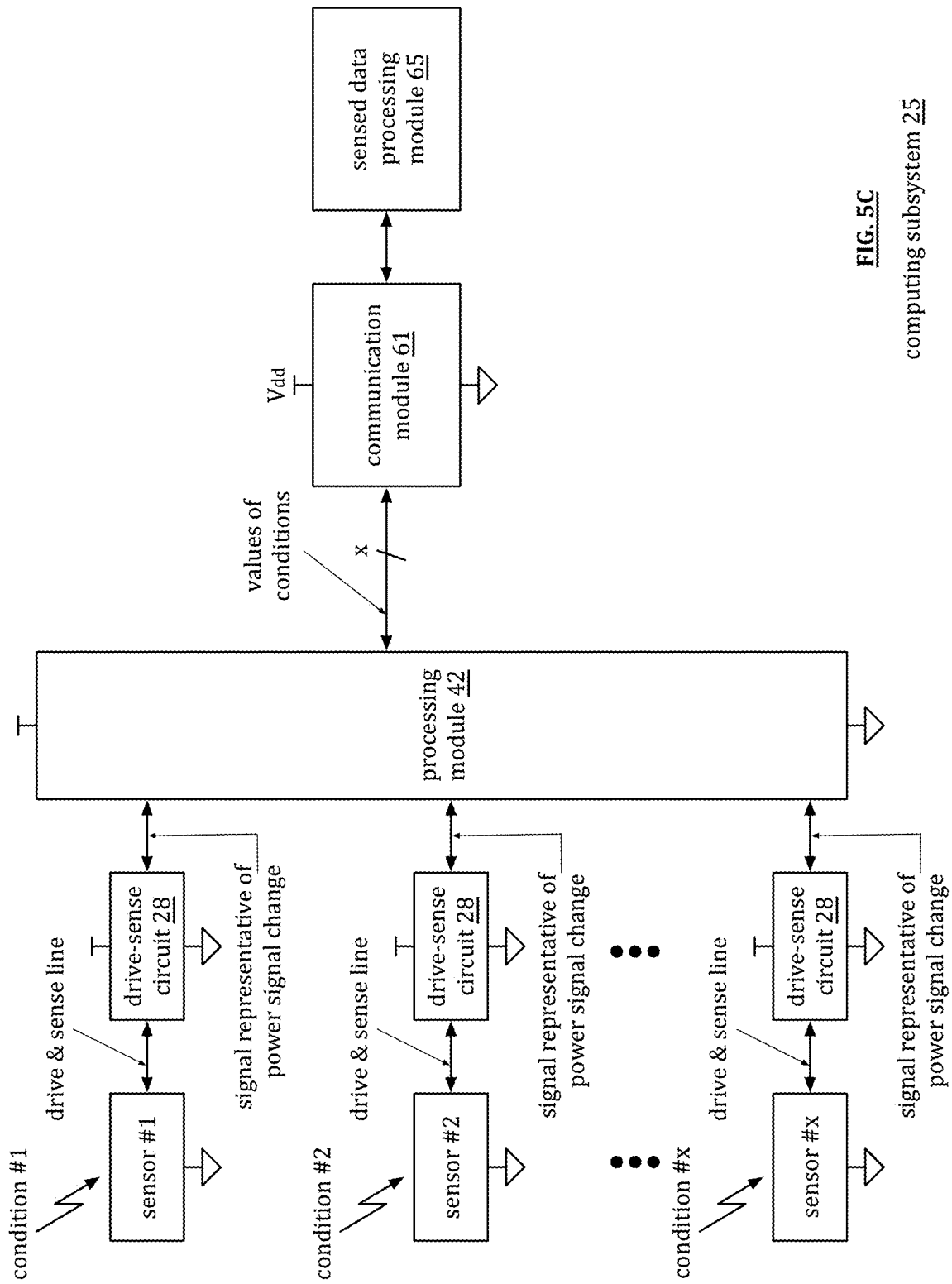
FIG. 5C is a schematic block diagram of another embodiment of a computing subsystem in accordance with the present invention.

FIG. 5C is a schematic block diagram of another embodiment of a computing subsystem 25 that includes a sensed data processing module 65, a communication module 61, a processing module 42, a plurality of drive sense circuits 28, and a plurality of sensors 1-x, which may be sensors 30 of FIG. 1. The sensed data processing module 65 is one or more processing modules within one or more servers 22 and/or one more processing modules in one or more computing devices that are different than the computing device in which the processing module 42 resides.

In an embodiment, the drive-sense circuits 28, the processing module, and the communication module are within a common computing device. The functionality and operation of the sensed data processing module 65, the communication module 61, the processing module 42, the drive sense circuits 28, and the sensors 1-x are as discussed with reference to FIG. 5A.

FIG. 5D is a schematic block diagram of another embodiment of a computing subsystem 25 that includes a processing module 42, a reference signal circuit 100, a plurality of drive sense circuits 28, and a plurality of sensors 30. The processing module 42 includes a drive-sense processing block 104, a drive-sense control block 102, and a reference control block 106. Each block 102-106 of the processing module 42 may be implemented via separate modules of the processing module, may be a combination of software and hardware within the processing module, and/or may be field programmable modules within the processing module 42.

In an example of operation, the drive-sense control block 104 generates one or more control signals to activate one or more of the drive-sense circuits 28. For example, the drive-sense control block 102 generates a control signal that enables of the drive-sense circuits 28 for a given period of time (e.g., 1 second, 1 minute, etc.). As another example, the drive-sense control block 102 generates control signals to sequentially enable the drive-sense circuits 28. As yet another example, the drive-sense control block 102 generates a series of control signals to periodically enable the drive-sense circuits 28 (e.g., enabled once every second, every minute, every hour, etc.).

Continuing with the example of operation, the reference control block 106 generates a reference control signal that it provides to the reference signal circuit 100. The reference signal circuit 100 generates, in accordance with the control signal, one or more reference signals for the drive-sense circuits 28. For example, the control signal is an enable signal, which, in response, the reference signal circuit 100 generates a pre-programmed reference signal that it provides to the drive-sense circuits 28. In another example, the reference signal circuit 100 generates a unique reference signal for each of the drive-sense circuits 28. In yet another example, the reference signal circuit 100 generates a first unique reference signal for each of the drive-sense circuits 28 in a first group and generates a second unique reference signal for each of the drive-sense circuits 28 in a second group.

The reference signal circuit 100 may be implemented in a variety of ways. For example, the reference signal circuit 100 includes a DC (direct current) voltage generator, an AC voltage generator, and a voltage combining circuit. The DC voltage generator generates a DC voltage at a first level and the AC voltage generator generates an AC voltage at a second level, which is less than or equal to the first level. The voltage combining circuit combines the DC and AC voltages to produce the reference signal. As examples, the reference signal circuit 100 generates a reference signal similar to the signals shown in FIG. 7, which will be subsequently discussed.

As another example, the reference signal circuit 100 includes a DC current generator, an AC current generator, and a current combining circuit. The DC current generator generates a DC current a first current level and the AC current generator generates an AC current at a second current level, which is less than or equal to the first current level. The current combining circuit combines the DC and AC currents to produce the reference signal.

Returning to the example of operation, the reference signal circuit 100 provides the reference signal, or signals, to the drive-sense circuits 28. When a drive-sense circuit 28 is enabled via a control signal from the drive sense control block 102, it provides a drive signal to its corresponding sensor 30. As a result of a physical condition, an electrical characteristic of the sensor is changed, which affects the drive signal. Based on the detected effect on the drive signal and the reference signal, the drive-sense circuit 28 generates a signal representative of the effect on the drive signal.

The drive-sense circuit provides the signal representative of the effect on the drive signal to the drive-sense processing block 104. The drive-sense processing block 104 processes the representative signal to produce a sensed value 97 of the physical condition (e.g., a digital value that represents a specific temperature, a specific pressure level, etc.). The processing module 42 provides the sensed value 97 to another application running on the computing device, to another computing device, and/or to a server 22.

Figure 5E:
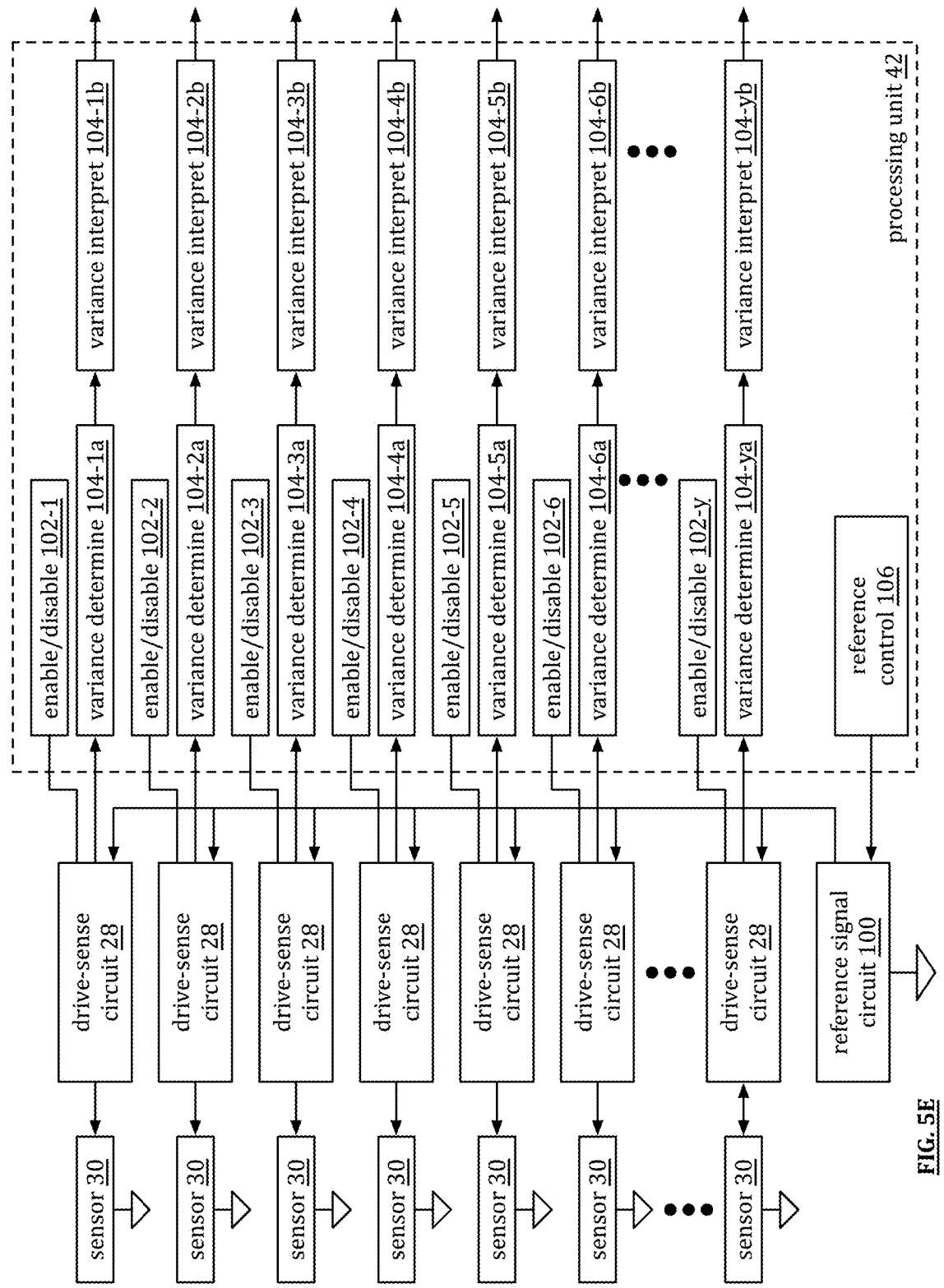
FIG. 5E is a schematic block diagram of another embodiment of a computing subsystem in accordance with the present invention.

FIG. 5E is a schematic block diagram of another embodiment of a computing subsystem 25 that includes a processing module 42, a plurality of drive sense circuits 28, and a plurality of sensors 30. This embodiment is similar to the embodiment of FIG. 5D with the functionality of the drive-sense processing block 104, a drive-sense control block 102, and a reference control block 106 shown in greater detail. For instance, the drive-sense control block 102 includes individual enable/disable blocks 102-1 through 102-y. An enable/disable block functions to enable or disable a corresponding drive-sense circuit in a manner as discussed above with reference to FIG. 5D.

The drive-sense processing block 104 includes variance determining modules 104-1a through y and variance interpreting modules 104-2a through y. For example, variance determining module 104-1a receives, from the corresponding drive-sense circuit 28, a signal representative of a physical condition sensed by a sensor. The variance determining module 104-1a functions to determine a difference from the signal representing the sensed physical condition with a signal representing a known, or reference, physical condition. The variance interpreting module 104-1b interprets the difference to determine a specific value for the sensed physical condition.

As a specific example, the variance determining module 104-1a receives a digital signal of 1001 0110 (150 in decimal) that is representative of a sensed physical condition (e.g., temperature) sensed by a sensor from the corresponding drive-sense circuit 28. With 8-bits, there are $2^8$ (256) possible signals representing the sensed physical condition. Assume that the units for temperature is Celsius and a digital value of 0100 0000 (64 in decimal) represents the known value for 25 degree Celsius. The variance determining module 104-b1 determines the difference between the digital signal representing the sensed value (e.g., 1001 0110, 150 in decimal) and the known signal value of (e.g., 0100 0000, 64 in decimal), which is 0011 0000 (86 in decimal). The variance determining module 104-b1 then determines the sensed value based on the difference and the known value. In this example, the sensed value equals 25+86*(100/256) =25+33.6=58.6 degrees Celsius.

FIG. 6 is a schematic block diagram of a drive center circuit 28-a coupled to a sensor 30. The drive sense-sense circuit 28 includes a power source circuit 110 and a power signal change detection circuit 112. The sensor 30 includes one or more transducers that have varying electrical characteristics (e.g., capacitance, inductance, impedance, current, voltage, etc.) based on varying physical conditions 114 (e.g., pressure, temperature, biological, chemical, etc.), or vice versa (e.g., an actuator).

The power source circuit 110 is operably coupled to the sensor 30 and, when enabled (e.g., from a control signal from the processing module 42, power is applied, a switch is closed, a reference signal is received, etc.) provides a power signal 116 to the sensor 30. The power source circuit 110 may be a voltage supply circuit (e.g., a battery, a linear regulator, an unregulated DC-to-DC converter, etc.) to produce a voltage-based power signal, a current supply circuit (e.g., a current source circuit, a current mirror circuit, etc.) to produce a current-based power signal, or a circuit that provide a desired power level to the sensor and substantially matches impedance of the sensor. The power source circuit 110 generates the power signal 116 to include a DC (direct current) component and/or an oscillating component.

When receiving the power signal 116 and when exposed to a condition 114, an electrical characteristic of the sensor affects 118 the power signal. When the power signal change detection circuit 112 is enabled, it detects the affect 118 on the power signal as a result of the electrical characteristic of the sensor. For example, the power signal is a 1.5 voltage signal and, under a first condition, the sensor draws 1 milliamp of current, which corresponds to an impedance of 1.5 K Ohms. Under a second conditions, the power signal remains at 1.5 volts and the current increases to 1.5 milliamps. As such, from condition 1 to condition 2, the impedance of the sensor changed from 1.5 K Ohms to 1 K Ohms. The power signal change detection circuit 112 determines this change and generates a representative signal 120 of the change to the power signal.

As another example, the power signal is a 1.5 voltage signal and, under a first condition, the sensor draws 1 milliamp of current, which corresponds to an impedance of 1.5 K Ohms. Under a second conditions, the power signal drops to 1.3 volts and the current increases to 1.3 milliamps. As such, from condition 1 to condition 2, the impedance of the sensor changed from 1.5 K Ohms to 1 K Ohms. The power signal change detection circuit 112 determines this change and generates a representative signal 120 of the change to the power signal.

The power signal 116 includes a DC component 122 and/or an oscillating component 124 as shown in FIG. 7. The oscillating component 124 includes a sinusoidal signal, a square wave signal, a triangular wave signal, a multiple level signal (e.g., has varying magnitude over time with respect to the DC component), and/or a polygonal signal (e.g., has a symmetrical or asymmetrical polygonal shape with respect to the DC component). Note that the power signal is shown without affect from the sensor as the result of a condition or changing condition.

In an embodiment, power generating circuit 110 varies frequency of the oscillating component 124 of the power signal 116 so that it can be tuned to the impedance of the sensor and/or to be off-set in frequency from other power signals in a system. For example, a capacitance sensor's impedance decreases with frequency. As such, if the frequency of the oscillating component is too high with respect to the capacitance, the capacitor looks like a short and variances in capacitances will be missed. Similarly, if the frequency of the oscillating component is too low with respect to the capacitance, the capacitor looks like an open and variances in capacitances will be missed.

In an embodiment, the power generating circuit 110 varies magnitude of the DC component 122 and/or the oscillating component 124 to improve resolution of sensing and/or to adjust power consumption of sensing. In addition, the power generating circuit 110 generates the drive signal 110 such that the magnitude of the oscillating component 124 is less than magnitude of the DC component 122.

FIG. 6A is a schematic block diagram of a drive center circuit 28-a1 coupled to a sensor 30. The drive sense-sense circuit 28-a1 includes a signal source circuit 111, a signal change detection circuit 113, and a power source 115. The power source 115 (e.g., a battery, a power supply, a current source, etc.) generates a voltage and/or current that is combined with a signal 117, which is produced by the signal source circuit 111. The combined signal is supplied to the sensor 30.

The signal source circuit 111 may be a voltage supply circuit (e.g., a battery, a linear regulator, an unregulated DC-to-DC converter, etc.) to produce a voltage-based signal 117, a current supply circuit (e.g., a current source circuit, a current mirror circuit, etc.) to produce a current-based signal 117, or a circuit that provide a desired power level to the sensor and substantially matches impedance of the sensor. The signal source circuit 111 generates the signal 117 to include a DC (direct current) component and/or an oscillating component.

When receiving the combined signal (e.g., signal 117 and power from the power source) and when exposed to a condition 114, an electrical characteristic of the sensor affects 119 the signal. When the signal change detection circuit 113 is enabled, it detects the affect 119 on the signal as a result of the electrical characteristic of the sensor.

FIG. 8 is an example of a sensor graph that plots an electrical characteristic versus a condition. The sensor has a substantially linear region in which an incremental change in a condition produces a corresponding incremental change in the electrical characteristic. The graph shows two types of electrical characteristics: one that increases as the condition increases and the other that decreases and the condition increases. As an example of the first type, impedance of a temperature sensor increases and the temperature increases. As an example of a second type, a capacitance touch sensor decreases in capacitance as a touch is sensed.

Figure 9:
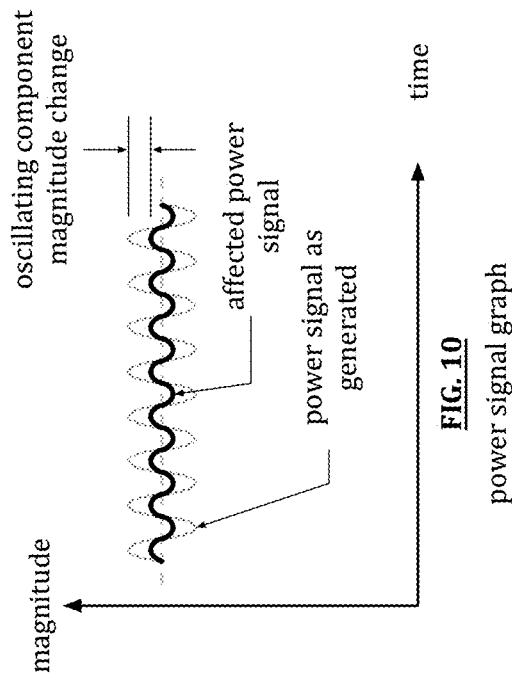
FIG. 9 is a schematic block diagram of another example of a power signal graph in accordance with the present invention.

FIG. 9 is a schematic block diagram of another example of a power signal graph in which the electrical characteristic or change in electrical characteristic of the sensor is affecting the power signal. In this example, the effect of the electrical characteristic or change in electrical characteristic of the sensor reduced the DC component but had little to no effect on the oscillating component. For example, the electrical characteristic is resistance. In this example, the resistance or change in resistance of the sensor decreased the power signal, inferring an increase in resistance for a relatively constant current.

Figure 10:
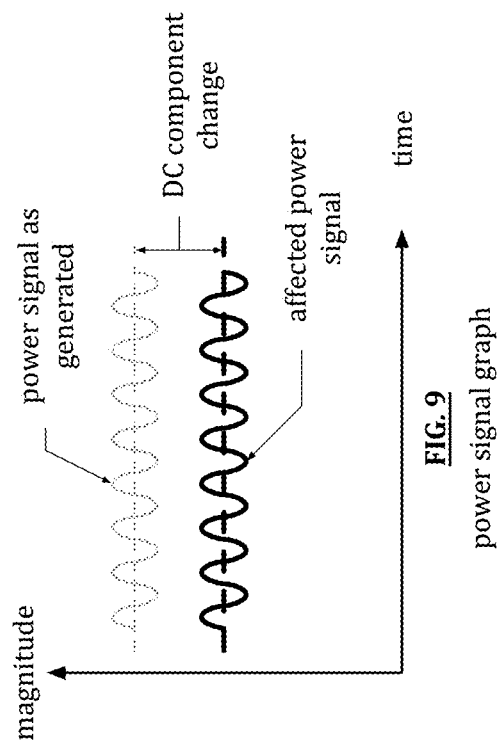
FIG. 10 is a schematic block diagram of another example of a power signal graph in accordance with the present invention.

FIG. 10 is a schematic block diagram of another example of a power signal graph in which the electrical characteristic or change in electrical characteristic of the sensor is affecting the power signal. In this example, the effect of the electrical characteristic or change in electrical characteristic of the sensor reduced magnitude of the oscillating component but had little to no effect on the DC component. For example, the electrical characteristic is impedance of a capacitor and/or an inductor. In this example, the impedance or change in impedance of the sensor decreased the magnitude of the oscillating signal component, inferring an increase in impedance for a relatively constant current.

Figure 11A:
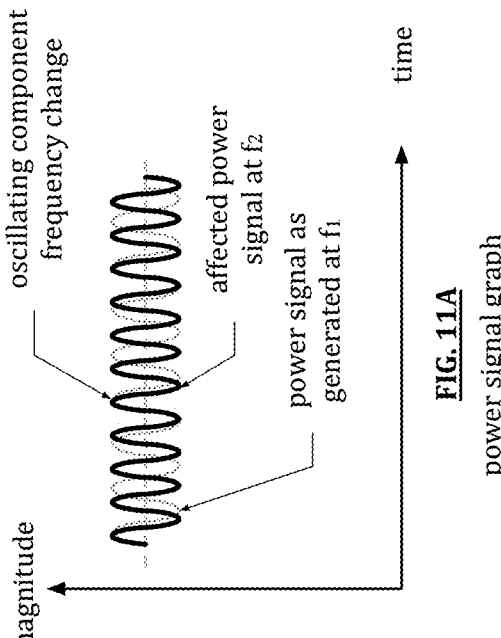
FIG. 11A is a schematic block diagram of another example of a power signal graph in accordance with the present invention.
Figure 11:
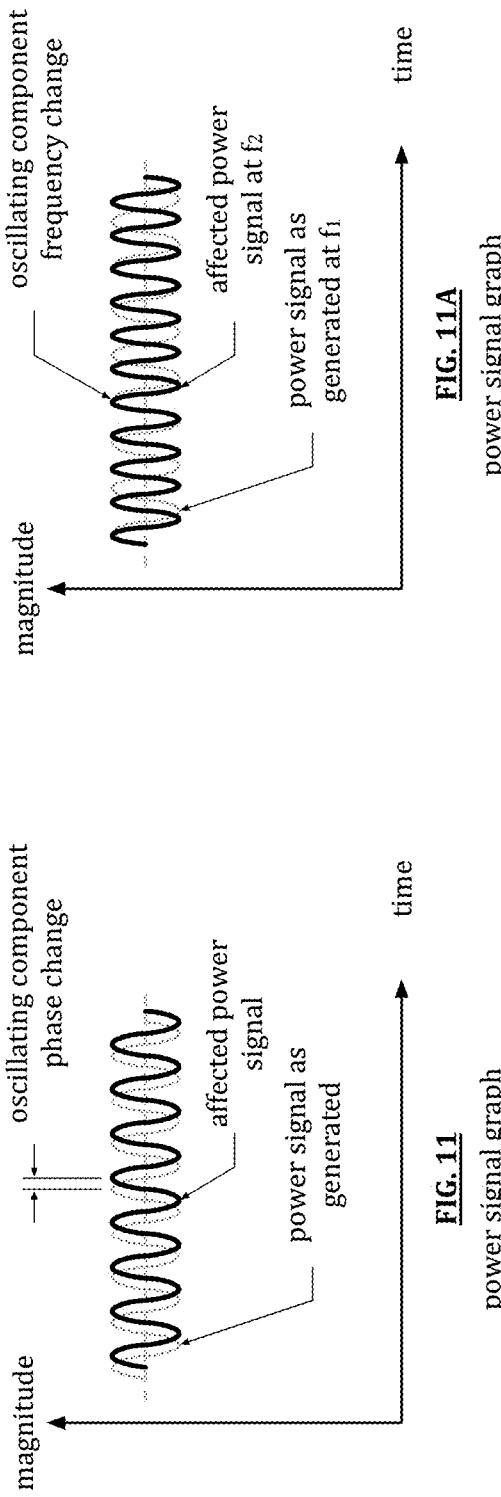
FIG. 11 is a schematic block diagram of another example of a power signal graph in accordance with the present invention.

FIG. 11 is a schematic block diagram of another example of a power signal graph in which the electrical characteristic or change in electrical characteristic of the sensor is affecting the power signal. In this example, the effect of the electrical characteristic or change in electrical characteristic of the sensor shifted frequency of the oscillating component but had little to no effect on the DC component. For example, the electrical characteristic is reactance of a capacitor and/or an inductor. In this example, the reactance or change in reactance of the sensor shifted frequency of the oscillating signal component, inferring an increase in reactance (e.g., sensor is functioning as an integrator or phase shift circuit).

FIG. 11A is a schematic block diagram of another example of a power signal graph in which the electrical characteristic or change in electrical characteristic of the sensor is affecting the power signal. In this example, the effect of the electrical characteristic or change in electrical characteristic of the sensor changes the frequency of the oscillating component but had little to no effect on the DC component. For example, the sensor includes two transducers that oscillate at different frequencies. The first transducer receives the power signal at a frequency of $f_1$ and converts it into a first physical condition. The second transducer is stimulated by the first physical condition to create an electrical signal at a different frequency $f_2$. In this example, the first and second transducers of the sensor change the frequency of the oscillating signal component, which allows for more granular sensing and/or a broader range of sensing.

FIG. 12 is a schematic block diagram of an embodiment of a power signal change detection circuit 112 receiving the affected power signal 118 and the power signal 116 as generated to produce, therefrom, the signal representative 120 of the power signal change. The affect 118 on the power signal is the result of an electrical characteristic and/or change in the electrical characteristic of a sensor; a few examples of the affects are shown in FIGS. 8-11A.

In an embodiment, the power signal change detection circuit 112 detect a change in the DC component 122 and/or the oscillating component 124 of the power signal 116. The power signal change detection circuit 112 then generates the signal representative 120 of the change to the power signal based on the change to the power signal. For example, the change to the power signal results from the impedance of the sensor and/or a change in impedance of the sensor. The representative signal 120 is reflective of the change in the power signal and/or in the change in the sensor's impedance.

In an embodiment, the power signal change detection circuit 112 is operable to detect a change to the oscillating component at a frequency, which may be a phase shift, frequency change, and/or change in magnitude of the oscillating component. The power signal change detection circuit 112 is also operable to generate the signal representative of the change to the power signal based on the change to the oscillating component at the frequency. The power signal change detection circuit 112 is further operable to provide feedback to the power source circuit 110 regarding the oscillating component. The feedback allows the power source circuit 110 to regulate the oscillating component at the desired frequency, phase, and/or magnitude.

FIG. 13 is a schematic block diagram of another embodiment of a drive sense circuit 28-b includes a change detection circuit 150, a regulation circuit 152, and a power source circuit 154. The drive-sense circuit 28-b is coupled to the sensor 30, which includes a transducer that has varying electrical characteristics (e.g., capacitance, inductance, impedance, current, voltage, etc.) based on varying physical conditions 114 (e.g., pressure, temperature, biological, chemical, etc.).

The power source circuit 154 is operably coupled to the sensor 30 and, when enabled (e.g., from a control signal from the processing module 42, power is applied, a switch is closed, a reference signal is received, etc.) provides a power signal 158 to the sensor 30. The power source circuit 154 may be a voltage supply circuit (e.g., a battery, a linear regulator, an unregulated DC-to-DC converter, etc.) to produce a voltage-based power signal or a current supply circuit (e.g., a current source circuit, a current mirror circuit, etc.) to produce a current-based power signal. The power source circuit 154 generates the power signal 158 to include a DC (direct current) component and an oscillating component.

When receiving the power signal 158 and when exposed to a condition 114, an electrical characteristic of the sensor affects 160 the power signal. When the change detection circuit 150 is enabled, it detects the affect 160 on the power signal as a result of the electrical characteristic of the sensor 30. The change detection circuit 150 is further operable to generate a signal 120 that is representative of change to the power signal based on the detected effect on the power signal.

The regulation circuit 152, when its enabled, generates regulation signal 156 to regulate the DC component to a desired DC level and/or regulate the oscillating component to a desired oscillating level (e.g., magnitude, phase, and/or frequency) based on the signal 120 that is representative of the change to the power signal. The power source circuit 154 utilizes the regulation signal 156 to keep the power signal at a desired setting 158 regardless of the electrical characteristic of the sensor. In this manner, the amount of regulation is indicative of the affect the electrical characteristic had on the power signal.

In an example, the power source circuit 158 is a DC-DC converter operable to provide a regulated power signal having DC and AC components. The change detection circuit 150 is a comparator and the regulation circuit 152 is a pulse width modulator to produce the regulation signal 156. The comparator compares the power signal 158, which is affected by the sensor, with a reference signal that includes DC and AC components. When the electrical characteristics is at a first level (e.g., a first impedance), the power signal is regulated to provide a voltage and current such that the power signal substantially resembles the reference signal.

When the electrical characteristics changes to a second level (e.g., a second impedance), the change detection circuit 150 detects a change in the DC and/or AC component of the power signal 158 and generates the representative signal 120, which indicates the changes. The regulation circuit 152 detects the change in the representative signal 120 and creates the regulation signal to substantially remove the effect on the power signal. The regulation of the power signal 158 may be done by regulating the magnitude of the DC and/or AC components, by adjusting the frequency of AC component, and/or by adjusting the phase of the AC component.

With respect to the operation of various drive-sense circuits as described herein and/or their equivalents, note that the operation of such a drive-sense circuit is operable simultaneously to drive and sense a signal via a single line. In comparison to switched, time-divided, time-multiplexed, etc. operation in which there is switching between driving and sensing (e.g., driving at first time, sensing at second time, etc.) of different respective signals at separate and distinct times, the drive-sense circuit is operable simultaneously to perform both driving and sensing of a signal. In some examples, such simultaneous driving and sensing is performed via a single line using a drive-sense circuit.

In addition, other alternative implementations of various drive-sense circuits (DSCs) are described in U.S. Utility patent application Ser. No. 16/113,379, entitled "DRIVE SENSE CIRCUIT WITH DRIVE-SENSE LINE,"filed Aug. 27, 2018, pending. Any instantiation of a drive-sense circuit as described herein may also be implemented using any of the various implementations of various drive-sense circuits (DSCs) described in U.S. Utility Patent application Ser. No. 16/113,379.

In addition, note that the one or more signals provided from a drive-sense circuit (DSC) may be of any of a variety of types. For example, such a signal may be based on encoding of one or more bits to generate one or more coded bits used to generate modulation data (or generally, data). For example, a device is configured to perform forward error correction (FEC) and/or error checking and correction (ECC) code of one or more bits to generate one or more coded bits. Examples of FEC and/or ECC may include turbo code, convolutional code, trellis coded modulation (TCM), turbo trellis coded modulation (TTCM), low density parity check (LDPC) code, Reed-Solomon (RS) code, BCH (Bose and Ray-Chaudhuri, and Hocquenghem) code, binary convolutional code (BCC), Cyclic Redundancy Check (CRC), and/or any other type of ECC and/or FEC code and/or combination thereof, etc. Note that more than one type of ECC and/or FEC code may be used in any of various implementations including concatenation (e.g., first ECC and/or FEC code followed by second ECC and/or FEC code, etc. such as based on an inner code/outer code architecture, etc.), parallel architecture (e.g., such that first ECC and/or FEC code operates on first bits while second ECC and/or FEC code operates on second bits, etc.), and/or any combination thereof.

Also, the one or more coded bits may then undergo modulation or symbol mapping to generate modulation symbols (e.g., the modulation symbols may include data intended for one or more recipient devices, components, elements, etc.). Note that such modulation symbols may be generated using any of various types of modulation coding techniques. Examples of such modulation coding techniques may include binary phase shift keying (BPSK), quadrature phase shift keying (QPSK), 8-phase shift keying (PSK), 16 quadrature amplitude modulation (QAM), 32 amplitude and phase shift keying (APSK), etc., uncoded modulation, and/or any other desired types of modulation including higher ordered modulations that may include even greater number of constellation points (e.g., 1024 QAM, etc.).

In addition, note that a signal provided from a DSC may be of a unique frequency that is different from signals provided from other DSCs. Also, a signal provided from a DSC may include multiple frequencies independently or simultaneously. The frequency of the signal can be hopped on a pre-arranged pattern. In some examples, a handshake is established between one or more DSCs and one or more processing modules (e.g., one or more controllers) such that the one or more DSC is/are directed by the one or more processing modules regarding which frequency or frequencies and/or which other one or more characteristics of the one or more signals to use at one or more respective times and/or in one or more particular situations.

With respect to any signal that is driven and simultaneously detected by a DSC, note that any additional signal that is coupled into a line, an electrode, a touch sensor, a bus, a communication link, a battery, a load, an electrical coupling or connection, etc. associated with that DSC is also detectable. For example, a DSC that is associated with such a line, an electrode, a touch sensor, a bus, a communication link, a load, an electrical coupling or connection, a pacemaker lead, a sensing lead, a lead that is operable to facilitate both pacemaker and sensing functionality, etc. is configured to detect any signal from one or more other lines, electrodes, touch sensors, buses, communication links, loads, electrical couplings or connections, etc. that get coupled into that line, electrode, touch sensor, bus, communication link, electrical coupling or connection, a pacemaker lead, a sensing lead, a lead that is operable to perform both pacemaker and sensing functionality, etc.

Note that the different respective signals that are driven and simultaneously sensed by one or more DSCs may be differentiated from one another. Appropriate filtering and processing can identify the various signals given their differentiation, orthogonality to one another, difference in frequency, etc. Other examples described herein and their equivalents operate using any of a number of different characteristics other than or in addition to frequency.

Moreover, with respect to any embodiment, diagram, example, etc. that includes more than one DSC, note that the DSCs may be implemented in a variety of manners. For example, all of the DSCs may be of the same type, implementation, configuration, etc. In another example, the first DSC may be of a first type, implementation, configuration, etc., and a second DSC may be of a second type, implementation, configuration, etc. that is different than the first DSC. Considering a specific example, a first DSC may be implemented to detect change of impedance associated with a line, an electrode, a touch sensor, a bus, a communication link, an electrical coupling or connection, etc. associated with that first DSC, while a second DSC may be implemented to detect change of voltage associated with a line, an electrode, a touch sensor, a bus, a communication link, an electrical coupling or connection, etc. associated with that second DSC. In addition, note that a third DSC may be implemented to detect change of a current associated with a line, an electrode, a touch sensor, a bus, a communication link, an electrical coupling or connection, etc. associated with that DSC. In general, while a common reference may be used generally to show a DSC or multiple instantiations of a DSC within a given embodiment, diagram, example, etc., note that any particular DSC may be implemented in accordance with any manner as described herein, such as described in U.S. Utility patent application Ser. No. 16/113, 379, etc. and/or their equivalents.

Note that certain of the diagrams herein show a computing device (e.g., alternatively referred to as device; the terms computing device and device may be used interchangeably) that may include or be coupled to one or more processing modules. In certain instances, the one or more processing modules is configured to communicate with and interact with one or more other devices including one or more of DSCs, one or more components associated with a DSC such as one or more of a line, an electrode, a touch sensor, a bus, a communication link, a load, an electrical coupling or connection, a sensing and/or stimulation point such as located at the end of an electrode that may be applied to and associated with a subject (e.g., a user, person, a patient, etc.), a sensing and/or stimulation point such as located within a sheath that may be applied to and associated with a subject (e.g., a user, person, a patient, etc.), a pacemaker lead, a sensing lead, a lead that is operable to facilitate both pacemaker and sensing functionality, etc. Note that reference to a subject herein may be used interchangeably with the user, person, patient, etc. generally speaking, many of the various aspects, embodiments, and/or examples of the invention (and/or their equivalents) provide means by which sensing and/or stimulation may be performed using one or more DSCs and one or more of electrodes, which may be implemented in a variety of different ways including one or more of a pacemaker lead, a sensing lead, a lead that is operable to facilitate both pacemaker and sensing functionality, etc. to facilitate such sensing and/or stimulation of one or more ugly portions of a subject.

Note that any such implementation of one or more processing modules may include integrated memory and/or be coupled to other memory. At least some of the memory stores operational instructions to be executed by the one or more processing modules. In addition, note that the one or more processing modules may interface with one or more other devices, components, elements, etc. via one or more communication links, networks, communication pathways, channels, etc. (e.g., such as via one or more communication interfaces of the device, such as may be integrated into the one or more processing modules or be implemented as a separate component, circuitry, etc.).

In addition, when a DSC is implemented to communicate with and interact with another element, the DSC is configured simultaneously to transmit and receive one or more signals with the element. For example, a DSC is configured simultaneously to sense (e.g., including to sense change of) and to drive one or more signals to the one element. During transmission of a signal from a DSC, that same DSC is configured simultaneously to sense the signal being transmitted from the DSC including any change thereof including any other signal may be coupled into the signal that is being transmitted from the DSC.

In addition, while many examples, embodiments, diagrams, etc. herein include one or more DSCs (e.g., coupled to one or more processing modules and one or more electrodes), note that any instantiation of a DSC may alternatively be implemented using a channel drive circuitry, an Analog Front End (AFE) that includes analog to digital and/or digital to analog conversion capability, etc. within alternative embodiments.

FIG. 14 is a schematic block diagram of an embodiment 1400 of a DSC that is interactive with an electrode in accordance with the present invention. Similar to other diagrams, examples, embodiments, etc. herein, the DSC 28-a2 of this diagram is in communication with one or more processing modules 42. The DSC 28-a2 is configured to provide a signal (e.g., a power signal, an electrode signal, transmit signal, a monitoring signal, etc.) to the electrode 1410 via a single line and simultaneously to sense that signal via the single line. In some examples, sensing the signal includes detection of an electrical characteristic of the electrode that is based on a response of the electrode 1410 to that signal. Examples of such an electrical characteristic may include detection of an impedance of the electrode 1410 such as a change of capacitance of the electrode 1410, detection of one or more signals coupled into the electrode 1410 such as from one or more other electrodes, and/or other electrical characteristics.

This embodiment of a DSC 28-a2 includes a current source 110-1 and a power signal change detection circuit 112-a1. The power signal change detection circuit 112-a1 includes a power source reference circuit 130 and a comparator 132. In some examples, the comparator 132 is alternatively be implemented as an operational amplifier. The current source 110-1 may be an independent current source, a dependent current source, a current mirror circuit, etc.

In an example of operation, the power source reference circuit 130 provides a current reference 134 with DC and oscillating components to the current source 110-1. The current source generates a current as the power signal 116 based on the current reference 134. An electrical characteristic of the electrode 1410 has an effect on the current power signal 116. For example, if the impedance of the electrode 1410 decreases and the current power signal 116 remains substantially unchanged, the voltage across the electrode 1410 is decreased.

The comparator 132 compares the current reference 134 with the affected power signal 118 to produce the signal 120 that is representative of the change to the power signal. For example, the current reference signal 134 corresponds to a given current (I) times a given impedance (Z). The current reference generates the power signal to produce the given current (I). If the impedance of the electrode 1410 substantially matches the given impedance (Z), then the comparator's output is reflective of the impedances substantially matching. If the impedance of the electrode 1410 is greater than the given impedance (Z), then the comparator's output is indicative of how much greater the impedance of the electrode 1410 is than that of the given impedance (Z). If the impedance of the electrode 1410 is less than the given impedance (Z), then the comparator's output is indicative of how much less the impedance of the electrode 1410 is than that of the given impedance (Z).

FIG. 15 is a schematic block diagram of another embodiment 1500 of a DSC that is interactive with an electrode in accordance with the present invention. Similar to other diagrams, examples, embodiments, etc. herein, the DSC 28-a3 of this diagram is in communication with one or more processing modules 42. Similar to the previous diagram, although providing a different embodiment of the DSC, the DSC 28-a3 is configured to provide a signal to the electrode 1410 via a single line and simultaneously to sense that signal via the single line. In some examples, sensing the signal includes detection of an electrical characteristic of the electrode 1410 that is based on a response of the electrode 1410 to that signal. Examples of such an electrical characteristic may include detection of an impedance of the electrode 1410 such as a change of capacitance of the electrode 1410, detection of one or more signals coupled into the electrode 1410 such as from one or more other electrodes, and/or other electrical characteristics.

This embodiment of a DSC 28-*a*3 includes a voltage source 110-2 and a power signal change detection circuit 112-*a*2. The power signal change detection circuit 112-*a*2 includes a power source reference circuit 130-2 and a comparator 132-2. The voltage source 110-2 may be a battery, a linear regulator, a DC-DC converter, etc.

In an example of operation, the power source reference circuit 130-2 provides a voltage reference 136 with DC and oscillating components to the voltage source 110-2. The voltage source generates a voltage as the power signal 116 based on the voltage reference 136. An electrical characteristic of the electrode 1410 has an effect on the voltage power signal 116. For example, if the impedance of the electrode 1410 decreases and the voltage power signal 116 remains substantially unchanged, the current through the electrode 1410 is increased.

The comparator 132 compares the voltage reference 136 with the affected power signal 118 to produce the signal 120 that is representative of the change to the power signal. For example, the voltage reference signal 134 corresponds to a given voltage (V) divided by a given impedance (Z). The voltage reference generates the power signal to produce the given voltage (V). If the impedance of the electrode 1410 substantially matches the given impedance (Z), then the comparator's output is reflective of the impedances substantially matching. If the impedance of the electrode 1410 is greater than the given impedance (Z), then the comparator's output is indicative of how much greater the impedance of the electrode 1410 is than that of the given impedance (Z). If the impedance of the electrode 1410 is less than the given impedance (Z), then the comparator's output is indicative of how much less the impedance of the electrode 1410 is than that of the given impedance (Z).

With respect to many of the following diagrams, one or more processing modules 42, which includes and/or is coupled to memory, is configured to communicate and interact with one or more DSCs 28 that are coupled to one or more electrodes. Note that the electrodes may be implemented for delivery of one or more signals including for pacing signaling (e.g., such as with respect to a cardiac implemented pacemaker to assist a subject in controlling heart function) or stimulation and/or sensing such as with respect to detecting electrical activity such as cardiac activity, impedance sensing, etc. In other examples, the electrodes are coupled to a panel or a touchscreen display such as may be implemented within a touch sensor device (TSD) (with or without display functionality). In certain of the diagrams, the DSCs 28 are shown as interfacing with electrodes of a panel or touchscreen display (e.g., via interface 86 that couples to row electrodes and another interface 86 that couples to column electrodes). Note that the number of lines that coupled the one or more processing modules 42 to the respective one or more DSCs 28, and from the one or more DSCs 28 to the respective interfaces 86 may be varied (e.g., such as may be described by n and m, which are positive integers greater than or equal to 1). Note that the respective values may be the same or different within different respective embodiments and/or examples herein. Also, in other diagrams, the DSCs 28 are shown as interfacing with electrodes that are implanted within a bodily portion of the subject or implemented in a non-invasive manner such that electrodes are in close proximity or in contact with the surface of a bodily portion of the subject. In even other diagrams, the DSCs 28 are shown as interfacing with electrodes that coupled to one or more sensing and/or stimulation points within the sheath that is operative to facilitate sensing and/or stimulation to a bodily portion of the subject. Note that such a sensing and/or stimulation signal provided from a DSC 28 may be tuned to have any desired electrical characteristics (e.g., amplitude, phase, frequency, wave shape, etc.). For example, consider an electrical stimulation implementation, the electrical signaling provided from the DSC 28 may be tuned to provide for optimal effect and performance when interacting with a bodily portion of the subject.

Note that the same and/or different respective signals may be driven simultaneously sensed by the respective one or more DSCs 28 that couple to electrodes 1410 within any of the various embodiments and/or examples herein. In some examples, a common signal (e.g., having common one or more characteristics) is implemented in accordance with self signaling, and different respective signals (e.g., different respective signals having one or more different characteristics) are implemented in accordance with mutual signaling as described below. Again, as mentioned above, note that the different respective signals that are driven and simultaneously sensed via the electrodes 1410 may be differentiated from one another.

FIG. 16A is a schematic block diagram of another embodiment 1601 of a DSC configured simultaneously to drive and sense a drive signal to an electrode 1410 in accordance with the present invention. In this diagram, one or more processing modules 42 is configured to communicate with and interact with a drive-sense circuit (DSC) 28-16*a*. The one or more processing modules 42 is coupled to a DSC 28-16*a* and is operable to provide control to and support communication with the DSC 28-16*a*. Note that the one or more processing modules 42 may include integrated memory and/or be coupled to other memory. At least some of the memory stores operational instructions to be executed by the one or more processing modules 42. In addition, note that the one or more processing modules 42 may interface with one or more other devices, components, elements, etc. via one or more communication links, networks, communication pathways, channels, etc.

In this diagram, the one or more processing module 42 is configured to provide a reference signal to one of the inputs of a comparator 1615. Note that the drive signal provided to the electrode 1410 is implemented to track, follow, match, etc. the reference signal provided to the one of the inputs of the comparator 1615. As the drive signal provided to the electrode 1410 may be affected based on one or more electrical characteristics of the electrode 1410 including any change thereof, the DSC 28-16*a* is configured to adapt the drive signal to track, follow, match, etc. the reference signal. Note that the comparator 1615 may alternatively be implemented as an operational amplifier in certain embodiments. The other input of the comparator 1615 is coupled to provide a drive signal directly from the DSC 28-16*a* to the electrode 1410. The DSC 28-16*a* is configured to provide the drive signal to the electrode 1410 and also simultaneously to sense the drive signal and to detect any effect on the drive signal including any change of the drive signal based on one or more electrical characteristics of the electrode 1410.

The output of the comparator 1615 is provided to an analog to digital converter (ADC) 1660 that is configured to generate a digital signal that is representative of the effect on the drive signal that is provided to the electrode 1410. In addition, the digital signal is output from the ADC 1660 is fed back via a digital to analog converter (DAC) 1662 to generate the drive signal is provided to the electrode 1410. In addition, the digital signal that is representative of the effect on the drive signal is also provided to the one or more processing modules 42. The one or more processing modules 42 is configured to provide control to and be in communication with the DSC 28-16a including to adapt the drive signal is provided to the comparator 1615 therein as desired to direct and control operation of the electrode 1410 via the drive signal.

FIG. 16B is a schematic block diagram of another embodiment 1602 of a DSC configured simultaneously to drive and sense a drive signal to an electrode 1410 in accordance with the present invention. In this diagram, one or more processing modules 42 is configured to communicate with and interact with a drive-sense circuit (DSC) 28-16b. The one or more processing modules 42 is coupled to a DSC 28-16b and is operable to provide control to and support communication with the DSC 28-16b. Note that the one or more processing modules 42 may include integrated memory and/or be coupled to other memory. At least some of the memory stores operational instructions to be executed by the one or more processing modules 42. In addition, note that the one or more processing modules 42 may interface with one or more other devices, components, elements, etc. via one or more communication links, networks, communication pathways, channels, etc.

This diagram has some similarities to the previous diagram with at least one difference being that this diagram excludes the DAC 1662 of the prior diagram. In this diagram, within the DSC 28-16b the analog output signal from the comparator 1615 is fed back directly to the input of the comparator 1615 that is also coupled to the electrode 1410 thereby providing the drive signal (and simultaneously sensing the drive signal) that is provided to the electrode 1410.

Figure 17:
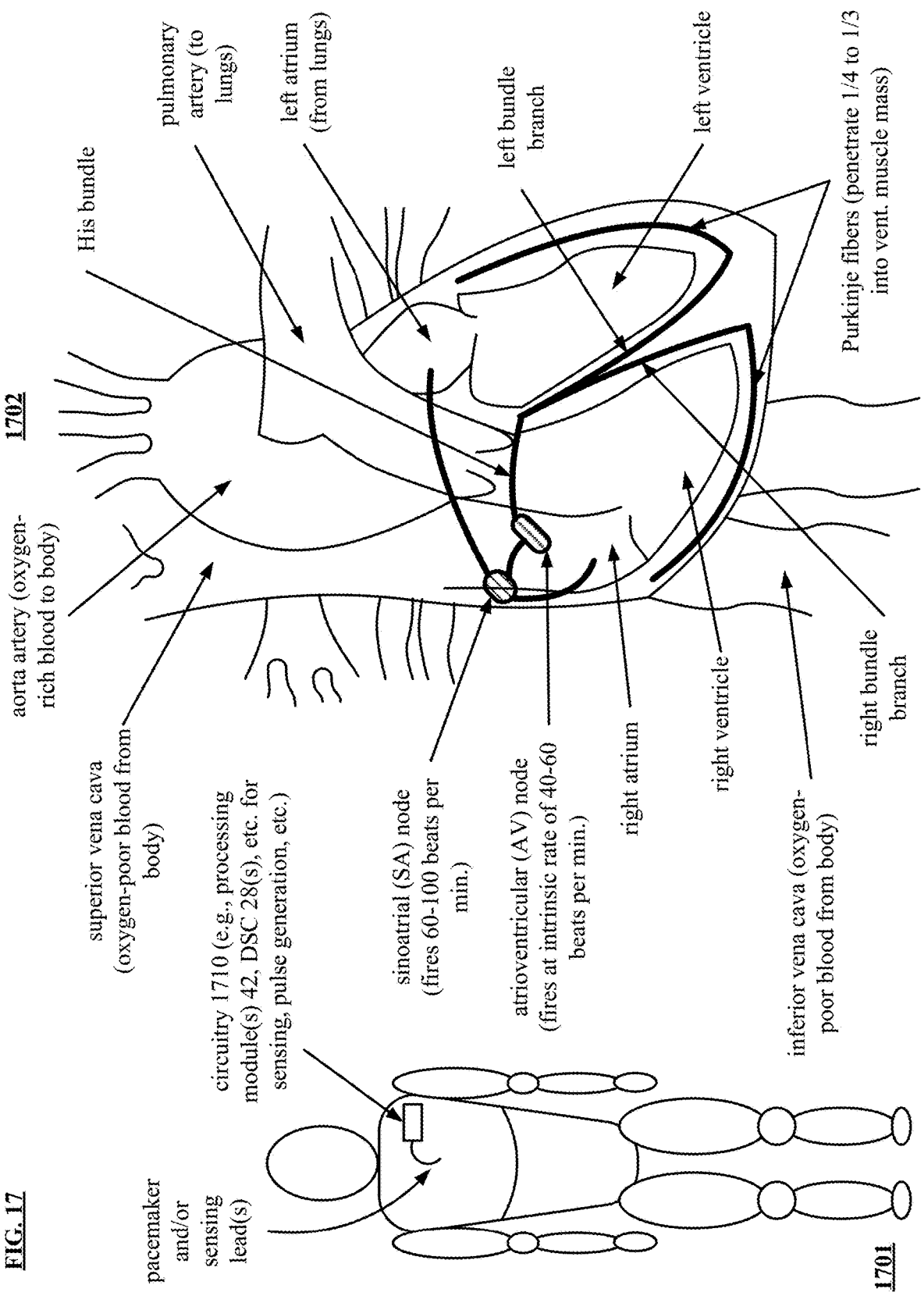
FIG. 17 is a schematic block diagram of an embodiment of circuitry that is operative in accordance with one or more pacemaker and/or sensing leads associated with a subject and also includes a pictorial representation of portions of the heart of the subject in accordance with the present invention.

FIG. 17 is a schematic block diagram of an embodiment of circuitry that is operative in accordance with one or more pacemaker and/or sensing leads associated with a subject 1701 and also includes a pictorial representation 1702 of portions of the heart of the subject in accordance with the present invention. On the left-hand side of the diagram, a subject 1701 is shown as being associated with circuitry 1710 and one or more pacemaker and/or sensing leads. In certain examples, circuitry 1710 includes one or more processing modules 42 that are in communication with one or more DSCs 28 that service the one or more pacemaker and/or sensing leads. In some implementations, the circuitry 1710 is implanted inside the body of the subject. In other implementations, the circuitry 1710 is included mounted on the subject in a noninvasive manner such that the circuitry 1710 baby readily access for maintenance, adjustment, configuration, etc. Even within implementations in which the circuitry 1710 is implanted inside the body of the subject, wireless communication means including our radio frequency (RF), near-field communication (NFC), etc. may be used to facilitate communication with the circuitry 1710 from one or more other devices that are externally located to the body of the subject.

On the right-hand side of the diagram, a pictorial representation 1702 of portions of the heart of the subject is shown. With respect to the blood flow within the heart, oxygen-poor blood is received from the body via the superior vena cava, the blood then travels to the right ventricle and subsequently via the pulmonary artery to the lungs where the oxygen-poor blood is oxygen enriched thereby generating oxygen-rich blood. This oxygen-rich blood is subsequently received via the left atrium from the lungs and enters the left ventricle after which it is returned to the body via the aorta artery. In addition, there are various portions of the heart that include conductive cells that are capable of carrying electrical signals including electrical impulses from one portion of the heart to another.

In addition, with respect to these conductive cells within the hearts, they will undergo both depolarization and repolarization in accordance with facilitating beating of the heart. Generally speaking, to primary chemicals provide the electrical charges within the hearts, namely, sodium (Na+) and potassium (K+). Considering a conductive cell, when that cell is resting, the majority of the potassium is on the inside of the conductive cell and the majority of the sodium is on the outside of the cell. Because of this to take their distribution, the conductive cell is negatively charged or may be viewed as a negative or polarized conductive cell at rest. However, when the conductive cell becomes depolarized, the interior of the conductive cell gains a net positive charge thereby causing the conductive cell to contract. Depolarization is the opposite operation of polarization in which the potassium moves out of the center of the conductive cell and sodium moves across the cell membrane thereby replacing the potassium within the cell gains the net positive charge thereby causing the conductive cell to contract.

During depolarization process, an electrical wave travels through the myocardium of the conductive cells, and the response of the conductive cells within the hearts to this electrical wave causes them to gain the net positive charge thereby causing the conductive cells to contract. To prepare for a subsequent depolarization process, these conductive cells undergo repolarization to return back to the electrical charges of their original state. In order for the conductive cells to perform the depolarization process whereby they gain the net positive charge thereby causing the conductive cells to contract, those conductive cells must undergo a repolarization so that the process may be performed for the next heartbeat. Generally speaking, this process of positive charging of the conductive cells in accordance with depolarization, thereby causing the appropriate portions of the heart to contract in the appropriate timely manner, and the subsequent return of those conductive cells to their original state in accordance with repolarization may be viewed as the depolarization-repolarization process.

Within the heart, these conductive cells are arranged in a system of electrical pathways called the cardiac conduction system (e.g., the conduction system of the heart). The proper generation, timing, and delivery of electrical impulses between different respective portions of the heart within this cardiac conduction system facilitate the beating of the heart. As can be seen within the pictorial representation 1702 of portions of the heart of the subject, the cardiac conduction system includes a sinoatrial (SA) node (alternatively referred to as the sinus node), an atrioventricular (AV) node, the bundle of His (alternatively referred to as the His bundle or the common bundle), right and left bundle branches, and Purkinje fibers. Note that the AV node and the His bundle are often referred to as the AV junction. In addition, note that the Purkinje fibers penetrate into the muscle mass of the left and right ventricles, approximately ¼ to ⅓ the way into the muscle mass of the left and right ventricles.

In an example of operation of a heartbeat of the subject 1701, oxygen-poor blood is received by the heart from the body and undergoes certain processes to enrich the oxygen-poor blood thereby producing oxygen-rich blood which is then delivered to the body. When performing this operation, the heart may be viewed as being an electrical and mechanical system such that the electrical and mechanical components thereof operate cooperatively. That is to say, there are two distinct components of this process to facilitate the contraction, oxygen enriching, and pumping of the oxygen-rich blood out from the heart and back to the body. The heart operates in cooperation with the lungs that perform the oxygen enrichment of the oxygen-poor blood that is received from the body thereby generating the oxygen-rich blood that is provided back to the body. In accordance with this operation, electrical impulses are provided to particular portions of the heart, and that particular portion of the heart responds to that electrical impulse thereby providing a mechanical response based on the electrical impulse. The muscles of the heart respond mechanically by beating or contracting in response to such electrical stimulation provided by such electrical impulses. When such mechanical beating or contraction occurs within the heart, the heart of the subject 1701 will generate both a heart rate and a blood pressure based on such response.

These electrical impulses provided via the respective and proper pathways within the heart cause the heart to beat through process often described as automaticity. Within the body, when operating based on such automaticity, these specialized cells that have conductive capabilities, transmit and/or receive electrical impulses, such as the generation and discharge of electrical current between different respective portions of the heart. In a healthy subject 1701, such electrical impulses are generated by the body and transmitted and received through the different portions of the heart to facilitate the beating of the heart.

Specifically, within a healthy subject 1701, in accordance with the appropriate timing of different respective electrical impulses that are provided via conductive cells of the heart, the heart facilitates the operation of receiving oxygen-poor blood from the body via the superior vena cave. This auction-poor blood enters the right atrium, which is the upper right chamber of the heart. The SA node is a group of specialized conductive cells of the heart that are located in the posterior wall of the right atrium near the superior vena cava via which the oxygen-poor blood is received from the body. The SA node operates as the natural pacemaker of the cardiac system and generates and transmits an electrical impulse that triggers atrial depolarization and contraction. When the SA node generates and transmits this electrical impulse, a wave of the conductive cells begins to depolarize. This electrical depolarization results in the mechanical contraction of certain portions of the heart. For example, this electrical impulse from the SA node is provided to both the right and left atria of the hearts. The impulse travels through the atria via inter-nodal electrical pathways down to the AV node. In a typical healthy subject 1701, the SA node typically generates these electrical impulses and transmits them at a rate of 60-100 beats per minute (bpm).

These electrical impulses that are generated and transmitted from the SA node are received at the AV node and the AV junction. The AV node is another group of specialized conductive cells of the heart that are located in the lower portion of the right atrium, above the base of the valve between the right atrium and the right ventricle, which is the tricuspid valve. The AV node does not possess pacemaker capability as do the conductive cells within the SA node. The AV node operates to receive an electrical impulse from the SA node and to delay them in order to allow the atria of the heart to contract thereby failing the ventricles with blood. In addition, in response to the electrical impulse provided from the SA node, the AV node operates to receive that electrical impulse and conduct it down to the right and left ventricles of the heart via the AV junction and the His bundle.

As the electrical impulse is received in the His bundle from the AV node, the electrical impulse enters into the His bundle that is located in the upper portion of the intraventricular septum. In addition, the His bundle connects the AV node to the left and right bundle branches within the cardiac conduction system. The His bundle operates to direct the electrical impulse down both the left and right bundle branches, and the left and right bundle branches further divide the electrical impulse into the Purkinje fibers of the left and right ventricles of the heart. In a typical healthy subject 1701, the AV node typically generates these electrical impulses and transmits them at a rate of 40-60 bpm.

Note that any problems or deficiencies with respect to the conductivity of the various conductive cells within the heart will result in abnormal operation of the heart, health problems, potential heart attack, and possibly loss of life. For example, ineffectual electrical conductivity between the His bundle in the left and right bundle branches may result in dysrhythmia, which is often associated with congestive heart failure resulting from abnormality in the normal rhythm of the heart. In addition, note that any problems or ineffectual operation of the SA node can cause sinus dysrhythmia.

Figure 18:
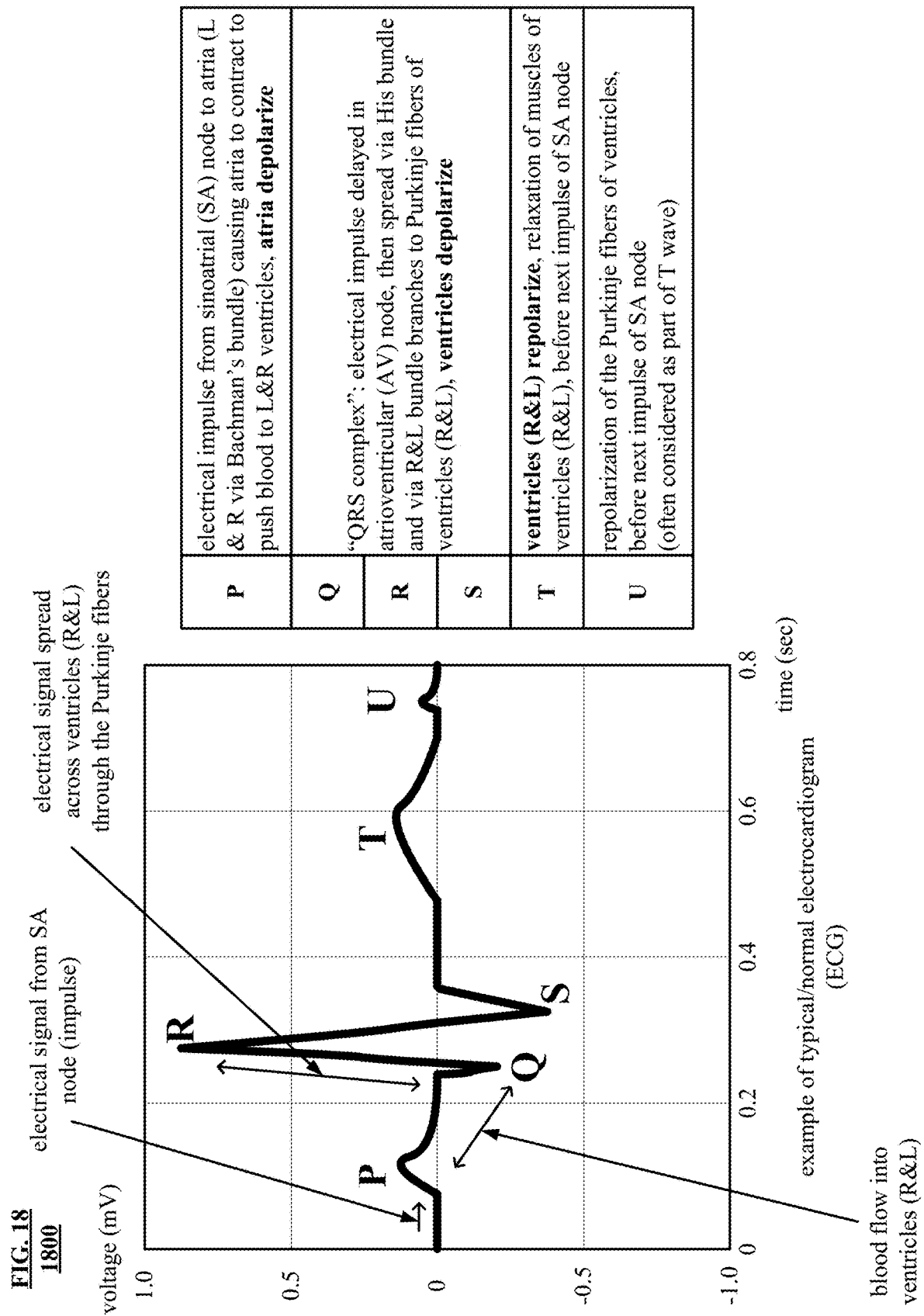
FIG. 18 is a schematic block diagram showing an example of a typical/normal electrocardiogram (ECG) (alternatively referred to as an EKG) in accordance with the present invention.

FIG. 18 is a schematic block diagram showing an example 1800 of a typical/normal electrocardiogram (ECG) (alternatively referred to as an EKG) in accordance with the present invention. Oftentimes the subject visiting a medical professional undergoes testing during a stress test such that the medical professional monitors the ECG of the subject during the stress test (e.g., such as the subject walking on the treadmill, an inclined treadmill, stair master, etc. and/or some other exercise equipment) to see how the subject is responding and how the cardiovascular system of the subject is working. As described above, the heart may be viewed as being an electrical and mechanical system such that the electrical and mechanical components thereof operate cooperatively. When there is a problem with one or both of the electrical and mechanical components of the heart, this electrical and mechanical system may not operate properly. This diagram shows an example of normal operation of the heart based on the associated ECG. For example, when there is abnormality, poor electrical conduction or no conduction, disruption of the one or more components of the cardiac conduction system, etc., then the result may be problems with respect to the heart rate being too slow or too fast, or it may disrupt the function of the heart altogether thereby causing significant risk to health and/or loss of life. Note that even in a healthy subject, sometimes problems may arise with respect to the cardiac conduction system such that the electrical signals have difficulty propagating through the portions of the heart. In addition, note that non-electrical related problems with the heart may result in causing problems within the cardiac conduction system thereby inhibiting the transmission of electrical impulses via the different respective portions of the heart.

On the left-hand side of this diagram, the ECG shows the electrical response of the heart, which may be recorded by placing electrodes on the chest and/or back of the subject. Note that while an ECG may be recorded using prior art ECG technology, ECG stickers placed on a subject that our service using DSCs as described herein can provide significantly improved resolution and accuracy of the electrical response of the heart compared to prior art ECG technology. Electrical response of the heart is shown as an electrical signal having a varying voltage as a function of time in response to these electrical signals that propagate through the various portions of the heart thereby producing the mechanical response of the muscles of the heart and the movement of blood through the heart and lungs within the cardiovascular system.

In an ECG of a healthy subject, the respective portions of the electrical response of the heart are often described with respect to a PQRSTU response to identify the different waves/areas/portions of the ECG. As the electrical signal is provided from the SA node, a P wave is generated within the ECG. During the P wave, the electrical impulses provided from the SA node to the left and right atria via the Bachman's bundle thereby causing the atria to contract to push the lead to the left and right ventricles. Also, during this process, the atria depolarize in accordance with this contraction.

Next is the QRS complex. This is representative of the process by which the electrical impulse is delayed within the AV node, and then spread via the His bundle and via the right and left bundle branches to the Purkinje fibers of the left and right ventricles. Also, during this process, the ventricles depolarize in accordance with their contraction.

Next is the T wave and the U wave, and note that often the U wave is considered to be part of the T wave. During the T wave, the left and right ventricles repolarize such that the muscles of the left and right ventricles relax in preparation for the next impulse to be delivered from the SA node to the AV node in accordance with the next heartbeat. In addition, during the U wave, the Purkinje fibers of the left and right ventricles of the heart undergo repolarization in preparation for the next impulse to be delivered from the SA node to the AV node in accordance with the next heartbeat.

With respect to these different electrical impulses that propagate through different respective portions of the heart in accordance with the heart going through a heartbeat cycle, a DSC as described herein servicing a pacemaker lead or a sensing lead is operative to detect such electrical impulses, including the electrical impulses provided from the sinoatrial (SA) node to the atria, the electrical impulses provided from the SA node to the atrioventricular (AV) node, the electrical impulses that subsequently spread from AV node via the His bundle and the right and left bundle branches to the Purkinje fibers of the right and left ventricles. In addition, note that a DSC as described herein the services a single pacemaker lead is operative both to deliver impulses of the pace signal and to sense cardiac response via one single conductor of a pacemaker lead. As such, a pacemaker lead, when serviced by a DSC as described herein, may include as few as one single conductor and be able to effectuate both delivery of the pacemaker signal as well as sensing of cardiac response including any of the various electrical impulses that propagate through the heart during a heartbeat cycle. Note that certain constructed pacemaker leads have characteristics of an inductive load. As such, a pacemaker lead having such inductive load type characteristics, when serviced by a DSC as described herein, may detect inductive reactants characteristics associated with the pacemaker lead. However, using a DSC as described herein allows for very pacemaker leads designed differently than those currently employed in the prior art. For example, new pacemaker leads may alternatively be designed that do not have such inductive load type characteristics and yet still be serviced and operative in cooperation with the DSC to provide a pace signal including the electrical impulses thereof.

In an example of operation and implementation, a DSC as described herein is configured to perform simultaneous delivery of the impulses of the pace signal and also to sense cardiac electrical activity of the cardiac conduction system of the subject. Note that this operation will be performed via a singular pacemaker lead that is serviced by such a DSC. The cardiac electrical activity of a subject is often described as being based on myocardial signals. Whereas the prior art pacemaker circuit includes a sensor technology that is separate and independent from the signal generation and delivery system, a pacemaker lead serviced by a DSC as described herein includes capability to perform both delivery of the impulses of the pace signal and also to sense the cardiac electrical activity of the cardiac conduction system of the subject via a singular pacemaker lead. Note that such an implementation of it pacemaker lead serviced by a DSC as described herein includes capability both to deliver impulses of the pace signal and also to sense cardiac electrical activity via the same pacemaker lead providing a significant improvement over prior art pacemaker technology. For example, prior art pacemaker technology often uses electrocardiogram (ECG) (alternatively referred to as an EKG) sensing capability to monitor cardiac electric activity as an entirely separate component of such a system. That is to say, prior art pacemaker technology, when performing sensing of cardiac electric activity operate using different components, elements, or a pacemaker lead including multiple conductors or elements such that one of the conductors or elements is implemented to perform delivery of the pace signal, and another of the conductors or elements is implemented to facilitate sensing of cardiac electrical activity. A pacemaker system as described herein such that pacemaker functionality and also cardiac electrical activity sensing functionality may be provided to a subject via a pacemaker lead that is serviced by a DSC is much less intrusive to a subject then prior art techniques. For example, the form factor or size of a pacemaker lead including multiple conductors or elements is much larger than a singular pacemaker lead serviced by a DSC as described herein that is operative to provide both pacemaker functionality and also cardiac electrical activity sensing functionality.

In addition, note that while the signal levels shown in this diagram are within the typical range, such signal levels may vary from subject to subject. Also, while examples of common ranges of pacing impulse signals for electrical capture are also described herein, such as with reference to FIG. 22, note that different hearts of different subjects may require different amounts of energy to elicit depolarization and contraction of the heart in accordance with proper cardiac function. For example, the current levels typically provided within such pacing impulse signals is within the range of milliamps (mA), note again that different parts of different subjects may require different amounts of energy to facilitate proper cardiac function. Examples of parameters that can affect the amount of energy required may include any of a number of the position of the pacemaker lead, how well it is in contact with viable myocardial tissue/conductive cells of the heart, any underlying or pre-existing condition of the subject, any medications currently being administered to the subject, etc.

In another example of operation and implementation, a DSC that services a pacemaker lead as described herein is configured to provide delivery of the impulses of a pace signal and also to sense cardiac electrical activity during the delivery of the impulses of the pace signal. Whereas prior art cardiac electrical activity sensing functionality that is implemented based on prior art pacemaker technology suffers from electrical saturation during the delivery of the impulses of the pace signal and is unable to perform sensing of cardiac electrical activity during the delivery of the impulses of the pace signal, a DSC that services a pacemaker lead as described here and is configured to sense cardiac electrical activity during delivery of the impulses of the pace signal while delivering the impulses of the pace signal. This provides significant improvement over prior art pacemaker technology that is unable to perform the detection of the cardiac electrical activity during that particular time of delivery of an impulse of the pace signal. This cardiac electrical activity sensing functionality, during the delivery of an electrical impulse of the pace signal, that is enabled using a DSC that services a pacemaker lead is described herein provides additional information to medical professionals to understand and diagnose cardiac operation of the subject that is not available using prior art cardiac electrical activity sensing functionality that is implemented based on prior art pacemaker technology.

In yet another example of operation and implementation, operational adaptation of a DSC that services a pacemaker lead as described herein may be performed based on continuous monitoring of cardiac electrical activity of the subject including during delivery of the electrical impulses of the pace signal. For example, one or more processing modules into an indication with the DSC that services a pacemaker lead as described herein is operative to adjust any one or more operational parameters of the DSC that is providing electrical impulses of the pace signal via the pacemaker lead based on information that is acquired via the cardiac electrical activity sensing functionality that is enabled by such an implementation as described herein (e.g., DSC that services a pacemaker lead). For example, the one or more processing modules is configured to facilitate adjustment of any one or more of the various electrical characteristics of the pace signal that is delivered from the DSC via the pacemaker lead including any one or more of voltage and/or current magnitude of the electrical impulses of the pace signal, the pulse width of electrical impulses of the pace signal, the total amount of energy and/or current delivered via the electrical impulses of the pace signal, the frequency or rate of the electrical impulses of the pace signal, etc.

Figure 19:
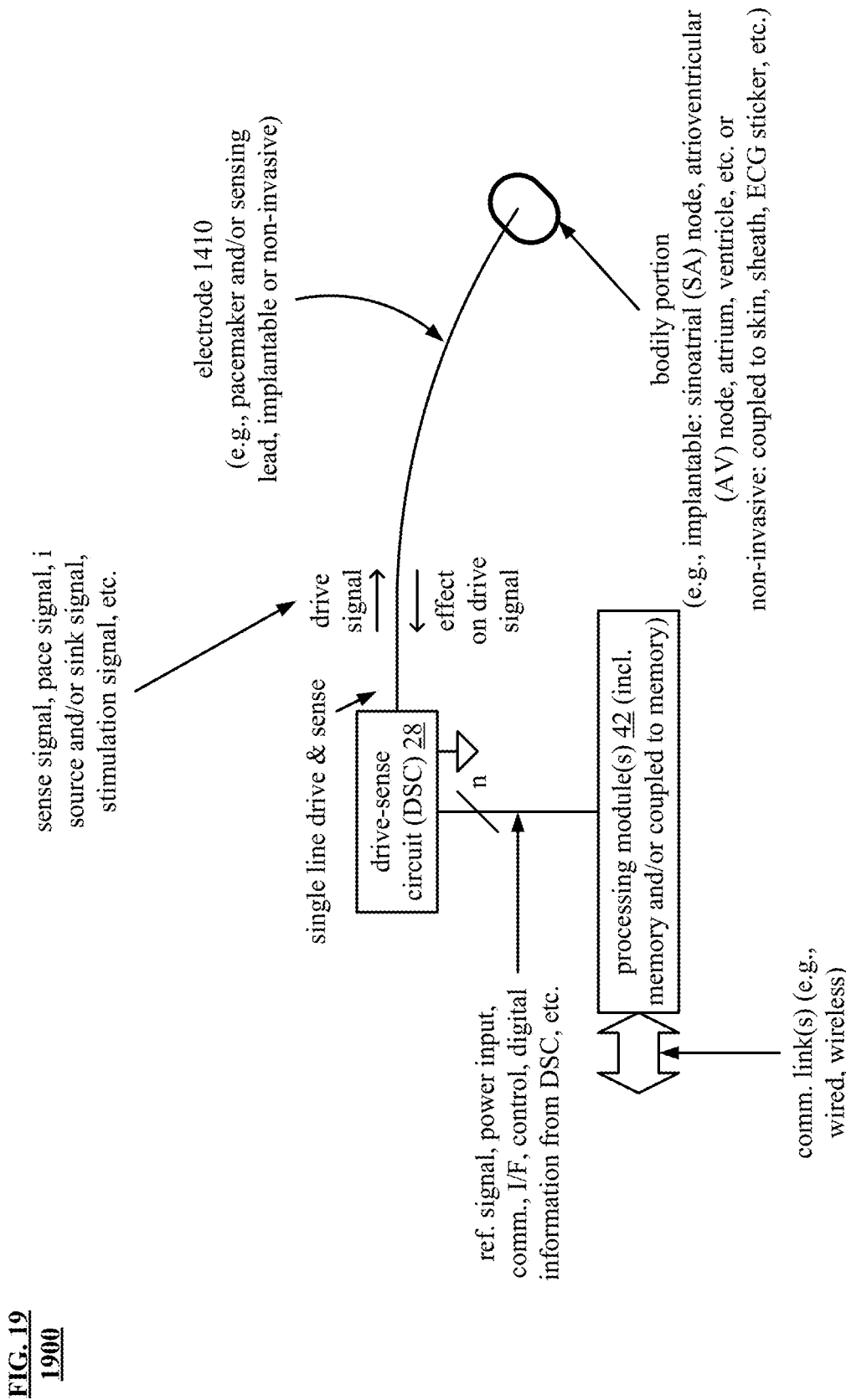
FIG. 19 is a schematic block diagram of another embodiment of a DSC configured simultaneously to drive and sense a drive signal to an electrode in accordance with the present invention.

FIG. 19 is a schematic block diagram of another embodiment 1900 of a DSC configured simultaneously to drive and sense a drive signal to an electrode in accordance with the present invention. As with many diagram herein, this diagram shows one or more processing modules 42 configured to interact with a drive-sense circuit (DSC) 28. In this diagram and others, note that the coupling or connection between one or more processing modules 42 and the DSC 28 may be made using any number of communication channels, pathways, etc. (e.g., generally n, where n is a positive integer greater than or equal to 1).

Examples of one or more signals that may be provided between the DSCs 28 and the one or more processing modules 42 to the DSC may include any one or more of a reference signal such as provided from the one or more processing modules 42 to one or more of the DSCs 28 (e.g., referred to as Vref in certain diagrams), power input, communication signaling, interfacing, control signaling, digital information provided from the DSC 28 to the one or more processing modules 42, digital information provided from the one or more processing modules 42 to the DSC 28, etc. In some examples, the DSC 28 itself includes a signal generator whose operation is controlled by the one or more processing modules 42 such as setting one or more parameters of the reference signal to be generated and used as a basis to generate the drive signal. In addition, note that the one or more processing modules 42 may interface with one or more other devices, components, elements, etc. via one or more communication links, networks, communication pathways, channels, etc. that may be implemented in any of a number of ways including wired communication media, wireless communication media, optical communication media, and/or any other type of communication media.

The DSC 28 is implemented to generate a drive signal based on a reference signal into provided via a single line via an electrode 1410 to facilitate sensing and/or stimulation to a bodily portion of a subject. In one example, the electrode 1410 is implemented as a pacemaker lead to facilitate the delivery of a pacing signal to a bodily portion of the subject, such as to a particular location within the heart (e.g., in accordance with atrial and/or ventricle pacing of the heart of the subject). In another example, the electrode 1410 is implemented as a sensing lead that is operative to detect one or more electrical signals that are transmitted through conductive cells of the subject (e.g., such as the electrical signals transmitted via respective portions of the heart in accordance with a heartbeat cycle of the subject). In yet another example, the electrode 1410 is implemented as a sensing lead is operable to detect impedance of a bodily portion of the subject (e.g., such as impedance of the heart of the subject, a particular of the subjects such as the chest or thorax, and/or other bodily portion of the subject etc.). In yet another example, the electrode 1410 is implemented as connection between the DSC and a point with any sheath that may be in contact with or wrapped around a bodily portion of the subject. In some implementations, the sheath includes multiple points that are in contact with or wrap-around a portion of the subject to facilitate sensing and/or stimulation based on the particular arrangement and location of those points.

Note that the electrode 1410 may be implemented in a variety of ways with respect to a subject. In one implementation, the electrode is implanted within the subject. For example, in accordance with the electrode 1410 operating as a pacemaker lead, the pacemaker lead is implanted within the body of the subject and particularly placed at a desired location, typically within a particular portion of the heart so as to facilitate proper function of the heart of the subject based on the appropriate delivery of a pacing signal. In one example, an implantable electrode 1410 that is implemented to facilitate atrial pacing is implanted into or near the sinoatrial (SA) node of the heart of the subject. In another example, an implantable electrode 1410 that is implemented to facilitate ventricle pacing is implanted into or near the atrioventricular (AV) node of the heart of the subject. Anything other examples, and implantable electrode 1410 that is implemented to facilitate pacing is implanted into or near the atrium (e.g., the right atrium) or a ventricle (e.g., the left or right ventricle) of the heart of the subject.

In another implementation, the electrode is associated with the subject in a non-invasive manner. For example, in accordance with the electrode 1410 operating as a non-invasive pacemaker lead, the pacemaker lead is external to the body of the subject, yet in contact with or associated with the subject at a location associated with the bodily portion, or within sufficient proximity to the subject at a location associated with the bodily portion, such as on the surface of the skin of the subject, that will facilitate delivery of a pacing signal through the surface of the skin of the subject to the appropriate portion of the heart so as to facilitate proper function of the heart of the subject based on the appropriate delivery of a pacing signal. In another example, in accordance with the electrode 1410 operating to facilitate sensing of an electrocardiogram (ECG) (alternatively referred to as an EKG) of the subject, the electrode 1410 couples the DSC 28 is coupled via the electrode 1410 to an ECG sticker that is in contact with surface of the skin of the subject at a location associated with the bodily portion (e.g., chest, the thorax, near the heart of the subject, etc.).

In addition, with respect to different implementations of the electrode 1410 that are tailored to facilitate sensing and/or stimulation, note that the electrode 1410 may be implanted within the subject or non-invasive with respect to the subject such that the electrode 1410 is associated with or in contact with the surface of a bodily portion of the subject.

Note that this implementation of a DSC 28 that is configured to drive a signal and simultaneously sense that signal including any effect, change, modification, etc. of that signal may be implemented to perform different functions in different implementations. Examples of different types of signals that may be provided from the DSC 28 via the electrode 28 include one or more of a sense signal, a pace signal, a current source signal, a current sink signal, a combination current source/sink signal, a stimulation signal, etc. note that this configuration of one or more processing modules 42 in communication with a DSC 28 that services and electrode 1410 may be configured to operate differently for different purposes as may be desired in different applications.

Note that such an embodiment including a DSC 28 that services and electrode 1410 that is in proximity to or in contact with the bodily portion of the subject may be used for any a variety of purposes including delivery of a pace signal, nerve stimulator, muscle stimulator, impedance sensor, etc. Also, only sensing, only stimulation, or both sensing and stimulation may be performed via a single electrode 1410 that is serviced by a DSC 28. Such an implementation provides the ability to perform the dual functionality of both sensing and stimulation via a single electrode 1410 having a very small form factor, size, etc. In addition, the reference signal that is employed by the DSC 28 may any desired type and form (e.g., DC signal, square wave signal, triangle wave signal, sawtooth signal, etc., as just some examples of types and waveforms of signals, etc.). Generally speaking, any of the various aspects, embodiments, and/or examples of the invention (and/or their equivalents) (e.g., including one or more DSCs that service one or more elements such as electrodes, pacemaker leads, conductive points such as in a sheath, etc.) may be implementation to perform any one or more variety of operations including delivery of a pace signal, nerve stimulation, muscle stimulation, sensing of various electrical characteristics including voltage, current, and/or impedance, etc.

Figure 20:
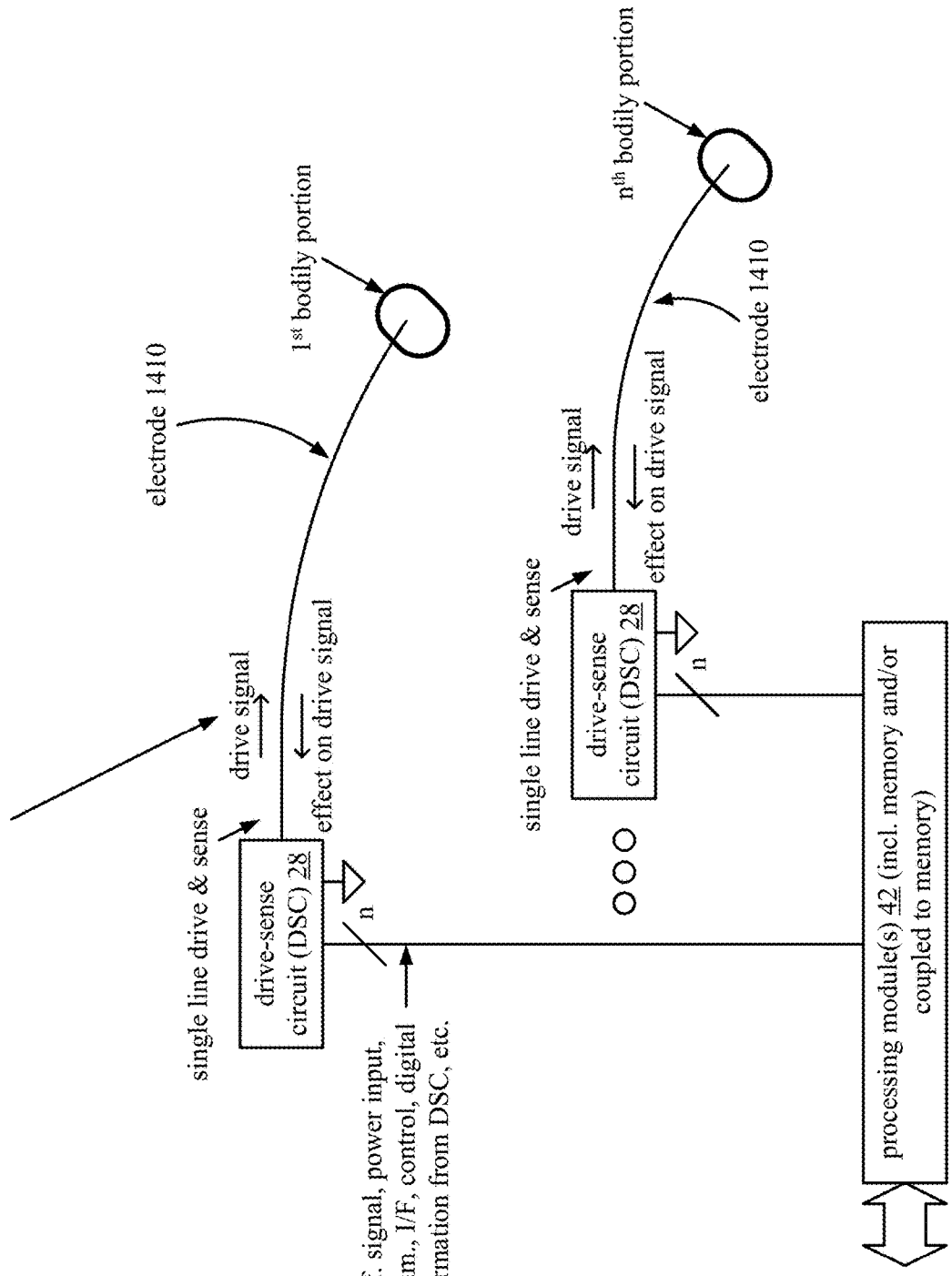
FIG. 20 is a schematic block diagram of an embodiment of multiple DSCs configured simultaneously to drive and sense drive signals to electrodes, respectively, in accordance with the present invention.

FIG. 20 is a schematic block diagram of an embodiment 2000 of multiple DSCs configured simultaneously to drive and sense drive signals to electrodes, respectively, in accordance with the present invention. This diagram has similarity to the prior diagram yet includes multiple DSCs 28 that service respective electrodes 1410 may be associated with different respective bodily portions. For example, a first DSC 28 is coupled via an electrode 1410 to a first bodily portion, and one or more additional DSCs are coupled via respective electrodes 1410 to other bodily portions, as shown by a DSC 28 that is coupled via an electrode 1410 to an nth bodily portion. Generally speaking, any desired number of respective DSCs maybe implemented to service any desired number of electrodes 1410 that are associated with different respective bodily portions.

Note that such a multiple DSC 28 and electrode 1410 implementation may be implemented using any number of different types of electrodes 1410 for different purposes. Examples of such different respective purposes may be associated with providing pace making to a subject, stimulation to one or more bodily portions of the subject, sensing of one or more electrical characteristics such as electrical signals via conductive cells, impedance, etc. of the subject. Examples of different types of signals that may be delivered by the different respective DSCs 28 include any one or more of delivery of a sense signal, a pace signal, a current source signal, a current sink signal, a stimulation signal, and/or any other type of signal. Note also that such a multiple DSC 28 and electrode 1410 implementation may include any combination of one or more implantable electrodes 1410 and/or non-invasive electrodes 1410.

In an example of operation and implementation, a first electrode 1410 is implanted within the subject to facilitate delivery of a pace signal. A second electrode 1410 is placed within contact of or within sufficient proximity of the surface of the skin of the subject to facilitate stimulation of a bodily portion of the subject be a delivery of a current and/or voltage signal. A third electrode 1410 is implanted within the subject to facilitate measurement of impedance of a particular bodily portion of the subject, such as the heart, the chest or thorax, etc. A fourth electrode 1410 is implemented within a sheath that is in contact with or wrapped around a bodily portion of the subject to facilitate sensing and/or stimulation of that lovely portion of the subject. Generally speaking, any desired implementation of different DSCs 28 and respective electrodes 1410 associated with those different DSCs, such as on a one-to-one basis such that each DSC 28 services a respective electrode 1410, may be made to serve different respective purposes.

FIGS. 21A, 21B, and 21C are schematic block diagrams of embodiments 2101, 2102, and 2103 of different types of pacemakers operable to be serviced by one or more DSCs in accordance with the present invention. There are a variety of different ways in which pace making functionality may be provided to a subject. In some examples, circuitry 1710 is implanted within the subject, and the circuitry 1710 includes various components that may include one or more of one or more processing modules 42, one or more DSCs 28, one or more energy or power sources such as a battery or other storage device, and/or any other components or elements as desired or needed to facilitate various functions including delivery of a pace signal including pulse generation to facilitate the pacing, sensing, and/or any other operations that may be provided to the subject. These diagrams showing certain portions of the heart of the subject may be understood also with reference to FIG. 17 that provides more description of the heart.

Referring to embodiment 2101 of FIG. 21A, this diagram shows a single chamber pacemaker that includes a single pacemaker leads that is provided to a chamber of the heart (e.g., upper or lower chamber) of the subject. This diagram shows an atrial pacemaker lead coupled from circuitry 1710 that is implanted in or near the sinoatrial (SA) node of the heart of the subject. This diagram shows a single chamber pacemaker including a single pacemaker lead. Note that certain implementations of a single chamber pacemaker typically carries electrical impulses to the right ventricle of the heart of the subject. However, a single chamber pacemaker may be alternatively implemented to carry electrical impulses to the sinoatrial (SA) node. This diagram shows a single chamber pacemaker that carries electrical impulses to the SA node.

In an example of operation and implementation, circuitry 1710 is implanted within the body of the subject, and the atrial pacemaker lead (e.g., which may be implemented as an electrode 1410) passes via the superior vena cava of the heart of the subject and is implanted in or near the sinoatrial (SA) node of the heart of the subject. The atrial pacemaker lead delivers a pace signal (e.g., composed of timely delivered electrical impulses) to initiate the SA node that provides an electrical impulse from the SA node to the left and right atria via the Bachman's bundle causing the atria to contract to push the lead to the left and right ventricles and also results in the depolarization of the atria, which generates the corresponding P wave that may be seen when viewing and electrocardiogram (ECG) (alternatively referred to as an EKG) of the subject.

Again, an alternative implementations, a pacemaker lead delivers a pace signal (e.g., composed of timely delivered electrical impulses) to the right ventricle of the heart of the subject to initiate the atrioventricular (AV) node of the heart of the subject and the corresponding QRS complex associated with the electrical signals being spread via the His bundle of the heart (alternatively referred to as the common bundle) and via the right and left bundle branches to the Purkinje fibers of the left and right ventricles of the heart that also results and depolarization of the ventricles.

Referring to embodiment 2102 of FIG. 21B, this diagram shows a dual chamber pacemaker that includes two pacemaker leads that are provided respectively to an upper and a lower chamber of the heart of the subject. In an example of operation and implementation, an atrial pacemaker lead coupled from circuitry 1710 that is implanted in or near the sinoatrial (SA) node of the heart of the subject and also shows a right ventricular lead coupled from circuitry 1710 that implanted in or near the right ventricle of the heart of the subject. This type of pacemaker carries electrical impulses to the right ventricle and also to the right atrium of the heart of the subject and provides the ability to control the relative timing between the respective contractions of the various chambers of the heart of the subject during a heartbeat. For example, this implementation that includes a dual chamber pacemaker provides the ability to control with high precision the initiation of the SA node and also the initiation of the AV node. For example, within certain patients, even though the SA node may be initiated effectively, the electrical signaling via the conductive cells of the heart may be insufficient to initiate the AV node and subsequent electrical signaling via the conductive cells of the heart including the His bundle, the right and left bundle branches to the Purkinje fibers, etc.

Referring to embodiment 2103 of FIG. 21C, this diagram shows a biventricular pacemaker that includes three pacemaker leads that are provided respectively to an upper chamber of both lower chambers of the heart of the subject. In an example of operation and implementation, an atrial pacemaker lead coupled from circuitry 1710 that is implanted in or near the sinoatrial (SA) node of the heart of the subject, a right ventricular lead coupled from circuitry 1710 that implanted in or near the right ventricle of the heart of the subject, and a left ventricular lead coupled from circuitry 1710 that implanted in or near the left ventricle of the heart of the subject. Biventricular pacing is sometimes alternatively referred to as cardiac resynchronization therapy. Often times, this type of pace making is provided to a subject having very severe heart problems including heart failure and/or abnormal electrical system operation of the various conductive cells within the heart. This type of pace making provides the ability to control with high precision the initiation of the SA node (via the electrical impulses provided via the atrial pacemaker lead), the initiation of the AV node (via the electrical impulses delivered via the right ventricle lead), and also the initiation of the repolarization of the left and right ventricles including the relaxation of the muscles of the left and right ventricles before the next electrical impulse is received by the SA node (via the electrical impulses delivered via the left ventricle lead). In addition, the electrical impulses delivered via the left ventricle lead operate to improve the repolarization of the Purkinje fibers of the left and right ventricles of the heart before the next electrical impulse is received by the SA node.

Note that different respective subjects within different degrees of cardiovascular health may be treated differently using different implementations of pace making. This disclosure describes many different implementations by which pace making may be implemented using one or more processing modules 42 and one or more DSCs 28 to provide significantly improved control of signal level, timing, precision, sensing, etc. over existing pacemaker technology. For example, given the complete control of a reference signal is used within a DSC 28 that is configured to generate a pacing signal to be provided to one or more portions of the heart of the subject, a pacing signal having any desired signal level, pulse duration, energy content, current level, voltage level, etc. may be delivered with very high precision and accuracy over existing pacemaker technology.

FIG. 21D is a schematic block diagram of an embodiment of a method 2104 for execution by one or more devices in accordance with the present invention. From certain perspectives, the method 2104 may be viewed as being a method for execution by a pacemaker system. The method 2104 operates in step 2110 by operating a drive-sense circuit (DSC), operably coupled to a pacemaker lead implemented with one single conductor, to receive a reference signal and to generate a pace signal including electrical impulses based on the reference signal. In certain variants of the method 2104, as shown in block 2112, the pacemaker lead is implanted in or in proximity to a sinoatrial (SA) node or a ventricle of a cardiovascular system of a subject. In certain other variants of the method 2104, as shown in block 2114, the pacemaker lead is implanted in or in proximity to a ventricle of a cardiovascular system of a subject.

The method 2104 operates in step 2120 by operating the DSC to provide the pace signal from the DSC via the pacemaker lead to an electrically responsive portion of a cardiac conductive system of the subject to facilitate cardiac operation of the cardiovascular system of the subject. Note that muscles of a heart of the subject produce a mechanical response to the electrical impulses of the pace signal to move blood through the cardiovascular system of the subject.

The method 2104 operates in step 2130 by operating the DSC to sense, via the pacemaker lead, cardiac electrical activity of the cardiovascular system of the subject that is generated in response to the pace signal and electrically coupled into the pacemaker lead. The method 2104 operates in step 2140 by generating a digital signal that is representative of the cardiac electrical activity of the cardiovascular system of the subject that is sensed via the pacemaker lead. In addition, the method 2104 operates in step 2150 by processing the digital signal generated by the DSC to determine the cardiac electrical activity of the cardiovascular system of the subject that is sensed via the pacemaker lead.

Certain other variants of the method 2104 operate by adjusting one or more electrical characteristics of the reference signal to facilitate generation of the pace signal by the DSC to facilitate capture by the cardiac conductive system of the subject in response to the pace signal. Note that adjustment of the one or more electrical characteristics of the reference signal causes adjustment of at least one electrical characteristic of the pace signal including at least one of a magnitude of the electrical impulses of the pace signal, a pulse width of the electrical impulses of the pace signal, an amount of current level delivered via the electrical impulses of the pace signal, and/or a frequency or rate of the electrical impulses of the pace signal.

Certain other variants of the method 2104 operate by processing the digital signal generated by the DSC to determine the cardiac electrical activity of the cardiovascular system of the subject that is sensed via the pacemaker lead including to determine whether there is capture by the cardiac conductive system of the subject in response to the pace signal. Based on a determination that there is no capture by the cardiac conductive system of the subject, variants of the method 2104 adjusting one or more electrical characteristics of the reference signal to facilitate generation of the pace signal by the DSC to facilitate capture by the cardiac conductive system of the subject in response to the pace signal.

Note that adjustment of the one or more electrical characteristics of the reference signal causes adjustment of at least one electrical characteristic of the pace signal including at least one of a magnitude of the electrical impulses of the pace signal, a pulse width of the electrical impulses of the pace signal, an amount of current level delivered via the electrical impulses of the pace signal, and/or a frequency or rate of the electrical impulses of the pace signal.

Note that the DSCs may be implemented in any of a variety of ways including as described herein in various examples, embodiments, etc. In one example, a DSC is implemented to include a comparator configured to produce an error signal based on comparison of the reference signal to the pace signal. The reference signal is received at a first input of the comparator, and the pace signal is received at a second input of the comparator. The DSC also includes a dependent current supply configured to generate the pace signal based on the error signal and to provide the pace signal via a single line that couples to the pacemaker lead and the second input of the comparator. The DSC also includes an analog to digital converter (ADC) configured to process the error signal to generate the digital signal that is representative of the cardiac electrical activity of the cardiovascular system of the subject that is sensed via the pacemaker lead. Some variants of the method 2104 operate by adjusting a programmable gain of the dependent current supply. Scaling the programmable gain of the dependent current supply provides for scaling of the error signal.

In another example, a DSC is implemented to include a power source circuit operably coupled via a single line to the pacemaker lead. When enabled, the power source circuit is configured to provide an analog signal via the single line coupling to the pacemaker lead. The analog signal includes at least one of a DC (direct current) component or an oscillating component. The DSC also includes a power source change detection circuit operably coupled to the power source circuit. When enabled, the power source change detection circuit is configured to detect an effect on the analog signal that is based on at least one of an electrical characteristic of the pacemaker lead or the cardiac electrical activity of the cardiovascular system of the subject that is sensed via the pacemaker lead and to generate the digital signal that is representative of the cardiac electrical activity of the cardiovascular system of the subject that is sensed via the pacemaker lead.

In some specific examples, the power source circuit is implemented to include a power source to source at least one of a voltage or a current via the single line to the pacemaker lead. The power source change detection circuit is implemented to include a power source reference circuit configured to provide at least one of a voltage reference or a current reference and a comparator configured to compare the at least one of the voltage and the current provided via the single line to the pacemaker lead to the at least one of the voltage reference and the current reference to produce the analog signal.

FIG. 22 is schematic block diagram showing an example 2201 of a typical/normal electrocardiogram (ECG) (alternatively referred to as an EKG) showing typical locations of pacing signals and also includes a pictorial representation 2202 of the relationship between pulse signal impulse amplitude and pulse width duration that facilitate capture and that fail to schematic block in accordance with the present invention.

Referring to the example 2201, this diagram shows, and locations of pacing signals relative to new atypical/normal ECG. For example, when performing atrial pacing only, such as provided to the sinoatrial (SA) node via an atrial pacemaker lead/electrode, an electrical impulse is delivered via the pacemaker lead/electrode which subsequently results in the heart response of the P wave. When performing the ventricle pacing only, such as provided to right ventricle, the pacer spike is typically followed by the QRS complex.

With respect to the electrical characteristics of signals employed in accordance with pace making, the upper right of the diagram shows some common ranges of pacing impulse signals for electrical capture by the elements of the heart in accordance with proper operation of the heart. Capture may be viewed as the minimum electrical stimulus needed to initiate the operation of the heart and the movement of the electrical impulses via the cardiac conduction system that results in the proper operation of the heart. For example, when providing a pace signal that is insufficient, such as in terms of voltage, pulse width, current, etc., then the heart will not capture the signal and will not execute a heartbeat cycle. Referring again to the upper right-hand portion of the diagram, some common characteristics of the pacing impulse signals that commonly result in electrical capture thereby causing the proper operation of the heart may include one or more of a voltage within a voltage threshold range of 0.5 to 2 V (volts), a pulse width within the range of 0.5 to 0.8 ms (milli-secs), a current level within the range of 50 to 90 mA (milli-amps). In addition, such pacing impulse signals are typically delivered at a rate of between 60 and 100 times per minute to facilitate the heart rate of 60 to 100 bpm.

Referring to the pictorial representation 2202 on the right-hand side of the diagram, considering the pace signal impulse threshold in volts along the vertical axis and the pulse width duration in milliseconds along the horizontal axis, there are combinations of the magnitude of the pace signal and the pulse width duration that will facilitate electrical capture and other combinations that results in no electrical capture. For example, to the right-hand side of the dark line, when the magnitude of the pace signal is to the right of the dark line and the pulse width duration is above the dark line, that combination of magnitude of the pace signal and pulse width duration will result in electrical capture thereby causing the proper operation of the heart.

When the magnitude of the pace signal is to the left of the dark line in the pulse width duration is below the dark line, that particular combination of magnitude of pace signal impulse and pulse width duration will not result in electrical capture. Note that the particular line that indicates the demarcation between electoral capture and no electrical capture may be different for different subjects, but generally speaking, this trend such showing combination of the pace signal impulse magnitude and the pulse width duration must be of sufficient value to provide the minimum electrical stimulus needed to facilitate electrical capture of the heart will exist.

As such, when operating a pacemaker to facilitate proper operation of the heart of the subject, adjustment and tuning of the various parameters by which the pacemaker delivers the pacing signal is made to ensure that electrical capture is achieved for a particular patient. A pacemaker implemented as described herein using circuitry that includes a DSC that services one or more pacemaker leads provides much improved resolution and ability to adjust any such parameters of the pacing signal, including any one or more of magnitude, pulse width, energy level, current level, voltage level, signal shape, waveform shape, and/or any other desired parameter in a much improved manner in comparison to prior art pacemaker technology. For example, by using a DSC as described herein to service a pacemaker lead, the current level that may be delivered via the pacemaker lead may be varied between 0 A up to is or 10s of A (or even higher levels, though most likely not needed for pacemaker applications) with extremely fine resolution and accuracy. Again, as described above, a current level within the range of 50 to 90 mA is common for many pacemaker applications, and a DSC that services a pacemaker lead as described herein may be configured and implemented to provide current levels within any desired range as needed within pacemaker applications to assist and facilitate proper cardiac function of the subject.

In one implementation, a DSC is configured to provide any such desired current level with very high resolution and accuracy (e.g., from 0 A to a few microamps to 1 amp or more). Such a DSC is also configured to detect and sense of electrical signals such as those associated with cardiac electrical activity of the subject with very high resolution and accuracy (e.g., from 0 A to a few nanoamps to a few microamps to 1s or 10s of amps or more). Note that the electrical signals associated with cardiac electrical activity of the subject are typically in a lower range than 1s or 10s of amps, and a DSC that services a pacemaker lead and also provides cardiac electrical activity sensing functionality as described herein may be configured and implemented to detect and sense cardiac electrical activity of the subject within any desired range (e.g., from 0 A to a few nanoamps to a few microamps to a few milliamps or more, etc.).

In addition, by using a DSC is described and to service the pacemaker lead, the voltage level that may be delivered via the pacemaker lead may be varied between zero holds up to 1s or 10s of volts (or even higher levels, though most likely not needed for pacemaker applications) with extremely fine resolution and accuracy. In another implementation, DSC is configured to provide any desired voltage level with very high resolution and accuracy (e.g., from zero V to a few microvolts or a few millivolts to 5 V or 10 V). Also, by using a DSC is described and to service the pacemaker lead, the pulse width of a pacing signal that may be delivered via the pacemaker lead may be adjusted to any desired value varied between 0 seconds up to 1s or 10s of microsecs to 1s or 10s of milliseconds (or even longer pulse widths, though most likely not needed for pacemaker applications) with extremely fine resolution and accuracy.

Given the total flexibility by which a reference signal may be generated and used within a DSC as described herein when servicing a pacemaker lead (e.g., such as using signal generator or within one or more processing modules), any of the parameters of the pacing signal may be adjusted to any desired value with extremely fine resolution and accuracy in a manner much improved over prior art pacemaker technology.

FIGS. 23A and 23B are schematic block diagrams of examples of pacing signals that may be used in accordance with the present invention.

Referring to example 2201 of FIG. 23A at the top of the diagram, this shows one possible example of the pacing signal such that the respective electrical impulses are delivered approximately once every second to facilitate beating of the heart at 60 beats per minutes, such that there is one cycle per second, corresponding to a pacing signal having a frequency of 1 Hz. While the voltage magnitude and pulse width of the electrical impulses may vary in different applications as required for different subjects, one example would include electrical impulses having a voltage magnitude of approximately 1.75 V and pulse width of approximately 0.6 ms. Example 2302 of FIG. 23A at the bottom of the diagram shows such an example of an electrical impulse having a voltage magnitude of approximately 1.75 V and pulse width of approximately 0.6 ms in an enlarged view.

Referring to example 2203 of FIG. 23B at the top of the diagram, this shows another possible example of the pacing signal such that the respective electrical impulses are delivered approximately once every second to facilitate beating of the heart at 60 beats per minutes, such that there is one cycle per second, corresponding to a pacing signal having a frequency of 1 Hz. While the current magnitude and pulse width of the electrical impulses may vary in different applications as required for different subjects, one example would include electrical impulses having a current magnitude of approximately 75 mA and pulse width of approximately 0.6 ms. Example 2304 of FIG. 23B at the bottom of the diagram shows such an example of an electrical impulse having a current magnitude of approximately 75 mA and pulse width of approximately 0.6 ms in an enlarged view.

In addition, note that while the electrical impulses described in certain of the previous diagram show square wave electrical impulses, note that alternative waveform shapes may be used as desired. For example, an electrical impulse that has a rising edge that reaches the maximum magnitude of the electrical impulse, and then reduces in value or decays during the pulse width, before returning to zero may alternatively be used. In one possible example, consider the top of the electrical impulse shown in certain of the previous diagrams as not being flat, yet having a different shape during the duration of the pulse width, such as reducing in value from 1.7 V to 1.6 V during the pulse width or reducing in value from 75 mA to 65 mA during the pulse width. Generally speaking, the particular shape of the electrical impulses may be made in accordance with any desired shape using a DSC that is implemented to service a pacemaker lead is described herein.

Again, given the total flexibility by which a reference signal may be generated and used within a DSC as described herein when servicing a pacemaker lead (e.g., such as using signal generator for within one or more processing modules), any of the parameters of the pacing signal including voltage level, current level, pulse width, frequency, shape, etc. may be adjusted to any desired value with extremely fine resolution and accuracy in a manner much improved over prior art pacemaker technology.

FIGS. 24A and 24B are schematic block diagrams of other embodiments 2401 and 2402 of DSCs configured simultaneously to drive and sense drive signals to electrodes, respectively, in accordance with the present invention.

Referring to embodiment 2401 of FIG. 24A, this diagram provides an alternative implementation by which a DSC 28 may be implemented, as shown by DSC 28-24A. As with other embodiments, examples, etc. herein, one or more processing modules 42 is implemented to interact and communicate with the DSC 28-24A in this diagram. Note that the one or more processing modules 42 of this diagram in any other diagram herein may also be in communication with one or more other devices including other sensors. For example, one or more processing modules 42 is in communication with one or more of a temperature sensor, accelerometer, a thermometer, a humidity sensor, a barometer, and/or any other sensor in addition to being in communication with a DSC such as DSC 28-24A in this diagram. Note that the one or more processing modules 42 and/or a DSC such as the DSC 28-24A of this diagram may be in communication with one or more other devices via one or more wired communication links, one or more wireless communication links such as using radiofrequency (RF) communication, near-field communication (NFC), inductive communication link, etc. Considering an implementation in which a device that includes the one or more processing modules 42 and/or a DSC, such as the DSC 28-24A of this diagram, are implanted within a subject, and consider that those devices are powered by a rechargeable battery, note that charging of that battery may be performed using wireless charging such as described in U.S. Utility patent application Ser. No. 16/428,063, entitled "Wireless Power Transfer and Communications,"filed May 31, 2020, pending, and U.S. Utility patent application Ser. No. 16/428,063, entitled "Wireless Power Transfer with In-line Sensing and Control, "filed May 31, 2020.

The DSC 28-24A includes a signal generator 2410 that is configured to receive a control signal from the one or more processing modules 42 that specifies one or more parameters of the reference signal. Examples of one or more parameters of the reference signal may include any one or more of amplitude/magnitude, pulse width, frequency, type, waveform, phase, etc. Note that the reference signal may include more than one frequency in certain implementations. For example, two or more signals may be included within the drive signal that is provided from the DSC 28-24A to serve two or more respective functions such as delivery of pace signal and sensing, among other possibilities. In addition, note that the reference signal may be of any desired type and having any desired waveform. For example, in some examples, the reference signal is a sinusoidal signal such as may be used in accordance with sensing. Note that the reference signal may be any other type of signal including DC signal, square wave signal, triangle wave signal, sawtooth signal, etc., as just some examples of types and waveforms of signals. In accordance with delivering a pacing signal to a subject, the reference signal may be a square wave type signal that includes electrical impulses of a particular magnitude, pulse width, energy level, current level, voltage level, and/or any other desired parameter such that the electrical impulses are delivered at a particular desired frequency (e.g., 60-100 times a minute such as in accordance with facilitating a regular and continuous heartbeat within the subject).

In addition, in this diagram as well as others that pictorially show a signal generator 2410, note that any alternative examples may exclude such a signal generator 2410 within such as implementation of a DSC, and the one or more processing modules 42 may be configured to provide the reference signal directly to the DSC. For example, the one or more processing modules 42 may include functionality of such a signal generator 2410 therein and the functionality to generate a reference signal having any such desired parameters.

The reference signal is provided to an input of a comparator 2415, which may alternatively be implemented as an operational amplifier. Another input of the comparator 2415 receives the drive signal that is also provided via a single-line to the electrode 1410 to a bodily portion of the subject. The drive signal is generated by a dependent current supply that is powered by a power supply (e.g., Vdd) and that is controlled based on an error signal, Ve, that is generated by the comparator 1415 as it compares the drive signal to the reference signal. Note that the error signal, Ve, at the output of the comparator 2415 is a signal is proportional to the current that is transmitted to or received from the bodily portion of the subject via the electrode 1410. In this diagram, the error signal, Ve, is passed through and analog to digital converter (ADC) 2460 to generate a digital signal that is representative of one or more electrical characteristics of the drive signal including any changes of the drive signal based on one or more electrical characteristics of the electrode 1410, one or more electrical signals coupled into the electrode 1410 from the subject, and/or any other change to the drive signal.

The digital signal is provided to the one or more processing modules 42 and also provided to a DAC 2462 to generate an analog control signal that controls the amount of current that is output from the dependent current supply via the single-line to the electrode 1410. Note that the amount of current, i, that is output from the dependent current supply based on the error signal, Ve, is a function of a programmable scale factor, k, of the dependent current supply such that: $i = k \times Ve$. In certain examples, note also that the one or more processing modules 42 is configured to adjust a programmable gain of the dependent current supply. Note that scaling the programmable gain of the dependent current supply provides for scaling of the error signal, Ve. Control of the current, i, that is output from the dependent current supply may be effectuated by appropriate control of the reference signal as well as the programmable gain of the dependent current supply.

Consider an implementation of the DSC 28-24A servicing a pacemaker lead, such that the electrode 1410 includes a pacemaker lead. Note that the ability to provide current signal of very high precision in terms of any one or more magnitude, pulse width, energy level, current level, voltage level, and/or any other desired parameter in comparison to prior art pacemaker technology allows the pacemaker lead/electrode 1410 to be implemented in a different and improved manner. For example, certain prior art pacemaker leads are implemented to have a very low impedance (e.g., 1s to 10s of Ohms or even lower impedance) along the length of the prior art pacemaker lead and are terminated with a very high impedance termination (e.g., 400 to 1200 Ohms) to limit the amount of current that is delivered via the prior art pacemaker lead to preserve battery power.

For example, many prior art pacemaker systems include circuitry that includes a signal generator and a battery and that generates a signal having a constant voltage, and the higher the impedance of the prior art pacemaker lead, then the lower will be the current drain from the circuitry. For example, the lead tip electrodes of certain prior art pacemaker leads are implemented to have relatively high resistance, such as 400 to 1200 Ohms to minimize the current flow provided from the circuitry via the prior art pacemaker lead and also to preserve control long the life of the battery. In addition, many prior art pacemaker leads that are designed to facilitate sensing as well necessarily require multiple respective electrodes with and the prior art pacemaker lead. For example, consider a prior art pacemaker lead that includes multiple respective electrodes therein, such that a first electrode implemented there in is to facilitate delivery of the electrical impulses of the pace signal, and a second electrode implemented then is to facilitate sensing of one or more electrical signals of the subject.

In an example of operation and implementation, a DSC 28 as described herein (e.g., including DSC 28-24A) that services a pacemaker lead including as few as one single electrode is configured to facilitate both delivery of the electrical impulses of the pace signal and also to facilitate sensing of one or more electrical signals of the subject be at that one single electrode. Prior art pacemaker leads do not cannot provide this functionality and require different respective electrodes within such a prior art pacemaker lead to perform different respective functions. A DSC 28 as described herein (e.g., including DSC 28-24A) that services a pacemaker lead provides a significant improvement over prior art pacemaker leads such that the size of a pacemaker lead that is serviced by a DSC 28 as described herein may be implemented to have much smaller size and be less intrusive when implanted into the subject. For example, given that both delivery of the electrical impulses of a pace signal and also sensing of one or more electrical signals of the subject may be made via one single electrode, the overall size of a pacemaker lead may be reduced significantly when implemented as described herein in comparison to prior art pacemaker technology.

The precision and control provided by a DSC 28 as described herein (e.g., DSC 28-24A of this diagram) obviates the need for having a very high impedance termination on a prior art pacemaker lead. In an example of operation and implementation, a DSC 28 as described here and the service is a pacemaker lead is configured to deliver the current level of any desired value thereby preserving the battery without requiring a very high up impedance termination as is often included on a prior art pacemaker lead. A DSC 28 as described that is configured to service a pacemaker lead is operative to control the amount of current delivered via the pacemaker lead within the respective electrical impulses with a high degree of precision and accuracy thereby prolonging and extending the life of an energy source such as a battery implemented within such a pacemaker application.

In addition, note that such a pacemaker lead that is serviced by a DSC 28 as described herein (e.g., including DSC 28-24A of this diagram) is operative to perform both delivery of the pace signal to a desired portion of the heart of the subject and also to detect cardiac electrical activity of the subject. As such, and implementation including one or more processing models 42 a DSC 28 that services a pacemaker lead may be implemented to operate in a closed loop form such that detection of cardiac electrical activity of the subject is made and that information employed by the one or more processing modules 42 to adjust operation of the pace signal delivered via the pacemaker lead from the DSC 28. This may be viewed as a closed loop implementation in which adaptation of the pace signal provided from the DSC 28 via the pacemaker lead is adapted based on detection of the cardiac electrical activity of the subject that is made simultaneously and concurrently during operation when delivering the pace signal.

Referring to embodiment 2402 of FIG. 24B, this diagram is similar to the prior diagram with at least one difference being that a DSC 28-24B employs an analog control signal that is provided directly based on the error signal, Ve, that is generated from the comparator 2415 to control the amount of current that is output from the dependent current supply via the single-line. In certain examples, the dependent current supply connected to a positive power supply voltage, such as Vdd. Note that this diagram does not include or require the DAC 2462 as shown in the prior diagram. Note that there may be implementations in which the embodiment 2401 of FIG. 24A is preferred to the embodiment 2402 of FIG. 24B. For example, there may be instances in which digital processing, such as filtering, scaling, etc. is desired to be performed on a digital representation of the error signal, Ve, that is generated by the ADC 2460. In such an instance, that digital representation of the error signal, Ve, may undergo such additional processing within DAC 2462 (or in another component implemented between ADC 2460 and DAC 2462) before outputting the analog control signal that controls the amount of current that is output from the dependent current supply via the single-line to the electrode 1410.

In addition, with respect to this diagram and others described herein that include an electrode 1410 that is in proximity to or in contact with a bodily portion of the subject, note that an additional electrode 1410 may be implemented to provide a return electrical signal path to the ground of a DSC 28 (e.g., such as to the ground connection of a signal generator 2410 within DSC 28-24A). In even other implementations, the body of the subject serves as the return path instead of using a dedicated electrode 1410. This alternative variation of including an additional electrode 1410 as a return path is also shown on the subsequent diagram and may be included in any other implementation that includes an electrode implemented that is in proximity to or in contact with a bodily portion of the subject for any of the many variety of purposes as described herein.

In an example of operation and implementation, a pacemaker system includes a drive-sense circuit (DSC) operably coupled to a pacemaker lead. The DSC is operably coupled and configured to receive a reference signal and to generate a pace signal including electrical impulses based on the reference signal. When enabled, the DSC configured to provide the pace signal via the pacemaker lead to an electrically responsive portion of a cardiac conductive system of a subject to facilitate cardiac operation of a cardiovascular system of the subject. Muscles of a heart of the subject produce a mechanical response to the electrical impulses of the pace signal to move blood through the cardiovascular system of the subject. The DSC is also configured to sense, via the pacemaker lead, cardiac electrical activity of the cardiovascular system of the subject that is generated in response to the pace signal and electrically coupled into the pacemaker lead. The DSC is also configured to generate a digital signal that is representative of the cardiac electrical activity of the cardiovascular system of the subject that is sensed via the pacemaker lead.

The pacemaker system also includes one or more processing modules that includes and/or is coupled to memory. The memory that stores operational instructions. When enabled, the one or more processing modules is configured to execute the operational instructions to generate the reference signal and to process the digital signal generated by the DSC to determine the cardiac electrical activity of the cardiovascular system of the subject that is sensed via the pacemaker lead.

In certain examples, the pacemaker lead is implanted in proximity to or into a sinoatrial (SA) node of the cardiovascular system of the subject. In other examples, the pacemaker lead is implanted in proximity to or into a ventricle of the cardiovascular system of the subject. Also, note that the pacemaker lead is implemented with one single conductor. Note that both stimulation (e.g., providing of the impulses of the pace signal) and sensing are performed by the DSC vis the same one single conductor.

In certain other examples, when enabled, the one or more processing modules is further configured to execute the operational instructions to adjust one or more electrical characteristics of the reference signal to facilitate generation of the pace signal by the DSC to facilitate capture by the cardiac conductive system of the subject in response to the pace signal. Note that adjustment of the one or more electrical characteristics of the reference signal causes adjustment of at least one electrical characteristic of the pace signal including at least one of a magnitude of the electrical impulses of the pace signal, a pulse width of the electrical impulses of the pace signal, an amount of current level delivered via the electrical impulses of the pace signal, and/or a frequency or rate of the electrical impulses of the pace signal.

When enabled, the one or more processing modules is further configured to execute the operational instructions to process the digital signal generated by the DSC to determine the cardiac electrical activity of the cardiovascular system of the subject that is sensed via the pacemaker lead including to determine whether there is capture by the cardiac conductive system of the subject in response to the pace signal. Based on a determination that there is no capture by the cardiac conductive system of the subject, the one or more processing modules is further configured to execute the operational instructions to adjust one or more electrical characteristics of the reference signal to facilitate generation of the pace signal by the DSC to facilitate capture by the cardiac conductive system of the subject in response to the pace signal. Note that adjustment of the one or more electrical characteristics of the reference signal causes adjustment of at least one electrical characteristic of the pace signal including at least one of a magnitude of the electrical impulses of the pace signal, a pulse width of the electrical impulses of the pace signal, an amount of current level delivered via the electrical impulses of the pace signal, and/or a frequency or rate of the electrical impulses of the pace signal.

Note that the DSCs may be implemented in any of a variety of ways including as described herein in various examples, embodiments, etc. In certain examples, the DSC includes a comparator configured to produce an error signal based on comparison of the reference signal to the pace signal. The reference signal is received at a first input of the comparator, and the pace signal is received at a second input of the comparator. The DSC also includes a dependent current supply configured to generate the pace signal based on the error signal and to provide the pace signal via a single line that couples to the pacemaker lead and the second input of the comparator. The DSC also includes an analog to digital converter (ADC) configured to process the error signal to generate the digital signal that is representative of the cardiac electrical activity of the cardiovascular system of the subject that is sensed via the pacemaker lead. When enabled, the one or more processing modules is further configured to execute the operational instructions to adjust a programmable gain of the dependent current supply, wherein scaling the programmable gain of the dependent current supply provides for scaling of the error signal.

In certain other examples, the DSC includes a power source circuit operably coupled via a single line to the pacemaker lead. When enabled, the power source circuit is configured to provide an analog signal via the single line coupling to the pacemaker lead, and wherein the analog signal includes at least one of a DC (direct current) component or an oscillating component. The DSC also includes a power source change detection circuit operably coupled to the power source circuit. When enabled, the power source change detection circuit is configured to detect an effect on the analog signal that is based on at least one of an electrical characteristic of the pacemaker lead or the cardiac electrical activity of the cardiovascular system of the subject that is sensed via the pacemaker lead and to generate the digital signal that is representative of the cardiac electrical activity of the cardiovascular system of the subject that is sensed via the pacemaker lead.

In some specific examples, the power source circuit is implemented to include a power source to source at least one of a voltage or a current via the single line to the pacemaker lead. The power source change detection circuit is implemented to include a power source reference circuit configured to provide at least one of a voltage reference or a current reference. The power source change detection circuit is also implemented to include a comparator configured to compare the at least one of the voltage and the current provided via the single line to the pacemaker lead to the at least one of the voltage reference and the current reference to produce the analog signal.

FIGS. 25A and 25B are schematic block diagrams of examples or embodiments 2501 through 2506 of extra pathways within the heart of a subject that can cause tachycardias and one or more DSCs configured simultaneously to drive and sense drive signals to electrodes, respectively, capability to provide capability to reduce or eliminate tachycardias within the subject in accordance with the present invention.

With respect to the various electoral impulses that propagates through a daring apart the cycle, sometimes there are problems with the electrical pathways of the cardiac conduction system or the components of the heart that generate the electrical impulses. In some instances, when there are problems with the electrical pathways of the cardiac conduction system, the result may be an abnormally fast heartbeat, which is referred to as tachycardias, or a slow heartbeat, which is referred to as bradycardias. With respect to bradycardias, the body's natural or normal pacemaker, the sinoatrial (SA) node, does not operate properly or with regularity. This may be referred to as sinus node dysfunction thereby causing a heartbeat that is too slow. A slow heartbeat and bradycardias may be treated by an appropriately implemented pacemaker, such as using a DSC serviced pacemaker lead as described herein.

With respect to tachycardias, or a fast heartbeat, this often occurs when there is an extra electrical path in addition to the normal path between the atrioventricular (AV) node and the His bundle. For example, the electrical impulse that is received in and delayed in the AV node and is being spread via the His bundle is also coupled via an extra or accessory electric pathway back to the AV node. In a specific example, as the electrical impulse is transmitted from the AV node and is being spread via the His bundle and subsequently to the right and left bundle branches, a portion of that electrical impulse also makes its way via the extra or accessory electric pathway back to the AV node. Such an extra or accessory electric pathway back to the AV node is sometimes referred to as Wolf-Parkison-White (WPW) syndrome. When such an extra or accessory electric pathway is included within the AV node, the coupling of the electrical impulse back into the AV node is sometimes referred to as AV node reentry or dual AV node pathways. Generally speaking, when there are extra or accessory electric pathways within the cardiac conduction system, as an electrical impulse is coupled via a normal path within the cardiac conduction system in accordance with facilitating normal heart operation, the impulse may unfortunately also be coupled via an extra or accessory electrical pathway. This will result in improper operation of the heart. In instance where electoral impulse reenters the AV node, this can subsequently result in an abnormally fast heartbeat. Note that such extra or accessory electric pathways may unfortunately occur in various parts of the heart for various reasons, including congenital deficiencies in the formation of the heart during gestation of the subject, damage of the heart for any of a variety of reasons including physical or electrical trauma, etc. Considering a specific example in which there is an extra or accessory electric pathway between the atria and the ventricles, this can unfortunately result in an electrical impulse making a continuous loop within the heart thereby producing an undesired fast heartbeat (tachycardias).

Referring to example 2501 of FIG. 25A on the left-hand side of the diagram, this diagram shows AV node reentry or dual AV node pathways such that there is an extra pathway between the atria and ventricles, which is separate from or with in the AV node, and the electrical impulses from the SA node that are supposed to be received in and delayed in the AV node and is being spread via the His bundle is also coupled via an extra or accessory electrical pathway back to the AV node are unfortunately caught in a continuous loop and reenter the AV node thereby producing an abnormal electrical impulse that is received by the AV node and can result in an abnormally fast heartbeat. Each time the impulse completes a circuit, including via this extra or accessory electric pathway back to the AV node, the heart beats. In extreme situations this can result in a very rapid heartbeat that is very dangerous for the subject.

In another specific example, instead of the heart including an extra or accessory electric pathway within the cardiac conduction system, there may be an abnormal "focus" within the heart (e.g., a group of conductive cells) that unfortunately acts as a second SA node or natural pacemaker in addition to the proper and primary SA node. When this abnormal "focus" within the heart unfortunately generates electrical impulses itself, in addition to the electrical impulses generated by the proper and primary SA node, this also may generate an abnormally fast heartbeat. Such an abnormal "focus" may be located in different portions of the heart, such as in either the upper (atria) or lower chambers (ventricles).

Referring to example 2502 of FIG. 25A on the right-hand side of the diagram, this shows dual pathways within the AV node. For example, the typical electrical pathway between the atrium to the His bundle via the AV node, there are unfortunately dual electric pathways. In many instances, one of them is faster than the other (e.g., one may have better electrical conductivity than the other and couples electrical impulses more quickly than the other).

Referring to example 2503 of FIG. 25B, this diagram is shaped similar to the example 2502 of FIG. 25A and also shows the electrical impulses as a function of time, consider t1 being a first time, t2 being a second time after t1, and so on through t4. As can be seen, the electrical impulses provided from the atrium at a first time t1 and propagates via one of the duel pathways within the AV node during a second time t2. Unfortunately, during a third time t3, the electrical impulse is not only coupled towards the His bundle but also via the dual electric pathway within the AV node via this continuous loop within the AV node. Then, during the fourth time t4 electrical impulse is coupled from the His bundle towards the left and right bundle branch is and also back towards the atrium.

Referring to example 2503 of FIG. 25B, as can be seen, there is increased electrical signal level due to AV node reentry via the dual AV node pathways within our hearts that unfortunately includes an extra or accessory electric pathway back to the AV node. As can be seen, during times t3 and t4, there is not only the normal electrical impulses that are propagated through the cardiac conduction system, but also the additional electrical impulses that are unfortunately coupled back to the AV node.

A DSC serviced pacemaker lead or sensing lead is operative to detect the increased electric signal level due to such an extra or accessory electric pathway (e.g., back to the AV node in this particular instance). In addition, such a DSC serviced pacemaker lead or sensing lead is operative to detect the particular timing of such increased signal levels that may result from an extra or accessory electric pathway.

Referring to embodiment 2503 of FIG. 25B, this shows one possible implementation by which one or more processing modules 42 is in communication with the DSC 28 that services electrode 1410. In this implementation, the electrode 1410 is implemented not only to facilitate sensing of cardiac activity by the DSC 28 but also to provide a current sink signal that is provided from the DSC 28 to reduce or eliminate the extra electrical impulse that is unfortunately traveling via the extra or accessory electric pathway. This implementation includes a single electrode 1410 is operative to perform both sensing of the additional electric activity and also to provide a current sink signal to reduce or eliminate the extra electrical impulse to provide treatment of the tachycardia. By providing a current sink signal, such as a signal the one opposite to the extra electrical impulse that is traveling via the extra or accessory electric pathway, tachycardia within the subject may be reduced or eliminated.

Referring to embodiment 2503 of FIG. 25B, this shows another possible implementation by which one or more processing modules 42 is in communication with a first DSC 28 that services a first electrode 1410 and also the second DSC 28 that services the second electrode 1410. The first electrode 1410 is implemented to facilitate sensing of cardiac activity by the first DSC 28. The second electrode 1410 is implemented to facilitate delivery of the current sink signal by the second DSC 28 to reduce or eliminate the extra electrical impulse to provide treatment of the tachycardia. In a similar location, two different electrodes 1410 are implemented to perform two different purposes (e.g., the first one to facilitate sensing and the second one to facilitate delivery of the current sink signal).

Because a DSC 28 as described herein has the ability to perform sensing with such high level of sensitivity, resolution, granularity, etc., an appropriately provided current sink signal to counter the electrical impulse traveling via the extra or accessory electric pathway may be reduced or eliminated thereby reducing or eliminating the abnormally fast heart beat associated with tachycardia.

FIGS. 26A and 26B are schematic block diagrams of other embodiments 2601 and 2602 of DSCs configured simultaneously to drive and sense drive signals to electrodes, respectively, and that include capability to provide current sink signals in accordance with the present invention.

Referring to embodiment 2601 of FIG. 26A, this diagram is similar to the embodiment 2401 of FIG. 24A with at least one difference being that the dependent current supply is instead implemented to provide a current sink signal. In an example of operation and implementation, consider DSC 28-26A to be the second DSC 28 of the embodiment 2503 of FIG. 25B that is implemented to facilitate delivery of a current sink signal to counter the electrical impulse traveling via the extra or accessory electric pathway (e.g., the dependent current supply connected to a negative power supply voltage, such as −Vdd). Note that different respective DSCs may be implemented different purposes within particular application.

Referring to embodiment 2602 of FIG. 26B, this diagram is similar to the prior diagram with at least one difference being that a DSC 28-26B employs an analog control signal that is provided directly based on the error signal, Ve, that is generated from the comparator 2415 to control the amount of current that is output from the dependent current supply via the single-line. Note that this diagram does not include or require the DAC 2462 as shown in the prior diagram.

FIGS. 27A and 27B are schematic block diagrams of other embodiments 2701 and 2702 of DSCs configured simultaneously to drive and sense drive signals to electrodes, respectively, and that include capability to provide current source or current sink signals in accordance with the present invention.

Referring to embodiment 2701 of FIG. 27A, this diagram has similarities to the embodiment 2401 of FIG. 24A and also the embodiment of 2601 of FIG. 26A. This diagram includes two dependent current sources that are controlled by the analog control signals that are generated by two DACs 2462. The two DACs 2462 receive a digital signal provided from ADC 2460 that is configured to generate a digital signal representation of the error signal, Ve, that is generated from the comparator 2415. The DSC 28-27A of this diagram includes capability to provide a current signal that is operative as a current sink signal (e.g., via the dependent current supply connected to a negative power supply voltages, such as −Vdd) or the current source signal (e.g., via the dependent current supply connected to a positive power supply voltage, such as Vdd). Generally speaking, with respect to a dependent current supply, the amount of current, i, that is output from such a dependent current supply based on the error signal, Ve, is a function of a programmable scale factor, k, of the dependent current supply such that: i=k×Ve.

In this diagram, consider the current sink signal to be i1=k1*Ve that is provided from the dependent current source that is implemented to provide a current sink signal, and consider the current source signal to be i2=k2*Ve that is provided from the dependent current source that is implemented to provide a current source signal (e.g., where k1 and k2 are the programmable scale factors of the two respective dependent current sources, which may be the same programmable scale factors, or different), then the total current i3 that is delivered by the DSC 28-27A of this diagram is the combination of i1 and i2 (e.g., i3=i1=i2).

Referring to embodiment 2702 of FIG. 27B, this diagram is similar to the prior diagram with at least one difference being that a DSC 28-27B employs an analog control signal that is provided directly based on the error signal, Ve, that is generated from the comparator 2415 to control the amounts of the currents that are output from the dependent current supplies and combined to be provided via the single-line coupling to the electrode 1410. Note that this diagram does not include or require the two DACs 2462 as shown in the prior diagram. In certain alternative embodiments, as switches implemented such that the analog control signal is provided to only one of the two dependent current supplies as needed to adapt the drive signal, whether to provide a current sink signal or a current source signal to ensure that the drive signal properly tracks, follows, matches, etc. the reference signal provided to the one of the inputs of the comparator 2415.

In addition, in certain implementations, the DSC 28 services an electrode 1410 that is operative to perform more than one operation including sensing of cardiac electrical activity as well as delivery of a current sink signal in accordance with treatment of tachycardias. In certain other implementations, the DSC 28 services an electrode 1410 that is operative to perform multiple operations including sensing of cardiac electrical activity, delivery of a current sink signal in accordance with treatment of tachycardias, and also delivery of the pacing signal. Note that multiple respective functions and operations baby effectuated via a DSC 28 that services a single electrode 1410 based on the total flexibility by which a reference signal may be generated and used within a DSC as described herein. For example, an appropriately designed reference signal may be implemented to perform more than one operation via the single electrode 1410 that is serviced by a single DSC 28. Given that any of the parameters of the drive signal may be adjusted in any desired manner (e.g., voltage level, current level, pulse width, frequency, shape, etc.), a reference signal that is designed to serve multiple purposes may be used by a DSC 28 to generate a drive signal to perform these different operations (e.g., sensing, current sink signal, pacing signal delivery, etc.).

FIGS. 28A, 28B, and 28C are schematic block diagrams of other embodiments 2801, 2802, and 2803 of DSCs configured simultaneously to drive and sense drive signals to electrodes, respectively, and that include capability to provide differential sensing and/or stimulation across one or more bodily portions of a subject in accordance with the present invention.

Referring to embodiment 2801 of FIG. 28A, one or more processing modules 42 are in communication with two DSCs 28 (e.g., a first DSC 28 and a second DSC 28). As described also with respect other embodiments, examples, diagrams, etc. herein, the one or more processing modules 42 are configured to provide various signals to the DSCs 28 including one or more of reference signals, power input, communication signals, interfacing signals, control signaling, etc. and also to receive for serious signals from the DSCs 28 including one or more of information from the DSCs 28 corresponding to one or more electrical characteristics of the signals provided from the DSCs 28 via the electrodes 1410, one or more electrical characteristics of the electrodes 1410 themselves, one or more electrical signals coupled into the electrodes 1410, and/or change of any one or more of these electrical characteristics, etc.

Note that the DSCs may be implemented in any desired configuration including any of the variants described herein such as operating by providing a voltage signal, current signal, a current sink or source signal, etc. The two DSCs 28 operate cooperatively perform differential sensing and/or stimulation across a particular bodily portion. Each of the DSCs 28 services a respective electrode 1410. Each of the respective DSCs 28 operates based on a different respective reference signal (e.g., first reference signal and second reference signal). In an example of operation and implementation, a first reference signal that is employed by one of the DSCs 28 is 180° out of phase or an inverted version of the first reference signal that is employed by the other one of the DSCs 28. The two electrodes 1410 are located within a desired proximity to one another so as to facilitate coupling of signals between the ends of the electrodes 1410 as they are being serviced by the DSCs 28. As electrical signals are coupled between the ends of the electrodes 1410, the two DSCs 28 operate cooperatively to provide signals via the two respective electrodes 1410, and electric signals are coupled between the ends of the electrodes 1410 via the pathway between the two bodily portions (e.g., first location on bodily portion and second location on bodily portion).

For example, to effectuate differential sensing and/or stimulation between the first location of other portion of the second but with portion, electrical signaling is coupled between the two ends of the electrodes 1410 via a pathway through the subject between the ends of those two electrodes 1410. In a specific example, consider an implementation which a particular portion or section of the heart of the subject is to be stimulated, then the ends of the electrodes 1410 are placed (e.g., implanted) across that particular portion or section of a heart of the subject so that electrical signaling coupled between the ends of the electrodes 1410 travels across that particular portion or section of the heart. Again, note that the DSCs 28 are operative to perform both differential sensing and/or stimulation across a particular bodily portion such that sensing of one or more electrical characteristics of that particular bodily portion, between the first and second location, may be made simultaneously and concurrently when delivering differential stimulation by driving an electrical signal to provide electrical stimulation to that bodily portion. Note that there may be applications in which only differential sensing or only differential stimulation is desired, but the DSCs 28 are also operative to perform both differential sensing and differential stimulation in alternative applications.

Referring to embodiment 2802 of FIG. 28B, this diagram has certain similarities to the previous diagram and provides additional detail regarding one particular manner by which the DSCs may be implemented. In this diagram, DSCs 28-28B are implemented similarly to the DSC 28-24A or DSC 28-24B of FIGS. 24A and 24B, respectively. Note that the DSCs 28-28B may be implemented without the DAC 2462 in certain implementations such that the analog control signal is provided directly based on the error signal, Ve, that is generated from the comparator 2415 to control the amounts of the current that is output from the dependent current supply and provided via the single-line coupling to the electrode 1410.

In an example of operation and implementation, a first reference signal that is employed by one of the DSCs 28-28B is 180° out of phase or an inverted version of the first reference signal that is employed by the other one of the DSCs 28-28B. As with respect to the previous diagram, the two electrodes 1410 are located within a desired proximity to one another so as to facilitate coupling of signals between the ends of the electrodes 1410 as they are being serviced by the DSCs 28-28B. As electrical signals are coupled between the ends of the electrodes 1410, the two DSCs 28-28B operate cooperatively to provide signals via the two respective electrodes 1410, and electric signals are coupled between the ends of the electrodes 1410 via the pathway between the two bodily portions (e.g., first location on bodily portion and second location on bodily portion). Note that such cooperative operation between the respective electrodes 1410 and the signals driven via them by their respective DSCs 28-28B are operative to facilitate differential sensing and/or differential stimulation as may be desired in various applications.

Referring to embodiment 2803 of FIG. 28C, this diagram is similar to the prior previous diagram with certain differences being that the communication between the one or more processing modules 42 and DSCs 28-28C are made via respective communication pathways that include any number of communication channels, pathways, etc. (e.g., generally n, where n is a positive integer greater than or equal to 1) such that the digital information corresponding to one or more electrical characteristics of the signals provided from the DSCs 28 via the electrodes 1410, one or more electrical characteristics of the electrodes 1410 themselves, one or more electrical signals coupled into the electrodes 1410, and/or change of any one or more of these electrical characteristics, etc. from the ADCs 2460 are provided via these respective communication pathways. Also, the reference signals provided to comparators 2415 of the DSCs 28-28C are provided from the one or more processing modules 42 via these respective communication pathways as well. For example, rather than the information corresponding to one or more electrical characteristics of the signals provided from the DSCs 28 via the electrodes 1410, one or more electrical characteristics of the electrodes 1410 themselves, one or more electrical signals coupled into the electrodes 1410, and/or change of any one or more of these electrical characteristics, etc. being provided via a direct connection from the ADCs 2460 of the DSCs 28-28C, they are provided via these respective communication pathways. Similar to the previous diagram and others that are implemented to facilitate differential sensing and/or stimulation a first reference signal that is employed by one of the DSCs 28-28C is 180° out of phase or an inverted version of the first reference signal that is employed by the other one of the DSCs 28-28C. Also, as with respect to previous diagrams, the two electrodes 1410 are located within a desired proximity to one another so as to facilitate coupling of signals between the ends of the electrodes 1410 as they are being serviced by the DSCs 28-28C.

FIGS. 29A and 29B are schematic block diagrams of embodiments 2901 and 2902 of sheaths that are serviced by DSCs that are operative simultaneously to drive and sense drive signals to electrodes, respectively, and that also includes capability to provide single-ended or differential sensing and/or stimulation across one or more bodily portions of a subject in accordance with the present invention.

Referring to embodiment 2901 of FIG. 29A, a sheath 2911 includes multiple respective sensing and/or stimulation conductive points. Note that the conductive points may be implemented using any desired conductive material (e.g., any type of metal such as copper, aluminum, platinum, gold, silver, iron, steel, brass, graphite, graphite, and/or any other material having electrically conductive properties). Each of the respective sensing and/or stimulation conductive points of the sheath 2911 is coupled via a respective electrode 1410 to corresponding DSC 28. As with respect to other diagrams herein, the DSCs 28 are in communication with one or more processing modules 42 via one or more communication channels, pathways, etc. (e.g., generally n, where n is a positive integer greater than or equal to 1). Examples of one or more signals that may be provided between the DSCs 28 and the one or more processing modules 42 to the DSC may include any one or more of a reference signal such as provided from the one or more processing modules 42 to one or more of the DSCs 28 (e.g., referred to as Vref in certain diagrams), power input, communication signaling, interfacing, control signaling, digital information provided from the DSC 28 to the one or more processing modules 42, digital information provided from the one or more processing modules 42 to the DSC 28, etc.

The sheath 2911 includes the integrated sensing and/or stimulation conductive points that are operative to facilitate bodily sensing and/or stimulation of the subject based on a particular bodily portion of the subject with which the sheath 2911 is in contact or wrapped around. Note that the sheath 2911 may be implemented in a variety of ways. For example, the sheath 2911 may be constructed of a rigid material having a particular shape, such as flat or curved or any desired shape, such that a rigid sheath is placed in contact with a bodily portion of the subject to facilitate sensing and/or stimulation via the sensing and/or stimulation conductive points of the rigid sheath. In another example, the sheath 2911 may be constructed of a flexible material and/or a wrap-able material that may be wrapped around a bodily portion of the subject, such as around a portion of the abdomen, a leg, an arm, forget, etc. of the subject. In certain implementations, such a flexible and/or wrap-able sheath may include one or more means to fasten the sheath 2911 and hold it in place at a desired location with respect to the subject. Examples of such fastening means may include Velcro, straps, buttons, etc. and/or any desired means to keep the sheath 2911 in a desired location with respect to a bodily portion of the subject.

Note also that the sheath 2911 may include any desired number of sensing and/or stimulation conductive points arranged in any desired pattern. One example of a pattern includes a rectangular shaped matrix of sensing and/or stimulation conductive points as shown in the diagram; however, any other desired pattern may alternatively be used. Other patterns may include the sensing and/or simulation conductive points arranged in a square shaped pattern, triangular pattern, circular pattern, etc. and/or any other desired pattern. Also, note that sheath 2911 may be of any desired size and shape itself. The sheath 2911 shown in the diagram is a substantially rectangular shaped sheath 2911 with rounded corners; however, any desired alternative shape may alternatively be used for the sheath 2911.

In an example of operation and implementation, the DSCs 28 are coupled respectively via electrodes 1410 to different respective sensing and/or stimulation conductive points of the sheath 2911. For example, a first DSC 28 is coupled via a first electrode 1410 to a first sensing and/or stimulation point of the sheath 2911. A second DSC is coupled via a second electrode 1410 to a second sensing and/or stimulation point of the sheath 2911, and so on such that the DSCs 28 are coupled respectively via electrodes 1410 to the different respective sensing and/or stimulation conductive points of the sheath 2911 on a one-to-one basis such that each respective DSC 20 services a respective sensing and/or stimulation point of the sheath 2911.

In an example of operation and implementation, the electrical signals provided from the DSCs 28 that are coupled via the respective electrodes 1410 to the sensing and/or stimulation conductive points of the sheath 2911 are coupled from the sensing and/or stimulation conductive points of the sheath 2911 into a bodily portion of the subject that is in proximity to or in contact with the sheath 2911. Considering an application of stimulation, such as in rehabilitation of injured muscle of the subject (e.g., such as a torn hamstring of an athlete), electrical stimulation is provided from the stimulation conductive points of the sheath 2911 to all or a desired portion of the injured muscle of the subject to assist in the rehabilitation and recovery of the injured muscle of the subject. Note that the electrical signaling provided via the stimulation conductive points of the sheath 2911 may be controlled in any desired manner based on the flexibility and control of the signaling that may be provided from the respective DSCs 28.

In one example, electrical stimulation is provided via electrical signals from the stimulation conductive points of the sheath 2911 in a uniform manner across all of the stimulation conductive points of the sheath 2911 such that all of the electrical signals are of the same type (e.g., having the same electrical characteristics including one or more of synchronized in time, in phase with one another, same magnitude, same frequency if not DC signals, etc.). In another example, electrical stimulation is provided in a time varying manner via electrical signals that are non-uniform across the stimulation conductive points of the sheath 2911 (e.g., having different electrical characteristics including one or more of being non-synchronous signals, out of phase with one another, of different magnitudes, different frequencies if not DC signals, etc.).

In yet another example, electrical stimulation is provided in a time varying manner such that waves of electrical stimulation are provided across the bodily portion of the subject that is in proximity with or in contact with the sheath 2911. For example, consider electrical stimulation starting on the leftmost column of the stimulation conductive points of the sheath 2911 and propagating column by column to the right on a periodic basis, such that electrical stimulation is first provided you the leftmost column, then the column to the right of that one, then to the next column to the right of that one, and so on until the rightmost column of the sheath 2911 provides electrical stimulation, and then the process begins again with the leftmost, of the stimulation conductive points of the sheath 2911. Alternatively, such stimulation could begin on the right of the sheath 2911 and propagate towards the left of the sheath 2911. Similarly, such electrical stimulation may be provided via respective rows of the stimulation conductive points of the sheath 2911 as well, such as starting from top towards bottom orb, or vice versa. In yet another example, electrical stimulation is provided any electrical stimulation pattern manner starting by using the outermost stimulation conductive points of the sheath 2911, then by using the stimulation conductive points of the sheath 2911 that are located within a first perimeter formed by the outermost stimulation conductive points of the sheath 2911, and then by using the stimulation conductive points of the sheath that are located within a second perimeter of stimulation conductive points of the sheath 2911, and so on such that, as a function of time, the electrical stimulation provided by the sheath 2911 becomes more and more concentrated toward the center stimulation conductive points of the sheath 2911. Generally speaking, any desired manner of electrical stimulation may be at performed using the stimulation conductive points of the sheath 2911 given that the respective signals provided from the DSCs 28 via the electrodes 1410 to the stimulation conductive points of the sheath 2911 may be generated in any desired manner. Given the total flexibility by which a reference signal may be generated and used within the DSC 28 as described herein (e.g., such as using signal generator or within one or more processing modules 42), any of the parameters of the stimulation sensing and/or stimulation signals including any one or more of voltage level, current level, pulse width, frequency, shape, etc. may be adjusted to any desired value with extremely fine resolution and accuracy.

Referring to embodiment 2902 of FIG. 29B, the sheath 2912 includes differential pairs of sensing and/or simulation conductive points that are serviced via DSCs 28 that couples to them via electrodes 1410. As with respect to other diagrams herein, the DSCs 28 are in communication with one or more processing modules 42 via one or more communication channels, pathways, etc. (e.g., generally n, where n is a positive integer greater than or equal to 1). In this diagram, respective pairs of sensing and/or stimulation conductive points operate cooperatively to facilitate differential sensing and/or stimulation via the sheath 2912 that is operative to be in proximity to or in contact with a bodily portion of the subject.

For example, a first DSC 28 services, via a first electrode 1410, a first point of a first differential pair of sensing and/or simulation conductive points of the sheath 2912, and a second DSC 28 services, via a second electrode 1410, a second point of the first differential pair of sensing and destination conductive points of the sheath 2912. This first and second conductive points of the first differential pair of sensing and/or stimulation conductive points operate cooperatively based on the electrical signaling provided to them via the electrodes 1410 and the first DSC 28 and the second DSC 28. Similar to the differential sensing and/or stimulation is described elsewhere herein, the use of the differential pairs of sensing and/or simulation conductive points of the sheath 2912 facilitate very localized and controlled sensing and/or simulation across a particular desired bodily portion of the subject between the two sensing and/or stimulation conductive points of the differential pair of sensing and/or stimulation conductive points. Similarly, a third DSC 28 services, via a third electrode 1410, a first point of a second differential pair of sensing and/or simulation conductive points of the sheath 2912, and a fourth DSC 28 services, the a fourth electrode 1410, a second point of the second differential pair of sensing and/or stimulation conductive points of the sheath 2912. Additionally, other DSCs 28 respectively service, via other electrodes 1410, the other respective conductive points within the other differential pairs of sensing and/or stimulation conductive points of the sheath 2912.

Similar to the sheath 2912 of the previous diagram, the sheath 2912 includes the integrated sensing and/or stimulation conductive points in different pairs that operate cooperatively and that are operative to facilitate bodily sensing and/or stimulation of the subject based on a particular bodily portion of the subject with which the sheath 2912 is in contact or wrapped around. Also, note that the sheath 2912 may be implemented in a variety of ways similar to the sheath 2911 (e.g., constructed of a rigid material having a particular shape, such as flat or curved or any desired shape, such that a rigid sheath is placed in contact with a bodily portion of the subject to facilitate sensing and/or stimulation via the sensing and/or stimulation conductive points of the rigid sheath or constructed of a flexible material and/or a wrap-able material that may be wrapped around a bodily portion of the subject, may include one or more means to fasten the sheath 2912 and hold it in place at a desired location with respect to the subject).

Note also that the sheath 2912 may include any desired number of differential pairs of sensing and/or stimulation conductive points arranged in any desired pattern or arrangement (e.g., triangular, square, circular, oval, etc.). One example of a pattern or arrangement includes a rectangular shaped matrix of sensing and/or stimulation conductive points as shown in the diagram such that the differential pairs of sensing and/or stimulation conductive points are aligned horizontally. Generally speaking, any other desired pattern or arrangement may alternatively be used. Also, similar with respect to the sheath 2911 of the previous diagram, note that sheath 2912 may be of any desired size and shape itself. The sheath 2912 shown in the diagram is a substantially rectangular shaped sheath 2912 with rounded corners; however, any desired alternative shape may alternatively be used for the sheath 2912.

In an example of operation and implementation, the DSCs 28 are coupled respectively via electrodes 1410 to different respective sensing and/or stimulation conductive points of the different respective differential pairs of sensing and/or stimulation conductive points of the sheath 2912. For example, a first DSC 28 is coupled via a first electrode 1410 to a first sensing and/or stimulation point of a first differential pair of sensing and/or stimulation conductive points of the sheath 2912. A second DSC is coupled via a second electrode 1410 to a second sensing and/or stimulation point the first differential pair of sensing and/or stimulation conductive points of the sheath 2912, and so on such that the DSCs 28 are coupled respectively via electrodes 1410 to the different respective sensing and/or stimulation conductive points of each of the differential pairs of sensing and/or stimulation conductive points of the sheath 2912 on a one-to-one basis such that each respective DSC 20 services a respective sensing and/or stimulation point of the sheath 2912.

In an example of operation and implementation, a first reference signal that is employed by one of the DSCs 28 that services a first point of a first differential pair of sensing and/or stimulation conductive points is 180° out of phase or an inverted version of the first reference signal that is employed by the other one of the DSCs 28 that services a second point of the first differential pair of sensing and/or stimulation conductive points. The two conductive points of the point of a first differential pair of sensing and/or stimulation conductive points are spaced apart by a desired proximity to one another so as to facilitate coupling of signals between them based on the signaling that is provided to them by the DSCs 28 that service them 28. As electrical signals are coupled between the two conductive points of the point of a first differential pair of sensing and/or stimulation conductive points, the two DSCs 28 operate cooperatively to provide signals via the two respective electrodes 1410, and electric signals are coupled between the two conductive points of the point of a first differential pair of sensing and/or stimulation conductive points via the pathway between the two bodily portions (e.g., first location on bodily portion and second location on bodily portion).

Similar to the sheath 2911, note also that the sheath 2912 may include any desired number of differential pairs of sensing and/or stimulation conductive points, and the sheath 2912 may have any desired size and shape. Note also that the respective spacing between the sensing and/or stimulation conductive points of the differential pairs of sensing and/or stimulation conductive points may be uniform throughout the sheet 2912, or they may be different. For example, note that a first differential pair of sensing and/or stimulation conductive points of the sheath 2912 may be separated by a first distance, and a second differential pair of sensing and/or stimulation conductive points of the sheath 2912 may be separated by a second distance that is different than the first distance. Generally speaking, the different respective differential pairs of sensing and/or submission conductive points of the sheath 2912 may be implemented according to any desired pattern or arrangement, spacing, etc. in certain examples, the spacing between the conductive points of the differential pairs of sensing and/or stimulation conductive points is selected based on the signaling to be provided to them so as to facilitate coupling of electrical signals between the two conductive points of a differential pair of sensing and/or stimulation conductive points. For example, a larger distance between the two conductive points of a differential pair of sensing and/or stimulation conductive points may be made when higher levels of signaling (e.g., higher magnitude of voltage and/or current) as opposed to lower levels of signaling (e.g., lower magnitude of voltage and/or current) that are insufficient to facilitate coupling between the two conductive points of the differential pair of sensing and/or stimulation conductive points. In addition, note that the electrical stimulation provided via the sheath 2912 may be performed uniformly, nonuniformly, time varying, patterned or wave driven, etc. similarly as described above with respect to the sheath 2911 of the previous diagram.

FIG. 29C is a schematic block diagram of an embodiment 2903 of a sheath showing connectivity of electrodes to the sensing and/or stimulation conductive points of the sheath in accordance with the present invention. This diagram shows a side view of a sheath 2913 that includes sensing and/or stimulation conductive points. The sheath 2913 includes an interface that couples electrodes (e.g., such as electrodes 1410 that are respectively serviced by different DSCs 28 as described with respect to other diagrams herein) to the sensing and/or stimulation conductive points of the sheath 2913. In addition, within the sheath 2913, the sensing and/or stimulation conductive points of the sheath 2913 are implemented and respectively surrounded by electrical insulation between them to impede or stop any coupling of electrical signals between the wires or electrodes that connect couple from the interface to the respective sensing and or submission conductive points of the sheath 2913. The electrical insulating material may be of any desired type. Examples of electrical insulating material may include any one or more of glass, paper, Teflon, rubber-like polymers, plastics, fiberglass, porcelain, and/or any other material having electrically insulating properties. Electrical connection is made within the sheath 2913 via wires, electrodes, or other means from the interface of the sheath 2913 and through the electrical insulation of the sheath 2913 to the different sensing and/or stimulation conductive points of the sheath 2913. Separating the respective sensing and/or stimulation conductive points of the sheath 2913 from one another spatially and also electrically insulating them from one another provides the ability to ensure very localized control of the sensing and/or stimulation to be performed via the respective sensing and/or stimulation conductive points of the sheath 2913.

In addition, with respect to other embodiments, note that other design considerations may be employed to facilitate electrical insulation between the sensing and/or stimulation conductive points of a sheath. For example, they may be spatially separated such that there is little to no electrical coupling between them, if no electrical coupling is desired between them in certain embodiments. In certain embodiments, when operating one or more DSCs to provide AC signaling, the cross coupling between the respective sensing and/or stimulation points would be based on capacitive coupling, especially when using higher frequency AC signaling.

FIG. 29D includes schematic block diagrams of embodiments 2904 and 2905 of sheaths that are operative to facilitate sensing and/or stimulation across one or more bodily portions of a subject in accordance with the present invention. Note that the respective sheaths 2914-1, 2914-2, 2914-3, 2914-4, and 2914-5 may be implemented in and any number of different ways including the sensing and/or stimulation conductive points are individually serviced by respective DSCs such as with respect to FIG. 29A, the sensing and/or stimulation conductive points are implemented in differential pairs such as respective FIG. 29B, etc. Also, note that the respective sheaths 2914-1, 2914-2, 2914-3, 2914-4, and 2914-5 may be constructed of any types of materials including rigid material, flexible material, etc., and they may have any desired shape.

Referring to embodiment 2904, the sheath 2914-1 is shown as being in contact with or wrapped around the bicep of the subject. Sheath 2914-2 is shown as being in contact with the wraparound a quadricep of the subject.

Referring to embodiment 2905, sheath 2914-3 is shown as being in contact with or wrapped around a portion of the head of the subject, such as around for head. Sheath 2914-4 is shown as being in contact with or wrapped around the chest or thorax of a subject. Sheath 29 1405 is shown as being in contact with the wraparound the abdomen of the subject.

In addition, note that in certain implementations that perform differential sensing and/or stimulation, the pairing of two conductive points of a particular differential pair of sensing and/or stimulation conductive points is implemented such that the differential sensing and/or stimulation is made through a particular bodily portion of the subject. For example, when the sheath is in contact with the wraparound a bodily portion of the subject (e.g., around the bicep or quadricep), the two conductive points of a particular differential pair of sensing and/or stimulation conductive points may be located oppositely with respect to that bodily portion of the subject so that the differential signaling travels through that particular bodily portion of the subject (e.g., through the bicep or quadricep).

In other implementations that perform differential sensing and/or stimulation, the pairing of two conductive points of a particular differential pair of sensing and or stimulation conductive points is implemented such that the differential sensing and/or stimulation is made across the surface of skin and/or within the bodily portion just below the surface of the skin between the two conductive points of a differential pair of sensing and/or stimulation conductive points (e.g., based on the electrical signals coupling between the two conductive points of the differential pair of sensing and/or stimulation conductive points and also coupling into that bodily portion of the subject).

In addition, note that two different sheaths located on opposite sides of a bodily portion of the subject may be implemented to operate cooperatively with one another. For example, consider a first sheath located on the front of the chest or thorax of a subject and a second sheath located on the back of the subject that operate cooperatively one another such that electrical signaling is transmitted from the first sheath and received via the seconds sheath.

In an example of operation and implementation, an electrical stimulation system includes sheath (e.g., such as in any of the FIG. 29A, 29B, 29C, or 29D). The sheath includes conductive points that are operative to facilitate electrical stimulation to a bodily portion of a user. In addition, the electrical stimulation system includes drive-sense circuits (DSCs) 28 operably coupled to the conductive points of the sheath via electrodes 1410. Note that the DSCs are configured to generate electrical stimulation signals based on reference signals. The electrical stimulation signals are coupled into the bodily portion of the user via the conductive points of the sheath. When enabled, a first DSC is configured to provide a first electrical stimulation signal via a first electrode to a first conductive point of the sheath. The first electrical stimulation signal is coupled into a first location of the bodily portion of the user that is in proximity to or in contact with the first conductive point of the sheath. Also, the first DSC is configured to sense, via the first conductive point of the sheath and via the first electrode, a first change of the first electrical stimulation signal based on coupling of the first electrical stimulation signal into the first location of the bodily portion of the user. The first DSC is also configured to generate a first digital signal that is representative of the first change of the first electrical stimulation signal.

Similarly, when enabled, a second DSC is configured to provide a second electrical stimulation signal via a second electrode to a second conductive point of the sheath. The second electrical stimulation signal is coupled into a second location of the bodily portion of the user that is in proximity to or in contact with the second conductive point of the sheath. The second DSC is also configured to sense, the second conductive point of the sheath and via the second electrode, a second change of the second electrical stimulation signal based on coupling of the second electrical stimulation signal into the second location of the bodily portion of the user. Also, the second DSC is configured to generate a second digital signal that is representative of the second change of the second electrical stimulation signal.

The electrical stimulation system also includes one or more processing modules that includes and/or is coupled to memory that stores operational instructions. The one or more processing modules is operably coupled to the DSCs. When enabled, the one or more processing modules is configured to execute the operational instructions to generate the plurality of reference signals and to process digital signals generated by the DSCs including the first digital signal generated by the first DSC and the second digital signal generated by the first DSC to determine a response profile of one or more electrical characteristics of the bodily portion of the user. Note that the response profile of one or more electrical characteristics of the bodily portion of the user may correspond to a variety of types. For example, the response profile of one or more electrical characteristics of the bodily portion of the user may correspond to any one or more of an impedance (Z) profile of the bodily portion of the user, a voltage of the bodily portion of the user, a current profile of the bodily portion of the user, cardiac electrical activity of the bodily portion of the user, electrical signal coupling into or from the of the bodily portion of the user, etc.

In certain examples, the sheath is implemented with a rigid material that is shaped to interface with the bodily portion of the user. In other examples, the sheath is implemented with a flexible and wrap-able material that is operative to be placed against the bodily portion of the user. If desired, the sheath also includes one or more fasteners to keep sheath in place against the bodily portion of the user.

In even other examples, the first electrical stimulation signal is 180 degrees out of phase to the second electrical stimulation signal, and the first conductive point of the sheath and the second conductive point of the sheath operate cooperatively to provide differential electrical stimulation between the first location of the bodily portion of the user and the second location of the bodily portion of the user. Also, note that the electrodes may be electrically isolated from each other within the sheath by an electrically insulating material such as described with reference to FIG. 29C. Note also that the bodily portion of the user may be any bodily portion. Some possible bodily portions include a leg, an arm, abdomen, chest or thorax, or head of the user.

Note also that the conductive points of the sheath may be arranged in any desired pattern or arrangement. One specific pattern or arrangement includes a matrix pattern including rows of conductive points and columns of conductive points. In an example of operation and implementation, when enabled, the DSCs is configured to provide the plurality of electrical stimulation signals via the plurality of electrodes to the plurality of conductive points, including the first electrical stimulation signal via the first electrode to the first conductive point of the sheath and the second electrical stimulation signal via the second electrode to the second conductive point of the sheath, such that electrical stimulation is provided sequentially and successively via the rows of conductive points or via the columns of conductive points such that a first row or first column of the conductive points provide electrical stimulation at or during a first time and a second row or second column of the conductive points provide electrical stimulation at or during a second time that follows the first time.

Note that the DSCs may be implemented in any of a variety of ways including as described herein in various examples, embodiments, etc. In one example, the first DSC includes a power source circuit operably coupled via a single line to the first electrode that couples to the first conductive point. When enabled, the power source circuit is configured to provide an analog signal via the single line coupling to the first electrode that couples to the first conductive point. The analog signal includes at least one of a DC (direct current) component or an oscillating component. The first DSC also includes a power source change detection circuit operably coupled to the power source circuit. When enabled, the power source change detection circuit is configured to detect an effect on the analog signal that is based on coupling of the first electrical stimulation signal into the first location of the bodily portion of the user and to generate the first digital signal that is representative of the first change of the first electrical stimulation signal.

In addition, in some specific examples, the power source circuit is implemented to include a power source to source at least one of a voltage or a current via the single line to the first electrode that couples to the first conductive point. The power source change detection circuit also includes a power source reference circuit configured to provide at least one of a voltage reference or a current reference. The power source change detection circuit also includes a comparator configured to compare the at least one of the voltage and the current provided via the single line to the first electrode that couples to the first conductive point to the at least one of the voltage reference and the current reference to produce the analog signal.

In another example of operation and implementation, an electrical stimulation system includes a sheath that includes conductive points that are operative to facilitate electrical stimulation to a bodily portion of a user. The electrical stimulation system includes drive-sense circuits (DSCs) operably coupled to the conductive points of the sheath via electrodes. The DSCs are configured to generate an electrical stimulation signals based on reference signals. The electrical stimulation signals are coupled into the bodily portion of the user via the conductive points of the sheath. When enabled, a DSC is configured to provide an electrical stimulation signal via an electrode to a conductive point of the sheath, wherein the electrical stimulation signal is coupled into a location of the bodily portion of the user that is in proximity to or in contact with the conductive point of the sheath. The DSC is also configured to sense, via the conductive point of the sheath and via the electrode, a change of the electrical stimulation signal based on coupling of the electrical stimulation signal into the location of the bodily portion of the user. The DSC is also configured to generate a digital signal that is representative of the change of the electrical stimulation signal.

In addition, when enabled, the plurality of DSCs is configured to provide the electrical stimulation signals via the electrodes to the conductive points sequentially and successively via respective subsets of the conductive points that each include fewer than all of the conductive points such that a first subset of conductive points provide electrical stimulation at or during a first time and a second subset of conductive points provide electrical stimulation at or during a second time that follows the first time.

The electrical stimulation system also includes one or more processing modules that includes and/or is coupled to memory that stores operational instructions. The one or more processing modules is operably coupled to the DSCs. When enabled, the one or more processing modules is configured to execute the operational instructions to generate the reference signals and to process digital signals generated by the plurality of DSCs including the digital signal generated by the DSC to determine a response profile of one or more electrical characteristics of the bodily portion of the user.

In certain examples, the conductive points of the sheath are arranged in a matrix pattern including rows of conductive points and columns of conductive points. The first subset of conductive points includes a first row of conductive points, and the second subset of conductive points includes a second row of conductive points.

FIG. 29E includes schematic block diagrams of embodiments of sheaths that are operative to facilitate sensing and/or stimulation across one or more bodily portions of a subject to perform trend tracking based on bilateral symmetry comparative analysis in accordance with the present invention.

Referring to the embodiment 2906, this diagram shows two sheaths 2914-2 as being in contact with or wrapped around the quadriceps of the subject. In an example of operation and implementation, consider an instance in which one of the quadriceps of the subject is healthy and the other is undergoing rehabilitation, such as after an injury, overexertion, and/or other event(s) that caused some distress to one of the quadricep. By employing to separate sheaths that each respectively are serviced by DSCs, in communication with one or more processing modules, etc., sensing, stimulation, and/or impedance sensing may be performed with respect to one of the quadriceps, such as the one undergoing rehabilitation, based on sensing, stimulation, and/or impedance sensing with respect to the other of the quadriceps. Such sensing, stimulation, and/or impedance sensing with respect to the healthy quadricep may be used to determine status regarding the rehabilitation of the other quadricep. For example, comparison of the healthy quadricep as a baseline to be used to determine whether or not the quadricep undergoing rehabilitation is progressing satisfactorily or has fully been rehabilitated.

Referring to the embodiment 2907, this diagram is similar to the previous one yet shows two sheaths 2914-2 as being in contact with or wrapped around the biceps of the subject. In an example of operation and implementation, consider an instance in which one of the biceps of the subject is healthy and the other is undergoing rehabilitation, such as after an injury, overexertion, and/or other event(s) that caused some distress to one of the bicep. By employing to separate sheaths that each respectively are serviced by DSCs, in communication with one or more processing modules, etc., sensing, stimulation, and/or impedance sensing may be performed with respect to one of the biceps, such as the one undergoing rehabilitation, based on sensing, stimulation, and/or impedance sensing with respect to the other of the biceps. Such sensing, stimulation, and/or impedance sensing with respect to the healthy bicep may be used to determine status regarding the rehabilitation of the other bicep. For example, comparison of the healthy bicep as a baseline to be used to determine whether or not the bicep undergoing rehabilitation is progressing satisfactorily or has fully been rehabilitated.

Note that the examples of quadricep and bicep are not exhaustive of such sensing, stimulation, and/or impedance sensing that may be performed with respect to one bodily portion of the subject and used in comparison to another bodily portion of the subject based on bilateral symmetry of the subject. For example, similar sensing, stimulation, and/or impedance sensing could also be performed with respect to the calves, knees, elbows, forearms, wrists, shoulders, etc. of the subject. In certain examples, consider it the subject being an athlete who has suffered an injury in an athletic competition or practice, such as with respect to a bodily portion of the subject on one side of the body that has a corresponding other bodily section on the other side of the body due to the bilateral symmetry of the subject. Such sensing, stimulation, and/or impedance sensing based on one of the bodily portions such as serving as a baseline may be used to determine the efficacy of the sensing, stimulation, and/or impedance sensing of another bodily portion based on the bilateral symmetry of the subject.

FIG. 29F includes schematic block diagrams of an embodiment 2908 of one or more sheaths that are operative to facilitate sensing and/or stimulation across one or more bodily portions of a subject during physical activity including adaptation thereof in accordance with the present invention. Note that such a sheath 2914-1 that is in contact with or wrapped around the bicep to the subject or a sheath 2914-2 that is in contact with the wrapped around the quadricep of the subject. Note that other examples of a sheath may be implemented with respect to one or more other bodily portions of the subject.

In an example of operation and implementation, the subject is interactive with exercise equipment. Examples of such exercise, may include any one or more of the treadmill, elliptical trainer, a treadmill, a stationary bike, etc. In many such exercise equipment includes a control console. In certain examples, a control console is implemented to include functionality of the computing device. Such functionality may include functionality of various embodiments of computing devices described herein, such as computing device 12 of FIG. 2, computing device 14 of FIG. 3, computing device 18 of FIG. 4, among others, as described herein.

In an example of operation and implementation, the one or more sheaths are in contact with her wrapped around one or more bodily portions of the subject to perform sensing, stimulation, and/or impedance sensing of one or more bodily portions of the subject as the subject is interacting with the exercise government. For example, during an exercise program being conducted with the exercise equipment, one or more DSCs service one or more sensing and/or stimulation conductive points of the one or more sheaths to facilitate sensing, stimulation, and/or impedance sensing of one or more bodily portions of the subject as the subject is interacting with the exercise government. Note that the one or more DSCs are in communication with one or more processing modules as well. Note that all such electrical components may be implemented within the control console of the exercise equipment, with electrodes connecting the DSCs within the control console to the sensing and/or stimulation conductive points of the one or more sheaths.

In certain examples, note that the stimulation being provided to the subject may be modified and adapted based on bodily condition, status, etc. such as heart rate, respiratory rate, change of impedance, etc. of the subject. In addition, and certain other examples, note that the stimulation being provided the subject may be modified and adapted based on the particular point in an exercise program that is being provided by the exercise equipment (e.g., as controlled by the control console) for consumption by the subject. For example, consider an exercise equipment of a stair master, and exercise program is may be provided for consumption by the subject such that the exercise program varies over the course of the exercise program (e.g., providing the effect of steeper or less steep inclines to be climbed over time, providing the effect of walking along a flat surface, providing the effect of walking down the hill of a particular steepness, etc.) as may be desired, the sensing, stimulation, and/or impedance sensing of one or more bodily portions of the subject as the subject is interacting with the exercise government may be modified during the subject interactivity with the exercise equipment, in real time, based on the number of considerations including the bodily status or response of the subject, the status or point within an exercise program of the exercise equipment, etc.

FIG. 29G includes schematic block diagrams of an embodiment 2909 of a sheath that is in communication with a control console in accordance with the present invention. This diagram shows an example of a sheath 2914-10 that includes a power source 2990, such as a battery, or some other energy storage device such as a capacitor capable of storing a high degree of charge to provide power to one or more processing modules 42. In certain examples, the power source 2990 also provides power to one or more DSCs 28 that service the sensing and/or stimulation conductive points of the sheath 2914-10. However, note that the one or more processing modules 42 may be implemented to provide power to the one or more DSCs 28 that service the sensing and/or stimulation conductive points of the sheath 2914-10 in other examples. The sheath 2914-10, via the one or more processing modules 42, includes functionality to support communication via one or more communication links to a control console.

In certain embodiments, note that the control console is that of exercise equipment such as described with respect to the previous diagram. In certain examples, a control console is implemented to include functionality of the computing device. Such functionality may include functionality of various embodiments of computing devices described herein, such as computing device 12 of FIG. 2, computing device 14 of FIG. 3, computing device 18 of FIG. 4, among others, as described herein. In this diagram, the control console also includes a communication interface 2971 that is in communication with one or more processing modules 42. Note that the communication interface 2971 includes functionality of a transmitter TX 2972 and a receiver TX 2973.

In certain examples, the communication facilitated between the control console (e.g., computing device 12-29) and the sheath 2914-10 is performed using wireless communication means. For example, such communication may be facilitated via Bluetooth, WiFi, cellular, and/or any other wireless communication means etc. including any proprietary wireless communication means. Such an implementation provides the ability for the sheath 2914-10 to operate without the necessity of any wires connecting between it and the control console. For example, information may be provided between the respective one or more processing modules of the sheath 2914-10 and the control console via wireless communication means thereby freeing up the user who is interacting with the exercise equipment. In addition, note that such a sheath 2914-10 may be employed to facilitate sensing, stimulation, and/or impedance sensing of one or more bodily portions of a subject even when not specifically interacting with exercise equipment. In an example of operation and implementation, a computing device is supporting wireless communication with the sheath 2914-10 as the subject is doing calisthenics, running in place, doing sit-ups, running around the track that is within a sufficient range in proximity such that wireless communication may be supported between the computing device and the sheath 2914-10, etc.

FIG. 30 is a schematic block diagram of an embodiment 3000 of one or more electrodes that are serviced by one or more DSCs that includes capability to provide single-ended or differential sensing and/or stimulation across one or more bodily portions of a subject in accordance with the present invention. This diagram shows multiple electrodes 1410 that are in proximity to or in contact with the skin surface of a subject and/or implanted into one or more bodily sections of the subject. The electrodes 1410 are serviced respectively by DSCs 28, such that a first DSC 28 services a first electrode 1410 that is associated with a first contact point (e.g., in proximity to or in contact with a first contact point of the skin surface of a subject and/or a first implanted contact point of a bodily section of the subject), a second DSC 28 services a second electrode 1410 that is associated with a second contact point (e.g., in proximity to or in contact with a second contact point of the skin surface of a subject and/or a second implanted contact point of a bodily section of the subject), and so on.

Having individual respective electrodes 1410 in comparison to the sheath that includes sensing and/or stimulation conductive points provides a different manner of implementation to provide sensing and/or stimulation to one or more bodily sections of the subject. Certain applications may be more well suited for sensing and/or stimulation using a sheath, and other applications may be more well suited for sensing and/or stimulation using individual respective electrodes 1410. this diagram shows the electrodes being in proximity to one contact with the skin surface of the chest or thorax bodily section of the subject and/or implanted into the body of the subject in the general location of the chest or thorax (e.g., such as implanted into the chest for any of a number of purposes such as providing a pace signal to the heart, detecting cardiac electrical activity, measuring impedance of the heart or one or more other bodily sections of the chest or thorax, etc.).

Again, note that the DSCs 28 may be implemented to perform a number of functions with respect to providing electrical signaling to the subject (e.g., providing electrical stimulation to one or more bodily sections of the subject, providing a pace signal to assist cardiac operation, etc.) and also measuring one or more electrical characteristics of the subject (e.g., detecting cardiac electrical activity, measuring impedance of one or more bodily sections of the subject, etc.).

With respect to performing heart and/or intrathoracic impedance sensing of the subject, note that such impedance sensing may be implemented in a variety of ways including using implantable electrodes within the heart and/or chest or thorax of the subject or in a noninvasive manner such as using electrodes that are in proximity to or in contact with the surface of the skin of the subject in the general region of the heart and/or chest or thorax of the subject. As the DSCs 28 provide electrical signaling that is coupled into the body of the subject in the general region of the heart and/or chest or thorax of the subject, the DSCs 28 are configured to detect impedance and/or impedance change of those bodily sections of the subject.

There is a correlation between impedance of the heart and/or chest or thorax of the subject and mortality risk. Generally, patients with a higher impedance of the heart and/or chest or thorax have a correspondingly lower mortality risk than those with lower or intermediate impedance heart and/or chest or thorax. In addition, monitoring and tracking the trend of the impedance of the heart and/or chest or thorax over time can provide medical professionals valuable information regarding the direction of mortality risk of the subject. For example, a baseline measurement of impedance of the heart and/or chest or thorax of a particular subject is made based on a corresponding bill of good health of that subject. Then, over time, such as based on subsequent office visits of the subject to a medical professional, subsequent measurements of the impedance of the heart and/or chest or thorax of a particular subject are made so that trend tracking of the impedance of the heart and/or chest or thorax of that particular subject may be made over time to provide information to the medical professional regarding the direction in which the mortality risk of that subject is going, whether improving or degrading.

Also, measurement of impedance of the thorax of the subject can also provide indication of heart health including whether or not the subject is suffering from congestive heart failure. Electrical resistivity, alternatively referred to as specific electrical resistance or volume resistivity provides a measurement of how strongly a material conducts or impedes electric current applied to it. A material having a relatively low electrical resistivity will allow electric current to pass through it relatively easily, whereas a material having a relatively high electrical resistivity will not readily allow electric current passed through it. Electrical resistivity is often represented by the Greek letter ρ (rho) and is provided in Ohm-meters (ω-m). For example, the electrical resistivity of thoracic tissue may be in the range of $\rho=200\text{-}5000$ Ohm-cm, and the electrical resistivity of blood and fluid may be in the range of $\rho=65\text{-}150$ Ohm-cm. as such, certain bodily sections of a subject with higher blood for fluid content will have correspondingly lower impedance.

Providing impedance measurement of heart and/or chest or thorax of the subject can provide useful information to medical professionals to assess the health of the subject. An impedance measurement of a bodily section of a subject may alternatively be referred to as the bio impedance or the bioelectrical impedance of that bodily section of the subject. By measuring the impedance of the heart and/or chest or thorax of the subject, a determination of the amount of fluid within the heart and/or chest or thorax of the subject may be made. For example, impedance measurements the heart and/or chest or thorax of the subject (e.g., hemodynamic measurements) in comparison to those measurements based on the known ranges of electrical resistivity of thoracic tissue in comparison to the electrical resistivity of blood and fluid (e.g., blood and fluid having relatively lower electrical resistivity than thoracic tissue) can provide medical professionals some indication of the amount of fluid accumulation in the setting of congestion, such as with respect to the subject who may be suffering from or trending in the direction of congestive heart failure. For example, performing trend tracking and impedance (Z) monitoring as a function of time of the heart and/or chest or thorax of the subject is a useful tool for medical professionals to identify the amount of fluid in the heart and/or chest or thorax of the subject.

In addition, note that impedance at a particular location of the subject or with respect to a particular bodily section of the subject may be made to perform trend tracking and impedance (Z) monitoring as a function of time, and also note that an impedance profile corresponding to multiple locations of the subject or with respect to a particular bodily section of the subject may alternatively made to in accordance with performing impedance profile trend tracking and impedance (Z) monitoring as a function of time. Regardless of the particular implementation by which trend tracking and impedance (Z) monitoring is performed, whether with respect to one particular electrode, or multiple electrodes thereby generating an impedance profile, trend tracking and impedance (Z) monitoring can provide valuable information to medical professionals regarding the health status of the subject. In addition, using one or more DSCs 28 as described herein provides significant improvement over prior art impedance measurement technology by providing much higher precision and accuracy than can be achieved using prior art impedance measurement technology.

FIGS. 31A and 31B are schematic block diagrams of embodiments 3101 and 3102 of trend tracking and impedance (Z) monitoring of one or more electrodes to assist in diagnosis of health condition of a subject in accordance with the present invention. Referring to embodiment 3101 of FIG. 31A, this diagram shows multiple electrodes (e.g., electrode 1, 2, 3, and 4) that are either provisioned individually, such as with respect to FIG. 30, or included within a sheath, such as with respect to FIG. 29A, 29B, 29C, or 29D that are operative to facilitate sensing and/or stimulation of one or more bodily sections of the subject. Note that any different number of electrodes may alternatively be used, including fewer or more than 4 as used in this together diagram. This diagram shows monitoring of the impedance of a number of electrodes (e.g., shown as 4 electrodes in this diagram providing an impedance (Z) profile) at different respective times and comparing the impedance profile of those respective electrodes at different times. Such trend tracking and impedance (Z) monitoring of the electrodes when placed at the same locations with respect to a subject can provide valuable information to medical professionals. to determine whether or not, when and identifying whether or not a problem exists such as whether or not the mortality risk of the subject is improving or degrading, whether or not the subject is trending towards or away from congestive heart failure, etc.

Examples of such considerations used to determine whether or not a problem exists with the subject, whether or not the subject is trending towards or away from a higher mortality risk, whether or not the subject is trending towards or away from congestive heart failure, etc. may include any one or more of a trajectory by which the Z profile is changing, a rate at which the Z profile is changing (e.g., change of the Z profile as a function of time), whether or not the Z profile compares favorably with a normal range for that subject, whether or not one or more of the impedances of the respective electrodes included within the Z profile compare favorably the normal range for that subject, etc.

On the left-hand side of the diagram, at or during time 1, a Z profile 1 corresponds to the respective impedances of the electrodes being monitored at or during time 1. For example, the impedance of the respective electrodes may be the same or approximately or substantially the same (e.g., the same value, or within a certain percentage of being same as one another, such as within 1%, 2%, 5%, or some other value). In some examples, a baseline Z profile for a subject is determined based on the initial impedances of the electrodes included within the Z profile during a first office visit of that subject to a medical professional. Such an initial Z profile may correspond to the subject being in good health (e.g., that subject having a bill of good health).

Then, monitoring of one or more characteristics associated with the Z profile of the subject is performed. Note that the different respective times 1, 2, and so on to n may be uniformly spaced apart, such as corresponding to different respective office visits to medical professionals on a substantially periodic basis (e.g., every A days, every B weeks, every C months, etc., such that A, B, and C are positive integers). However, note that the different respective times 1, 2, and so on to n may not be uniformly spaced apart, and yet may correspond to office visits to a medical professional (e.g., time 1 and time 2 spaced apart by 1 month, time 1 and time 2 spaced apart by 8 weeks, etc. . . . ). Regardless of how the data is collected, the trend tracking and impedance (Z) monitoring as performed using the one or more electrodes provides valuable information to the medical professionals regarding the health of the subject including the stability or lack thereof, trajectory, trend, etc. of the health of the subject.

Note that a normal range for that subject for one or more, or all, of the respective impedances of the electrodes included within the Z profile may be defined, and when all, or some acceptable number, of the electrodes included within the Z profile have impedance values within this normal range for the subject (e.g., that subject having a bill of good health), then no problem may be identified as existing for the subject. For example, consider a normal range for that subject extending from a certain percentage greater and less than certain percentage less than the baseline/initial impedances of electrodes included within the Z profile. In one example, consider an upper limit of the normal range for that subject to be X % greater than the baseline/initial impedances of electrodes included within the Z profile and a lower limit of the normal range for that subject to be Y % less than the baseline/initial impedances of electrodes included within the Z profile. Consider an example in which consider an upper limit of the normal range for that subject to be 5% greater than the baseline/initial impedances of electrodes included within the Z profile and a lower limit of the normal range for that subject to be 8% less than the baseline/initial impedances of electrodes included within the Z profile, then the normal range for that subject would extend from 0.92 to 1.05 of the baseline/initial impedances of electrodes included within the Z profile. Consider an example in which consider an upper limit of the normal range for that subject to be 10% greater than the baseline/initial impedances of electrodes included within the Z profile and a lower limit of the normal range for that subject to be 10% less than the baseline/initial impedances of electrodes included within the Z profile, then the normal range for that subject would extend from 0.9 to 1.1 of the baseline/initial impedances of electrodes included within the Z profile. Other values may alternatively be identified for upper and lower limits of the normal range for that subject in other examples and implementations based on any number of considerations. Examples of such considerations may be historical or past upper and lower values associated with normal range for the subject (e.g., that subject having a bill of good health).

Moving to the right in the diagram, consider an example at or during time 2 at which the Z profile has modified (e.g., consider Z profile 2 at or during time 2 in comparison to Z profile 1 at or during time 1), then a Z profile change a (delta a) may be viewed as a difference between the Z profile 2 at or during time 2 in comparison to Z profile 1 at or during time 1. For example, consider a situation in which the impedance of the heart and/or chest or thorax of the subject is decreasing, such as may be associated with an increase of blood or fluid content and any heart and/or chest or thorax of the subject. Considering the Z profile 2 at or during time 2, although the respective impedances of the electrodes included within the Z profile are included within the normal range for that subject at or during time 2, note that they are moving in the direction that, if continued, will be approaching the lower limit of the normal range for that subject and possibly expand outside of the normal range for that subject. This may be indicative of possible problems such as an increase of blood or fluid content and any heart and/or chest or thorax of the subject. For example, the Z profile at time 2, though still within the normal range of that subject, is trending towards decreased impedance that may be indicative of degrading health and/or increased mortality risk. Based on this information, medical professionals may initiate a treatment regime for the subject.

This process of monitoring may be continued, such as at or during different respective times. On the right hand side of the diagram, consider an example at or during some other time, time n, at which the Z profile has modified even further from a prior time (e.g., consider Z profile n at or during time n in comparison to Z profile 1 at or during time 1 or in comparison to Z profile 2 at or during time 2), then a Z profile change b (delta b) may be viewed as a difference between the Z profile 2 at or during time 2 or the Z profile 1 at or during time 1. With respect to the example of this diagram, know that each of the respective impedances of the electrodes included within the Z profile are outside of the normal range for that subject at or during time n. This may be indicative of an actual problems such as an increase of blood or fluid content and any heart and/or chest or thorax of the subject. Based on the determination of the existence of a problem based on the respective impedances of the electrodes included within the Z profile being outside of the normal range for that subject at or during time n, any one or more appropriate actions may be taken by the medical professionals in accordance with providing medical treatment to the subject. For example, the Z profile at time n, being outside of the normal range of that subject, may be indicative of very poor health and/or high mortality risk. Based on this information, medical professionals may initiate more aggressive treatment regime for the subject including intensifying existing treatment or providing urgent care as may be needed.

Generally speaking, such Z profile monitoring (e.g., based on the impedance (Z) (e.g., capacitance) of the respective electrodes included within the Z profile and be monitored to determine any changes as a function of time. Any one or more determinations may be made based on the rate of change, the trajectory of change, the direction of change, etc. of the Z profile and/or one or more individual impedances of electrodes within the Z profile to facilitate the determination of the status, health, etc. of the subject. Note that such determinations may also be made based on comparison of one or more characteristics associated with the Z profile in comparison to variation from expected/historical Z profile of the heart and/or chest or thorax of the subject.

Referring to embodiment 3102 of FIG. 31B, this diagram shows impedance (Z) monitoring of a singular electrode as may in proximity to or in contact with the subject, which may be implemented individually or within the sheath as described herein, etc. This diagram has some similarities to the previous diagram with at least one difference being that this diagram corresponds to monitoring the impedance of a single electrode. For example, this diagram shows an example of tracking and monitoring the impedance of electrode 1.

At or during a time 1, the impedance of electrode 1 is shown as being centered within a normal range for that subject. This impedance may be a baseline impedance of electrode 1 (e.g., an initial impedance such as corresponding to good health for the subject, such as the subject having a bill of good health).

At or during a time 2, the impedance of electrode 1 is shown as still being centered within the normal range for that subject, but with a slightly increased impedance yet still being within the normal range for the subject. In fact, the increase in impedance at this time 2 made correspond to an improvement in health of the subject.

At or during a time 3, the impedance of electrode 1 is shown as still less than at time 2 get still being within the normal range for that subject. At or during a time 4, the impedance of electrode 1 is shown as also being centered within the normal range for that subject (e.g., with approximately the same impedance measured at time 1).

At or during times 5 and 6, the impedance of electrode 1 is shown as being within the normal range for that subject, or at the bottom end of the normal range for that subject, with a relatively steep trajectory or fast rate of change and particularly decreasing over time. This approaching the limit of the normal range for that subject, even though remaining in the normal range for that subject, may indicate a degradation and health such as an increase in fluid within the heart and/or chest or thorax of the subject, and increased mortality risk, etc. For example, the impedance of electrode 1 at times 5 and 6, though still within the normal range of that subject, is trending towards decreased impedance that may be indicative of degrading health and/or increased mortality risk. Based on this information, medical professionals may initiate a treatment regime for the subject.

At or during a time n, the impedance of electrode 1 is shown as being outside of the normal range for that subject. For example, the impedance of electrode 1, being outside of the normal range of that subject, may be indicative of very poor health and/or high mortality risk. Based on this information, medical professionals may initiate more aggressive treatment regime for the subject including intensifying existing treatment or providing urgent care as may be needed.

Once a determination is made regarding a problem or a potential problem (e.g., such as associated with swelling, bulging, gas build up, etc.), one or more processing modules is configured to take one or more actions including any of those described above such as based on determination of a problem with the battery during charging, cease charging of the battery; alternatively, based on determination of a problem with the battery during non-charging, provide an error signal to facilitate the user taking action to remedy or mitigate the problem; shut down one or more processes or operations of a device in which the battery is implemented; etc.

FIG. 32 is a schematic block diagram of an embodiment 3200 of a novel electrocardiogram (ECG) (alternatively referred to as an EKG) machine that is serviced by DSCs coupled to ECG stickers via electrodes in accordance with the present invention. This diagram shows an ECG machine 3210 that operates using DSCs 28 as described herein instead of traditional technology employed within prior art ECG machines. For example, one or more processing models 42 is in syndication with DSCs 28 that respectively service electrodes 1410 that coupled to ECG leads/stickers 3220 that are in contact with the skin surface of a subject in the chest or thorax region. In an example of operation and implementation, the ECG leads/stickers 3220 are typical ECG leads/stickers that include a mechanism to keep them in place and in contact with the skin surface of the subject (e.g., an adhesive). The DSCs 28 are configured to detect electrical activity via the ECG leads/stickers 3220. Note that the number of ECG leads/stickers 3220 may be chosen to be any desired number, and certain applications operate using 12 ECG leads/stickers 3220. Generally speaking, any desired number of ECG leads/stickers 3220 may be employed in the given implementation. In one specific example, one (1) single ECG leads/sticker 3220 is employed and placed on the skin surface of the subject nearest to the heart of the subject.

For example, based on cardiac electrical activity within the cardiac conduction system in accordance with the electrical impulses traveling to the different respective portions of the heart to facilitate beating of the heart, those electrical impulses are coupled into the ECG leads/stickers 3220 and are then detected by the DSCs 28 via the electrodes 1410 that couple the DSCs 28 to the ECG leads/stickers 3220. This diagram shows yet another application by which appropriately implemented DSCs 28 may be used to detect electrical activity, namely, cardiac electrical activity within the cardiac conduction system. From certain perspectives, this diagram shows a replacement of existing, prior art ECG machines using DSCs 28 that respectively service ECG leads/stickers 3220 via electrodes 1410.

Note that DSCs 28 as described herein are configured to detect electrical signals including cardiac electrical activity within the cardiac conduction system of the subject with improved resolution and accuracy of the electrical response of the heart compared to existing, prior art ECG machines. Also, note that such a replacement of existing, prior art ECG machines using DSCs 28 that respectively service ECG leads/stickers 3220 via electrodes 1410 as described in this diagram may be realized much more cost effectively than existing, prior art ECG machines. For example, existing, prior art ECG machines may cost anywhere in the range of $1,000s of dollars (e.g., $1,000 to $4,000 or even more). An implementation as described in this diagram to detect cardiac electrical activity including DSCs 28 that respectively service ECG leads/stickers 3220 via electrodes 1410 may be realized for a fraction of the cost of an existing, prior art ECG machine.

FIG. 33 is a schematic block diagram of an embodiment of another method 3300 for execution by one or more devices in accordance with the present invention. The method 3300 operates in step 3310 by operating one or more DSCs for providing one or more signals via one or more electrodes perform sensing and/or stimulation 3310. Note that such sensing and/or stimulation may be performed in accordance with any of a number of operations including those described herein. Some examples of such sensing and or stimulation may include any one or more of pace signal delivery 3313 such as in accordance with providing electrical impulses via a pacemaker implementation to assist in proper cardiac function of the subject, servicing of ECG leads/stickers 3312 such as in accordance with detecting cardiac electrical activity within the cardiac conduction system of a subject, operating the one or more DSCs to provide a current source signal 3313 such as in accordance with providing electrical stimulus to one or more bodily portions of the subject, operating one or more DSCs to provide a current sink signal 3314 or treating an abnormally fast heart in a subject suffering from tachycardias, operating the one or more DSCs to detect cardiac electrical activity 3315 within the cardiac conduction system of a subject in a manner not specifically using ECG leads/stickers, operating the one or more DSCs to sense impedance of one or more bodily portions of the subject or to perform trend tracking and impedance (Z) monitoring 3316 of one or more bodily portions of the subject to provide information regarding the health status of the subject, and/or any other desired function 3317 including those described herein.

The method 3300 also operates in step 3320 by receiving information, via the one or more DSCs, corresponding to the one or more signals provided via the one or more electrodes to perform the sensing and or stimulation. In some examples, this information is provided as digital data that is generated by the one or more DSCs and is provided to one or more processing modules. The method 3300 operates in step 3330 by processing the information corresponding to the one or more signals provided via one or more electrodes to perform the sensing and/or stimulation. In some implementations, such processing in step 3330 is performed within one or more processing modules.

The method 3300 also operates in step 3340 by determining whether to perform adaptation to the one or more signals provided via the one or more electrodes to perform the sensing and/or stimulation. Such a determination may be made based on any of a variety of considerations including favorable or unfavorable comparison to one or more conditions. For example, consider a pacemaker implementation using the one or more DSCs for providing one or more pace signals via electrodes to facilitate improved cardiac operation within the subject. Based on the pace signal characteristics not facilitating capture thereby initiating a heartbeat in the subject, the pace signal may be adapted in terms of one or more of its characteristics such as signal magnitude, whether voltage or current, pulse width, etc. thereby tuning the pace signal so as to facilitate capture by the appropriate portion of the heart of the subject.

For another example, consider an electrical stimulation implementation using one or more DSCs for providing one or more electrical signals to an injured bodily portion of the subject to assist in the rehabilitation of the subject. Based on a treatment program failing to favorable results, one or more electrical characteristics of the one or more electric signals may be adapted (e.g., increase signal levels of the one or more electric signals, modify frequency of one or more oscillating components of the one or more electric signals, etc.).

For another example, consider one or more electrical characteristics of a bodily portion of the subject has changed. Based on detection of the change of these one or more electrical characteristics of the bodily portion of the subject, one or more electrical signals may be adapted based on such changes. For example, based on an increased impedance of the bodily portion of the subject, a signal level that is providing a sensing and or stimulation signal to that bodily portion of the subject may be increased in response to that increased impedance. Generally speaking, a determination to perform adaptation to the one or more signals provided via one or more electrodes to perform sensing and/or stimulation may be made for based on any desired criterion.

Based on a determination not to perform any adaptation in step 3350, the method 3300 branches and ends. In an alternative variant of the method 3300, based on a determination not to perform any adaptation in step 3350, the method 3300 branches and loops back to step 3310. This alternative variants of the method 3300 may be viewed as continuing to operate the one or more DSCs for providing the one more signals via the one or more electrodes to perform sensing and/or stimulation without performing any modification or adaptation to the one or more signals.

Based on the determination to perform adaptation in step 3350, the method 3300 branches to step 3360 and the method 3300 operates by identifying one or more electrical characteristics of the one or more signals to be adapted.

The method 3300 operates in step 3370 by adapting the one or more electrical characteristics of the one or more signals that are provided via one or more electrodes from the one or more DSCs to perform sensing and/or stimulation. Examples of such modification of one or more electrical characteristics of the one or more signals may include modification of any one or more DC level, oscillating component magnitude and/or frequency, current level, and/or any other electrical characteristic of the one or more signals. In certain examples, adjustment of one or more of the reference signals employed by the one or more DSCs is performed to effectuate the adaptation of the one or more electrical characteristics of the one or more signals.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provides an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, a quantum register or other quantum memory and/or any other device that stores data in a non-transitory manner. Furthermore, the memory device may be in a form of a solid-state memory, a hard drive memory or other disk storage, cloud memory, thumb drive, server memory, computing device memory, and/or other non-transitory medium for storing data. The storage of data includes temporary storage (i.e., data is lost when power is removed from the memory element) and/or persistent storage (i.e., data is retained when power is removed from the memory element). As used herein, a transitory medium shall mean one or more of: (a) a wired or wireless medium for the transportation of data as a signal from one computing device to another computing device for temporary storage or persistent storage; (b) a wired or wireless medium for the transportation of data as a signal within a computing device from one element of the computing device to another element of the computing device for temporary storage or persistent storage; (c) a wired or wireless medium for the transportation of data as a signal from one computing device to another computing device for processing the data by the other computing device; and (d) a wired or wireless medium for the transportation of data as a signal within a computing device from one element of the computing device to another element of the computing device for processing the data by the other element of the computing device. As may be used herein, a non-transitory computer readable memory is substantially equivalent to a computer readable memory. A non-transitory computer readable memory can also be referred to as a non-transitory computer readable storage medium.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A pacemaker system comprising:
  a drive-sense circuit (DSC) operably coupled to a pacemaker lead and configured to provide a pace signal including electrical impulses via the pacemaker lead to an electrically responsive portion of a cardiac conductive system of a subject to facilitate cardiac operation of a cardiovascular system of the subject and simultaneous to sense cardiac electrical activity of the cardiovascular system of the subject that is generated in response to the pace signal and electrically coupled into the pacemaker lead, the DSC including:
    a comparator configured to produce an error signal based on comparison of a reference signal to the pace signal, wherein the reference signal is received at a first input of the comparator, and the pace signal is received at a second input of the comparator;
    a dependent current supply configured to generate the pace signal based on the error signal and to provide the pace signal via a single line that couples to the pacemaker lead and the second input of the comparator; and
    an analog to digital converter (ADC) configured to process the error signal to generate a digital signal that is representative of the cardiac electrical activity of the cardiovascular system of the subject that is sensed via the pacemaker lead;
  memory that stores operational instructions; and
  one or more processing modules operably coupled to the DSC and the memory, wherein, when enabled, the one or more processing modules is configured to execute the operational instructions to process the digital signal generated by the DSC to determine the cardiac electrical activity of the cardiovascular system of the subject that is sensed via the pacemaker lead.

2. The pacemaker system of claim 1 further comprising:
  a signal generator operably coupled to the second input of the comparator, wherein, when enabled, the signal generator configured to generate the reference signal and to provide the reference signal to the second input of the comparator.

3. The pacemaker system of claim 2, when enabled, the signal generator is further configured to:
  adjust one or more electrical characteristics of the reference signal to facilitate generation of the pace signal by the DSC to facilitate capture by the cardiac conductive system of the subject in response to the pace signal.

4. The pacemaker system of claim 3, wherein adjustment of the one or more electrical characteristics of the reference signal causes adjustment of at least one electrical characteristic of the pace signal including at least one of:
  a magnitude of the electrical impulses of the pace signal;
  a pulse width of the electrical impulses of the pace signal;
  an amount of current level delivered via the electrical impulses of the pace signal; or
  a frequency or rate of the electrical impulses of the pace signal.

5. The pacemaker system of claim 1, wherein, when enabled, the one or more processing modules is further configured to execute the operational instructions to generate the reference signal and to provide the reference signal to the second input of the comparator.

6. The pacemaker system of claim 5, wherein, when enabled, the one or more processing modules is further configured to execute the operational instructions to:

adjust one or more electrical characteristics of the reference signal to facilitate generation of the pace signal by the DSC to facilitate capture by the cardiac conductive system of the subject in response to the pace signal.

7. The pacemaker system of claim 6, wherein adjustment of the one or more electrical characteristics of the reference signal causes adjustment of at least one electrical characteristic of the pace signal including at least one of:
a magnitude of the electrical impulses of the pace signal;
a pulse width of the electrical impulses of the pace signal;
an amount of current level delivered via the electrical impulses of the pace signal; or
a frequency or rate of the electrical impulses of the pace signal.

8. The pacemaker system of claim 1, wherein the pacemaker lead is implanted in or in proximity to a sinoatrial (SA) node of the cardiovascular system of the subject, and wherein the pacemaker lead is implemented with one single conductor.

9. The pacemaker system of claim 1, wherein the pacemaker lead is implanted in or in proximity to a ventricle of the cardiovascular system of the subject, and wherein the pacemaker lead is implemented with one single conductor.

10. The pacemaker system of claim 1 further comprising:
another DSC operably coupled to another pacemaker lead and configured to provide another pace signal including other electrical impulses via the another pacemaker lead to another electrically responsive portion of the cardiac conductive system of the subject to facilitate cardiac operation of the cardiovascular system of the subject.

11. The pacemaker system of claim 1 further comprising:
another DSC operably coupled to another pacemaker lead and configured to provide another pace signal including other electrical impulses via the another pacemaker lead to another electrically responsive portion of the cardiac conductive system of the subject to facilitate cardiac operation of the cardiovascular system of the subject and simultaneous to sense cardiac electrical activity of the cardiovascular system of the subject that is generated in response to at least one of the pace signal or the another pace signal and electrically coupled into the another pacemaker lead.

12. A pacemaker system comprising:
a drive-sense circuit (DSC) operably coupled to a pacemaker lead and configured to provide a pace signal including electrical impulses via the pacemaker lead to an electrically responsive portion of a cardiac conductive system of a subject to facilitate cardiac operation of a cardiovascular system of the subject and simultaneous to sense cardiac electrical activity of the cardiovascular system of the subject that is generated in response to the pace signal and electrically coupled into the pacemaker lead, the DSC including:
a comparator configured to produce an error signal based on comparison of a reference signal to the pace signal, wherein the reference signal is received at a first input of the comparator, and the pace signal is received at a second input of the comparator;
a dependent current supply configured to generate the pace signal based on the error signal and to provide the pace signal via a single line that couples to the pacemaker lead and the second input of the comparator; and
an analog to digital converter (ADC) configured to process the error signal to generate a digital signal that is representative of the cardiac electrical activity of the cardiovascular system of the subject that is sensed via the pacemaker lead;
a signal generator operably coupled to the second input of the comparator, wherein, when enabled, the signal generator configured to generate the reference signal and to provide the reference signal to the second input of the comparator;
memory that stores operational instructions; and
one or more processing modules operably coupled to the DSC and the memory, wherein, when enabled, the one or more processing modules is configured to execute the operational instructions to process the digital signal generated by the DSC to determine the cardiac electrical activity of the cardiovascular system of the subject that is sensed via the pacemaker lead.

13. The pacemaker system of claim 12, when enabled, the signal generator is further configured to:
adjust one or more electrical characteristics of the reference signal to facilitate generation of the pace signal by the DSC to facilitate capture by the cardiac conductive system of the subject in response to the pace signal.

14. The pacemaker system of claim 13, wherein adjustment of the one or more electrical characteristics of the reference signal causes adjustment of at least one electrical characteristic of the pace signal including at least one of:
a magnitude of the electrical impulses of the pace signal;
a pulse width of the electrical impulses of the pace signal;
an amount of current level delivered via the electrical impulses of the pace signal; or
a frequency or rate of the electrical impulses of the pace signal.

15. The pacemaker system of claim 12, wherein the pacemaker lead is implanted in or in proximity to a sinoatrial (SA) node of the cardiovascular system of the subject, and wherein the pacemaker lead is implemented with one single conductor.

16. The pacemaker system of claim 12, wherein the pacemaker lead is implanted in or in proximity to a ventricle of the cardiovascular system of the subject, and wherein the pacemaker lead is implemented with one single conductor.

17. A pacemaker system comprising:
a drive-sense circuit (DSC) operably coupled to a pacemaker lead and configured to provide a pace signal including electrical impulses via the pacemaker lead to an electrically responsive portion of a cardiac conductive system of a subject to facilitate cardiac operation of a cardiovascular system of the subject and simultaneous to sense cardiac electrical activity of the cardiovascular system of the subject that is generated in response to the pace signal and electrically coupled into the pacemaker lead, the DSC including:
a comparator configured to produce an error signal based on comparison of a reference signal to the pace signal, wherein the reference signal is received at a first input of the comparator, and the pace signal is received at a second input of the comparator;
a dependent current supply configured to generate the pace signal based on the error signal and to provide the pace signal via a single line that couples to the pacemaker lead and the second input of the comparator; and
an analog to digital converter (ADC) configured to process the error signal to generate a digital signal that is representative of the cardiac electrical activity of the cardiovascular system of the subject that is sensed via the pacemaker lead;

a signal generator operably coupled to the second input of the comparator, wherein, when enabled, the signal generator configured to generate the reference signal and to provide the reference signal to the second input of the comparator;

memory that stores operational instructions; and one or more processing modules operably coupled to the DSC and the memory, wherein, when enabled, the one or more processing modules is configured to execute the operational instructions to:

generate the reference signal and to provide the reference signal to the second input of the comparator; and process the digital signal generated by the DSC to determine the cardiac electrical activity of the cardiovascular system of the subject that is sensed via the pacemaker lead.

18. The pacemaker system of claim 17, wherein, when enabled, the one or more processing modules is further configured to execute the operational instructions to:

adjust one or more electrical characteristics of the reference signal to facilitate generation of the pace signal by the DSC to facilitate capture by the cardiac conductive system of the subject in response to the pace signal.

19. The pacemaker system of claim 18, wherein adjustment of the one or more electrical characteristics of the reference signal causes adjustment of at least one electrical characteristic of the pace signal including at least one of:

a magnitude of the electrical impulses of the pace signal;

a pulse width of the electrical impulses of the pace signal;

an amount of current level delivered via the electrical impulses of the pace signal; or a frequency or rate of the electrical impulses of the pace signal.

20. The pacemaker system of claim 12, wherein the pacemaker lead is implanted in or in proximity to a sinoatrial (SA) node or a ventricle of the cardiovascular system of the subject, and wherein the pacemaker lead is implemented with one single conductor.

\* \* \* \* \*